US011446357B2

(12) United States Patent
Mahne et al.

(10) Patent No.: US 11,446,357 B2
(45) Date of Patent: *Sep. 20, 2022

(54) METHOD FOR TREATING DISEASE USING FOXP3+CD4+ T CELLS

(71) Applicant: Kyverna Therapeutics, Inc., Emeryville, CA (US)

(72) Inventors: Ashley Mahne, San Francisco, CA (US); John Lee, Alameda, CA (US); Lih-Yun Hsu, San Francisco, CA (US); Jeffrey Greve, Berkeley, CA (US)

(73) Assignee: Kyverna Therapeutics, Inc., Emeryville, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/552,841

(22) Filed: Dec. 16, 2021

(65) Prior Publication Data

US 2022/0143134 A1 May 12, 2022

Related U.S. Application Data

(63) Continuation of application No. 17/523,431, filed on Nov. 10, 2021.

(60) Provisional application No. 63/111,905, filed on Nov. 10, 2020.

(51) Int. Cl.
| | |
|---|---|
| *C12N 15/63* | (2006.01) |
| *C12N 5/0783* | (2010.01) |
| *C07K 14/47* | (2006.01) |
| *A61K 38/17* | (2006.01) |
| *A61K 39/395* | (2006.01) |
| *A61K 48/00* | (2006.01) |
| *A61K 35/17* | (2015.01) |
| *C07K 16/24* | (2006.01) |
| *C07K 16/28* | (2006.01) |

(52) U.S. Cl.
CPC .......... *A61K 38/177* (2013.01); *A61K 35/17* (2013.01); *A61K 38/1709* (2013.01); *A61K 38/1774* (2013.01); *A61K 38/1793* (2013.01); *A61K 39/3955* (2013.01); *A61K 48/0066* (2013.01); *C07K 14/4703* (2013.01); *C07K 14/4705* (2013.01); *C07K 16/248* (2013.01); *C07K 16/2866* (2013.01); *C12N 5/0636* (2013.01); *C12N 15/63* (2013.01); *C07K 2317/622* (2013.01); *C12N 2501/60* (2013.01)

(58) Field of Classification Search
CPC .............. A61K 39/3955; A61K 38/177; A61K 38/1709; A61K 38/1774; A61K 38/204; C12N 5/0636; C12N 15/63; C12N 5/0637; C07K 14/70525; C07K 14/7155; C07K 16/28

See application file for complete search history.

(56) References Cited

U.S. PATENT DOCUMENTS

2021/0008111 A1* 1/2021 Seng ............... C12N 15/86

FOREIGN PATENT DOCUMENTS

| WO | WO 2018/115865 | 6/2018 |
| WO | WO 2019/079034 | 4/2019 |
| WO | WO 2019/202323 | 10/2019 |
| WO | WO 2019/241549 | 12/2019 |
| WO | WO-2021079149 A1 * | 4/2021 |
| WO | WO 2021/142302 | 7/2021 |

OTHER PUBLICATIONS

Bettelli et al. Foxp3 interacts with nuclear factor of activated T cells and NF-KB to repress cytokine gene expression and effector functions of T helper cells. Proc Natl Acad Sci USA 102(14): 5138-5143, 2005.*
Chicaybam et al. An efficient low cost method for gene transfer to T lymphocytes. PLos One 8(3): e60298, 2013.*
Dees et al. Regulatory T cell targeting in cancer: emerging strategies in immunotherapy. Eur J Immunol 51: 280-291, 2021.*
Hosokawa et al. How transcription factors drive choice of the T cell fate. Nature 21: 162-176, 2021.*
Hwang et al. Inflammation-induced Id2 promotes plasticity in regulatory T cells. Nature Comm 9: 4736, 2018.*
Koizumi et al. Transcriptional regulation of differentiation and functions of effector T regulatory cells. Cells 8: 939, 2019.*
Kwon et al. FoxP3 scanning mutagenesis reveals functional variegation and mild mutations with atypical autoimmune phenotypes. Proc Natl Acad Sci USA 115(2): E253-E262, 2018.*
Li et al. ICOS+ Tregs: a functional subset of Tregs in immune diseases. Front Immunol 11: 2104, 2020.*
Mansouri et al. Strategies for multigene expression in eukaryotic cells. Plasmid 75: 12-17, 2014.*
Seng et al. Coexpression of FOXP3 and a helios isoform enhances the effectiveness of human engineered regulatory T cells. Blood Adv 4(7): 1325-1339, Apr. 2020.*
Tao et al. Foxp3, regulatory T cell, and autoimmune diseases. Inflamm 40(1): 328-339, 2017.*
Wang et al. Transcriptional regulation of Treg homeostasis and functional specification. Cell Molec Life Sci 77: 4269-4287, 2020.*
Yagi et al. Crucial role of FOXP3 in the development and function of human CD25+CD4+ regulatory T cells. Int Immunol 16(11): 1643-1656, 2004.*
Zhao et al. Tregs: Where we are and what comes next? Front Immunol 8: 1578, 2017.*
Fu et al. A multiple redundant genetic switch 'locks in' the transcriptional signature of regulatory T cells. Nature Immunol 13(10): 972-980, 2012; final edited version.*

(Continued)

*Primary Examiner* — Bridget E Bunner
(74) *Attorney, Agent, or Firm* — Fish & Richardson P.C.

(57) ABSTRACT

This document relates to methods and materials for treating a mammal having an autoimmune disease. For example, materials and methods for producing a T cell comprising a FOXP3 polypeptide and one or more transcription factors are provided herein. Methods and materials for treating a mammal having an autoimmune disease comprising administering to a mammal having an autoimmune disease an effective amount of a T cell are also provided herein.

15 Claims, 2 Drawing Sheets

Specification includes a Sequence Listing.

(56) References Cited

OTHER PUBLICATIONS

Fussenegger et al. The impact of mammalian gene regulation concepts on functional genomic research, metabolic enginerring, and advanced gene therapies. Biotechnol Prog 17: 1-51, 2001.*

Garg et al. Blimp1 prevents methylation of FoxP3 and loss of regulatory T cell identity at sites of inflammation. Cell Reports 26: 1854-1868, 2019.*

Gong et al. Cytokine-dependent Blimp-1 expression in activated T cells inhibits IL-2 production. J Immunol 178: 242-252, 2007.*

Sundrud et al. Genetic reprogramming of primary human T cells reveals functional plasticity in Th cell differentiation. J Immunol 171 : 3542-3549, 2003.*

Akimova et al., "Human lung tumor FOXP3+ Tregs upregulate four "Treg-locking" transcription factors" JCI insight, Aug. 17, 2017;2(16): 21 pages, Aug. 17, 2017.

Cortez et al., "CRISPR screen in regulatory T cells reveals modulators of Foxp3" Nature, 582(7812): 28 pages, Jun. 2020.

Cuadrado et al., "Proteomic analyses of human regulatory T cells reveal adaptations in signaling pathways that protect cellular identity" Immunity, 48(5):1046-1059, May 15, 2018.

Fu et al., "A multiple redundant genetic switch locks in the transcriptional signature of regulatory T cells" Nature immunology, 13(10): 28 pages, Oct. 2012.

Gondek et al., "Cutting edge: contact-mediated suppression by CD4+ CD25+ regulatory cells involves a granzyme B-dependent, perforin-independent mechanism" The journal of immunology, 174(4): 5 pages, Feb. 15, 2005.

Hori et al., "Control of regulatory T cell development by the transcription factor Foxp3" Science, 299(5609):1057-1061, Feb. 14, 2003.

Li et al., "DNA-binding properties of FOXP3 transcription factor" Acta biochimica et biophysica Sinica, 49(9):792-799, Sep. 1, 2017.

Miyazaki et al., "Id2 and Id3 maintain the regulatory T cell pool to suppress inflammatory disease" Nature immunology, 15(8):767-776, Aug. 2014.

Morawski et al., "Foxp3 protein stability is regulated by cyclin-dependent kinase 2" Journal of Biological Chemistry, 288(34):24494-24502, Aug. 23, 2003.

O'Sullivan et al., "Natural killer cell memory" Immunity, 43(4):634-645, Oct. 20, 2015.

Pandiyan et al., "Origin and functions of pro-inflammatory cytokine producing Foxp3+ regulatory T cells" Cytokine, 76(1): 12 pages, Nov. 1, 2015.

Rauch et al., "Id3 maintains Foxp3 expression in regulatory T cells by controlling a transcriptional network of E47, Spi-B, and SOCS3" Cell reports, 17(11):2827-2836, Dec. 13, 2016.

Romano et al., "Past, present, and future of regulatory T cell therapy in transplantation and autoimmunit" Front. Immunol., 10(43): 5 pages, 2019.

Sakaguchi et al., "Regulatory T cells: how do they suppress immune responses?" International immunology, 21(10):1105-1011, Oct. 1, 2009.

Schumann et al., "Functional CRISPR dissection of gene networks controlling human regulatory T cell identity" Nature immunology, 21(11):1456-1466, Nov. 2020.

Sullivan et al., "Cutting edge: dynamic expression of Id3 defines the stepwise differentiation of tissue-resident regulatory T cells" The Journal of Immunology, 202(1):31-36, Jan. 1, 2019.

Trzonkowski et al., "CD4+ CD25+ T regulatory cells inhibit cytotoxic activity of T CD8+ and NK lymphocytes in the direct cell-to-cell interaction" Clinical immunology, 112(3):258-267, Sep. 1, 2004.

Wohlfert et al., "GATA3 controls Foxp3+ regulatory T cell fate during inflammation in mice" The Journal of clinical investigation, 121(11):4503-4515, Nov. 1, 2011.

Grzanka et al, "Roles and relationships in regulatory T cells", International Immunopharmacology, Feb. 18, 2013, 13(3):343-347.

Jaeckel et al, "Antigen-specific FoxP3-transduced T-cells can control established type 1 diabetes", American Diabetes Association, Feb. 1, 2005, 54(2): 306-310.

PCT International Search Report and Written Opinion in International Application No. PCT/US2021/058711, dated Mar. 11, 2022, 19 pages.

Rudra et al, "Transcription factor Foxp3 and its protein partners form a complex regulatory network", Nature Immunology, Oct. 1, 2012, 13(10): 1010-1019.

* cited by examiner

```
                              SEQUENCE LISTING

<160> NUMBER OF SEQ ID NOS: 14

<210> SEQ ID NO 1
<211> LENGTH: 2159
<212> TYPE: DNA
<213> ORGANISM: Homo sapiens

<400> SEQUENCE: 1
agtttcccac aagccaggct gatcctttc tgtcagtcca cttcaccaag cctgcccttg      60
gacaaggacc cgatgcccaa ccccaggcct ggcaagccct cggccccttc cttggccctt    120
ggcccatccc caggagcctc gcccagctgg agggctgcac ccaaagcctc agacctgctg    180
ggggcccggg gcccaggggg aaccttccag ggccgagatc ttcgaggcgg ggcccatgcc    240
tcctcttctt ccttgaaccc catgccacca tcgcagctgc agctctcaac ggtggatgcc    300
cacgcccgga cccctgtgct gcaggtgcac ccctggaga gccagccat gatcagcctc      360 acaccaccca ccaccgccac tggggtcttc tccctcaagg cccggcctgg cctcccacct    420
gggatcaacg tggccagcct ggaatgggtg tccagggagc cggcactgct ctgcaccttc    480
ccaaatccca gtgcacccag gaaggacagc acccttcgg ctgtgcccca gagctcctac     540
ccactgctgg caaatggtgt ctgcaagtgg cccggatgtg agaaggtctt cgaagagcca    600
gaggacttcc tcaagcactg ccaggcggac catcttctgg atgagaaggg cagggcacaa    660
tgtctcctcc agagagagat ggtacagtct ctggagcagc agctggtgct ggagaaggag    720
aagctgagtg ccatgcaggc ccacctggct gggaaaatgg cactgaccaa ggcttcatct    780
gtggcatcat ccgacaaggg ctcctgctgc atcgtagctg ctggcagcca aggccctgtc    840
gtcccagcct ggtctggccc ccggggaggcc cctgacagcc tgtttgctgt ccggaggcac    900
ctgtggggta gccatggaaa cagcacattc ccagagttcc tccacaacat ggactacttc    960
aagttccaca acatgcgacc ccctttcacc tacgccacgc tcatccgctg ggccatcctg   1020
gaggctccag agaagcagcg gacactcaat gagatctacc actggttcac acgcatgttt   1080
gccttcttca gaaaccatcc tgccacctgg aagaacgcca tccgcacaa cctgagtctg   1140 cacaagtgct ttgtgcgggt ggagagcgag aagggggctg tgtggaccgt ggatgagctg   1200
gagttccgca agaaacggag ccagaggccc agcaggtgtt ccaaccctac acctggcccc   1260
tgacctcaag atcaaggaaa ggaggatgga cgaacagggg ccaaactggt gggaggcaga   1320
ggtggtgggg gcagggatga taggccctgg atgtgcccac agggaccaag aagtgaggtt   1380
tccactgtct tgcctgccag ggcccctgtt ccccgctgg cagccacccc ctcccccatc    1440
atatcctttg ccccaaggct gctcagaggg gccccggtcc tggcccagc ccccacctcc    1500 gccccagaca cacccccag tcgagccctg cagccaaaca gagccttcac aaccagccac   1560
acagagcctg cctcagctgc tcgcacagat tacttcaggc ctggaaaagt cacacagaca   1620
cacaaaatgt cacaatcctg tccctcactc aacacaaacc ccaaaacaca gagagcctgc   1680
ctcagtacac tcaaacaacc tcaaagctgc atcatcacac aatcacacac aagcacagcc   1740
ctgacaaccc acacacccca aggcacgcac ccacagccag cctcagggcc cacaggggca   1800
ctgtcaacac aggggtgtgc ccagaggcct acacagaagc agcgtcagta ccctcaggat   1860
```

```
ctgaggtccc aacacgtgct cgctcacaca cacggcctgt tagaattcac ctgtgtatct    1920
cacgcatatg cacacgcaca gcccccagt gggtctcttg agtcccgtgc agacacacac    1980
agccacacac actgccttgc caaaaatacc ccgtgtctcc cctgccactc acctcactcc    2040
cattccctga gccctgatcc atgcctcagc ttagactgca gaggaactac tcatttattt    2100
gggatccaag gccccaacc cacagtaccg tccccaataa actgcagccg agctcccca    2159

<210> SEQ ID NO 2
<211> LENGTH: 232
<212> TYPE: DNA
<213> ORGANISM: Homo sapiens

<400> SEQUENCE: 2
cctgcccttg acaaggacc cgatgcccaa ccccaggcct ggcaagccct cggccccttc      60 cttggcccctt ggcccatccc caggagcctc gcccagctgg agggctgcac ccaaagcctc    120
agacctgctg ggggcccggg gcccaggggg aaccttccag ggccgagatc ttcgaggcgg    180
ggcccatgcc tcctcttctt ccttgaaccc catgccacca tcgcagctgc ag           232

<210> SEQ ID NO 3
<211> LENGTH: 81
<212> TYPE: DNA
<213> ORGANISM: Homo sapiens

<400> SEQUENCE: 3
ctggtgctgg agaaggagaa gctgagtgcc atgcaggccc acctggctgg gaaaatggca     60
ctgaccaagg cttcatctgt g                                               81

<210> SEQ ID NO 4
<211> LENGTH: 9
<212> TYPE: PRT
<213> ORGANISM: Homo sapiens

<400> SEQUENCE: 4

Gln Leu Gln Leu Pro Thr Leu Pro Leu
1               5

<210> SEQ ID NO 5
<211> LENGTH: 10
<212> TYPE: PRT
<213> ORGANISM: Homo sapiens

<400> SEQUENCE: 5

Val Gln Ser Leu Glu Gln Gln Leu Val Leu
1               5                   10

<210> SEQ ID NO 6
<211> LENGTH: 105
<212> TYPE: PRT
<213> ORGANISM: Homo sapiens

<400> SEQUENCE: 6

Ile Glu Val Met Tyr Pro Pro Pro Tyr Leu Asp Asn Glu Lys Ser Asn
1               5                   10                  15

Gly Thr Ile Ile His Val Lys Gly Lys His Leu Cys Pro Ser Pro Leu
            20                  25                  30

Phe Pro Gly Pro Ser Lys Pro Phe Trp Val Leu Val Val Val Gly Gly
        35                  40                  45

Val Leu Ala Cys Tyr Ser Leu Leu Val Thr Val Ala Phe Ile Ile Phe
    50                  55                  60
```

Trp Val Arg Ser Lys Arg Ser Arg Leu Leu His Ser Asp Tyr Met Asn
65                  70                  75                  80

Met Thr Pro Arg Arg Pro Gly Pro Thr Arg Lys His Tyr Gln Pro Tyr
                85                  90                  95

Ala Pro Pro Arg Asp Phe Ala Ala Tyr
            100                 105

<210> SEQ ID NO 7
<211> LENGTH: 5148
<212> TYPE: DNA
<213> ORGANISM: Homo sapiens

<400> SEQUENCE: 7

| | | | | | |
|---|---|---|---|---|---|
| aacacagaca | aagtgctgcc | gtgacactcg | gccctccagt | gttgcggaga | ggcaagagca | 60 |
| gcgaccgcgg | cacctgtccg | cccggagctg | ggacgcgggc | gcccgggcgg | ccggacgaag | 120 |
| cgaggaggga | ccgccgaggt | gcgcgtctgt | gcggctcagc | ctggcggggg | acgcggggag | 180 |
| aatgtggact | gggtagagat | gaacgagact | tttctcagat | gttggatatt | tgcttggaaa | 240 |
| aacgtgtggg | tacgaccttg | gctgccccca | agtgtaactc | cagcactgtg | aggtttcagg | 300 |
| gattggcaga | ggggaccaag | gggaccatga | aaatggacat | ggaggatgcg | gatatgactc | 360 |
| tgtggacaga | ggctgagttt | gaagagaagt | gtacatacat | tgtgaacgac | caccccctggg | 420 |
| attctggtgc | tgatggcggt | acttcggttc | aggcggaggc | atccttacca | aggaatctgc | 480 |
| ttttcaagta | tgccaccaac | agtgaagagg | ttattggagt | gatgagtaaa | gaatacatac | 540 |
| caaagggcac | acgttttgga | cccctaatag | gtgaaatcta | caccaatgac | acagttccta | 600 |
| agaacgccaa | caggaaatat | ttttggagga | tctattccag | aggggagctt | caccacttca | 660 |
| ttgacggctt | taatgaagag | aaaagcaact | ggatgcgcta | tgtgaatcca | gcacactctc | 720 |
| cccgggagca | aaacctggct | gcgtgtcaga | acgggatgaa | catctacttc | tacaccatta | 780 |
| agcccatccc | tgccaaccag | gaacttcttg | tgtggtattg | tcgggacttt | gcagaaaggc | 840 |
| ttcactaccc | ttatcccgga | gagctgacaa | tgatgaatct | cacacaaaca | cagagcagtc | 900 |
| taaagcaacc | gagcactgag | aaaaatgaac | tctgcccaaa | gaatgtccca | agagagagt | 960 |
| acagcgtgaa | agaaatccta | aaattggact | ccaaccccctc | caaggaaaag | gacctctacc | 1020 |
| gttctaacat | ttcacccctc | acatcagaaa | aggacctcga | tgactttaga | agacgtggga | 1080 |
| gccccgaaat | gcccttctac | cctcgggtcg | tttaccccat | ccgggcccct | ctgccagaag | 1140 |
| acttttttgaa | agcttccctg | gcctacggga | tcgagagacc | cacgtacatc | actcgctccc | 1200 |
| ccattccatc | ctccaccact | ccaagcccct | ctgcaagaag | cagccccgac | caaagcctca | 1260 |
| agagctccag | ccctcacagc | agccctggga | atacggtgtc | cctgtgggc | cccggctctc | 1320 |
| aagagcaccg | ggactcctac | gcttacttga | acgcgtccta | cggcacggaa | ggtttgggct | 1380 |
| cctaccctgg | ctacgcaccc | ctgccccacc | tcccgccagc | tttcatcccc | tcgtacaacg | 1440 |
| ctcactaccc | caagttcctc | ttgccccccct | acggcatgaa | ttgtaatggc | ctgagcgctg | 1500 |
| tgagcagcat | gaatggcatc | aacaactttg | gcctcttccc | gaggctgtgc | cctgtctaca | 1560 |
| gcaatctcct | cggtggggc | agcctgcccc | accccatgct | caaccccact | tctctcccga | 1620 |
| gctcgctgcc | ctcagatgga | gcccggaggt | tgctccagcc | ggagcatccc | agggaggtgc | 1680 |
| ttgtcccggc | gccccacagt | gccttctcct | ttaccggggc | cgccgccagc | atgaaggaca | 1740 |
| aggcctgtag | ccccacaagc | gggtctccca | cggcgggaac | agccgccacg | gcagaacatg | 1800 |
| tggtgcagcc | caaagctacc | tcagcagcga | tggcagcccc | cagcagcgac | gaagccatga | 1860 |

```
atctcattaa aaacaaaaga aacatgaccg gctacaagac ccttccctac ccgctgaaga   1920
agcagaacgg caagatcaag tacgaatgca acgtttgcgc caagactttc ggccagctct   1980
ccaatctgaa ggtccacctg agagtgcaca gtggagaacg gcctttcaaa tgtcagactt   2040
gcaacaaggg cttttactcag ctcgccacc tgcagaaaca ctacctggta cacacgggag   2100
aaaagccaca tgaatgccag gtctgccaca agagatttag cagcaccagc aatctcaaga   2160
cccacctgcg actccattct ggagagaaac cataccaatg caaggtgtgc cctgccaagt   2220
tcacccagtt tgtgcacctg aaactgcaca agcgtctgca cacccgggag cggccccaca   2280
agtgctccca gtgccacaag aactacatcc atctctgtag cctcaaggtt cacctgaaag   2340
ggaactgcgc tgcggccccg gcgcctgggc tgcccttgga agatctgacc cgaatcaatg   2400
aagaaatcga gaagtttgac atcagtgaca atgctgaccg gctcgaggac gtggaggatg   2460
acatcagtgt gatctctgta gtggagaagg aaattctggc cgtggtcaga aaagagaaag   2520
aagaaactgg cctgaaagtg tctttgcaaa gaaacatggg gaatggactc ctctcctcag   2580
ggtgcagcct ttatgagtca tcagatctac ccctcatgaa gttgcctccc agcaacccac   2640
tacctctggt acctgtaaag gtcaaacaag aaacagttga accaatggat ccttaagatt   2700
ttcagaaaac acttattttg tttcttaagt tatgacttgg tgagtcaggg tgcctgtagg   2760
aagtggcttg tacataatcc cagctctgca aagctctctc gacagcaaat ggtttcccct   2820
cacctctgga attaaagaag gaactccaaa gttactgaaa tctcagggca tgaacaaggc   2880
aaaggccata tatatatata tatatatatc tgtatacata ttatatatac ttatttacac   2940
ctgtgtctat atatttgccc ctgtgtattt tgaatatttg tgtggacatg tttgcatagc   3000
cttcccatta ctaagactat tacctagtca taattatttt ttcaatgata atccttcata   3060
atttattata caatttatca ttcagaaagc aataattaaa aagtttaca atgactggaa   3120 agattccttg taatttgagt ataaatgtat ttttgtcttg tggccattct ttgtagataa   3180
tttctgcaca tctgtataag tacctaagat ttagttaaac aaatatatga cttcagtcaa   3240
cctctctctc taataatggt ttgaaaatga ggtttgggta attgccaatg ttggacagtt   3300
gatgtgttca ttcctgggat cctatcattt gaacagcatt gtacataact tggggggtatg   3360 tgtgcaggat tacccaagaa taacttaagt agaagaaaca agaaagggaa tcttgtatat   3420
ttttgttgat agttcatgtt ttttccccccag ccacaatttt accggaaggg tgacaggaag   3480
gctttaccaa cctgtctctc cctccaaaag agcagaatcc tcccaccgcc ctgccctccc   3540
caccgagtcc tgtggccatt cagagcggcc acatgacttt tgcatccatt gtattatcag   3600
aaaatgtgaa gaagaaaaaa atgccatgtt ttaaaccac tgcgaaaatt tccccaaagc   3660
ataggtggct ttgtgtgtgt gcgatttggg ggcttgagtc tgggtggtgt tttgttgttg   3720 gttttttgttg cttttttttt ttttttttt ttaatgtcaa aattgcacaa acatggtgct   3780
ctaccaggaa ggattcgagg tagataggct caggccacac tttaaaaaca aacacacaaa   3840
caacaaaaaa cgggtattct agtcatcttg gggtaaaagc gggtaatgaa cattcctatc   3900
cccaacacat caattgtatt ttttctgtaa aactcagatt ttcctcagta tttgtgtttt   3960
tacattttat ggttaattta atggaagatg aaagggcatt gcaaagttgt tcaacaacag   4020
ttacctcatt gagtgtgtcc agtagtgcag gaaatgatgt cttatctaat gatttgcttc   4080
tctagaggag aaaccgagta aatgtgctcc agcaagatag actttgtgtt attctatctt   4140
ttattctgct aagcccaaag attacatgtt ggtgttcaaa gtgtagcaaa aaatgatgta   4200
tatttataaa tctatttata ccactatatc atatgtatat atatttataa ccacttaaat   4260
```

```
tgtgagccaa gccatgtaaa agatctactt tttctaaggg caaaaaaaa aaaaaaaaa      4320
aaagaacact cctttctgag actttgctta atacttggtg acctcacaat cacgtcggta    4380
tgattgggca cccttgccta ctgtaagaga ccctaaaacc ttggtgcagt ggtggggacc    4440
acaaaacaac cagggaggaa gagatacatc attttttagt attaaggacc atctaagaca    4500
gctctatttt tttttgcca ctttatgatt atgtggtcac acccaagtca cagaaataaa     4560
aaactgactt taccgctgca attttctgt tttcctcctt actaaatact gatacattac     4620
tccaatctat tttataatta tatttgacat tttgttcaca tcaactaatg ttcacctgta    4680
gaagagaaca aatttcgaat aatccaggga aacccaagag ccttactggt cttctgtaac    4740
ttccaagact gacagctttt tatgtatcag tgtttgataa acacagtcct taactgaagg    4800
taaaccaaag catcacgttg acattagacc aaatactttt gattcccaac tactcgtttg    4860
ttctttttct ccttttgtgc tttcccatag tgagaatttt tataaagact tcttgcttct    4920
ctcaccatcc atccttctct tttctgcctc ttacatgtga atgttgagcc cacaatcaac    4980
agtggtttta ttttttcctc tactcaaagt taaaactgac caaagttact ggcttttac    5040
tttgctagaa caacaaacta tcttatgttt acatactggt ttacaatgtt atttatgtgc    5100
aaattgtcaa aatgtaaatt aaatataaat gttcatgctt taccaaaa                 5148
```

<210> SEQ ID NO 8
<211> LENGTH: 5382
<212> TYPE: DNA
<213> ORGANISM: Homo sapiens

<400> SEQUENCE: 8

```
cccttctcag gtgaagctgc tgatggagat ggagccgccg ccaccgccgc ctctgagcgc    60
ccgggtcctg gctccggccc ggcgactgcc gccgcctcag tgaccccact cccccgcac    120
tgggccgccc gggccagagt gggggacccc cgcccctcg cctccctctc cccaacact     180
gtccctctc cccaacccct cacagcctgc gcgcgcgcgg agacacctca gtctacatgg    240
ggaggacaga gaagcgcaaa gaacaagaga aaagatgcat ccatctgaga tctaaaagga   300
gacaatgaga atctctttaa aatggacata gaagactgca atggccgctc ctatgtgtct    360
gtaggaccaa tgaaggaatt attggcatgc actaaaggag atagcaagat gggtcagaca    420
cacatatgag agtcattggc aacacccggg taatgtaagg aatccacgct tcctggaagg    480
tgagtggctg ggctcacccc tgcctgccac tgagacgcag acatgcatac accacccgca    540
ctccctcgcc gtttccaagg cggcggccgc gttcgcaccc cagggtctca ccggcaaggg    600
aaggataatc tggagaggga tccctcagga gggtgtgttc cggatttctt gcctcaggcc    660
caagactcca accattttat aatggaatct ttattttgtg aaagtagcgg ggactcatct    720
ctggagaagg agttcctcgg ggccccagtg gggccctcgg tgagcaccc caacagccag    780
cactcttctc ctagccgctc actcagtgcc aactccatca aggtggagat gtacagcgat    840
gaggagtcaa gcagactgct ggggccagat gagcggctcc tggaaaagga cgacagcgtg    900
attgtggaag attcattgtc tgagcccctg ggctactgtg atgggagtgg gccagagcct    960
cactcccctg ggggcatccg gctgcccaat ggcaagctca gtgtgacgt ctgcggcatg    1020
gtctgtattg gacccaacgt gctcatggtg cacaagcgca gtcacactgg tgaaaggccc    1080
ttccattgca accagtgtgg tgcctccctt cacccagaag gggaacctgct gcgccacatc    1140
aagctgcact ctggggagaa gccctttaaa tgtcccttct gcaactatgc ctgccgccgg    1200
cgtgatgcac tcactggtca cctccgcaca cactcagtct cctctcccac agtgggcaag    1260
```

```
ccctacaagt gtaactactg tggccggagc tacaaacagc agagtaccct ggaggagcac    1320
aaggagcggt gccataacta cctacagagt ctcagcactg aagcccaagc tttggctggc    1380
caaccaggtg acgaaatacg tgacctggag atggtgccag actccatgct gcactcatcc    1440
tctgagcggc caactttcat cgatcgtctg gccaatagcc tcaccaaacg caagcgttcc    1500
acaccccaga agtttgtagg cgaaaagcag atgcgcttca gcctctcaga cctccctat    1560
gatgtgaact cgggtggcta tgaaaaggat gtggagttgg tggcacacca cagcctagag    1620
cctggctttg aagttccct ggcctttgtg ggtgcagagc atctgcgtcc cctccgcctt    1680
ccacccacca attgcatctc agaactcacg cctgtcatca gctctgtcta cacccagatg    1740
cagcccctcc ctggtcgact ggagcttcca ggatcccgag aagcaggtga gggacctgag    1800
gacctggctg atggaggtcc cctcctctac cggccccgag gcccctgac tgaccctggg    1860
gcatccccca gcaatggctg ccaggactcc acagacacag aaagcaacca cgaagatcgg    1920
gttgcggggg tggtatccct ccctcagggt ccccacccc agccacctcc caccattgtg    1980
gtgggccggc acagtcctgc ctacgccaaa gaggacccca agcacagga ggggttattg    2040
cggggcaccc caggcccctc caaggaagtg cttcgggtgg tgggcgagag tggtgagcct    2100
gtgaaggcct tcaagtgtga gcactgccgt atcctcttcc tggaccacgt catgttcact    2160
atccacatgg gctgccatgg cttcagagac ccttttgagt gcaacatctg tggttatcac    2220
agccaggacc ggtacgaatt ctcttcccac attgtccggg gggagcataa ggtgggctag    2280
caacctctcc ctctctcctc agtccaccac tccactgccc tgactacagg cattgatccc    2340
tgtccccacc atttcccaag gagttttgct ttgtagccct cactactggc cacctgacct    2400
cacacctgac cctgacccct cctcacctat tctcttcctc tatcctgacc gatgtaagca    2460
ttgtgatgaa acagatcttt tgcttatgtt tttcctttt atcttctctc atcccagcat    2520
actgagttat ttattaatta gttgatttat ttttgccttt ttaaatttta acttatatca    2580
gtcacttgcc actccccca cctcctgtcc acaactcctt ccactttag ccaattttt    2640
ctctcttaga tcttccagca gccccagggg taggaagctc ctcttagtac taagagactt    2700
caagcttctt gctttaagtc ctcacccttt acattatcta attcttcagt tttgatgctg    2760
atacctgccc ccggccctac cttagctctg tggcattata tctcctctct gggactcttc    2820
aacctggtac tccatacctc ttgtgccctc tcactttagg cagcttgcac tattcttgaa    2880
tgaatgaaga attatttcct catttggaag taggagggac tgaagaaatt ctccccaggc    2940
actgtgggac tgagagtcct attccccag taataggtca tattcccta gtaatatgag    3000
ttctcaaagc ctacattcag gatctccctc taggatgtga tagatctggt ccctctcctt    3060
gaactacccc tccacacgct ctagtccctt caacctaccg gtctattaag tggtggcttt    3120
tctctccttg gagtgcccca atttatatt tcagggggcc aaggctaggt ctgcaaccct    3180
ctgtctctga cagattggga gccacaggtg cctaattggg aaccagggca tgggaaagga    3240
gtgggtcaaa attcttctct ttctcctcca cctctcaaac ttcttcacta tagtgacctt    3300
cctaggctct caggggctcc ttcagtcccc atcctatgag aaactagtgg gttgctgcct    3360
gatgacaagg ggttgtttca gcccctcagt catgctgcct tctgctgctc cctcccagca    3420
ggattcaccc tctcattccc gggctcctgg gccctgttct taggatcagt ggcagggaga    3480
aacgggtatc tcttttctct cttctaattt tcagtataac caaaaattat cccagcatga    3540
gcacgggcac gtgcccttca ccccattcca ccctgttcc agcaagactg ggatgggtac    3600
aactgaactg gggtcttcct ttactacccc cttctacact cagctcccag acacagggta    3660
```

```
ggaggggga ctgctggcta ctgcagagac ccttggctat ttgagtaacc taggattagt    3720 gagaagggc agaaggagat acaactccac tgcaagtgga ggtttctttc tacaagagtt    3780
ttctgcccaa ggccacagcc atcccactct ctgcttcctt gagattcaaa ccaaaggctg    3840
tttttctatg tttaaagaaa aaaaaagta aaaccaaac acaacacctc acaagttgta     3900
actcttggtc cttctctctc tccttttctc ttcccttcct tccccttcca tctttctttc    3960
cacatgtcct ttccttattg gctcttttac ctcctacttt tctcactccc tatcagggat    4020
attttggggg gggatggtaa agggtgggct aaggaacaga ccctgggatt agggccttaa    4080
gggctctgag aggagtctac cttgccttct tatgggaagg gagacccctaa aaaactttct   4140 cctctttgtc ctccttttc tcccccactc tgaggtttcc ccaagagaac cagattggca     4200
gggagaagca ttgtgggca attgttcctc cttgacaatg tagcaataaa tagatgctgc    4260
caagggcaga aaatggggag gttagctcag agcagagtag tctctagaga aaggaagaat   4320
cctcaacggc accctgggt gctagctcct ttttagaatg tcagcagagc tgagattaat     4380
atctgggctt ttcctgaact attctggtta ttgagcccctt cctgttagac ctaccgcctc   4440
ccacctcttc tgtgtctgct gtgtatttgg tgacacttca taaggactag tcccttctgg   4500
ggtatcagag ccttagggtg cccccatccc cttcccagt caactgtggc acctgtaacc    4560
tcccggaaca tgaaggacta tgctctgagg ctatactctg tgcccatgag agcagagact   4620
ggaagggcaa gaccaggtgc taaggagggg agagggggca tcctgtctct tccagacca    4680 tcactgcact ttaaccaggg tcttaggtac aaaatcctac ttttcagagc cttccagctc   4740
tggaacctca acatcctca tgctctctcc cagctccttt tgcataaaaa aaaaagtaaa    4800 gaaaagaaa aaaaatca cacacactga acccacatg gagaaaagag gtgtttcctt       4860
ttatattgct attcaaaatc aataccacca acaaaatatt tctaagtaga cacttttcca   4920
gacctttgtt ttttgtgtc agtgtccaag ctgcagatag gattttgtaa tacttctggc    4980
agcttctttc cttgtgtaca taatatatat atatacatat atatatatat ttttaatcag   5040
aagttatgaa gaacaaaaag aaaaaataaa cacagaagca agtgcaatac cacctctctt   5100
ctccctctct cctagggttt cctttgtagc ctatgtttgg tgtctctttt gacctttacc   5160
ccttcacctc ctcctctctt cttctgattc ccctcccccc cttttttaaa gagttttct    5220 cctttctcaa ggggagttaa actagctttt gagacttatt gcaaagcatt ttgtatatgt   5280
aatatattgt aagtaaatat ttgtgtaacg gagatatact actgtaagtt ttgtactgta   5340
ctggctgaaa gtctgttata aataaacatg agtaatttaa ca                      5382

<210> SEQ ID NO 9
<211> LENGTH: 1464
<212> TYPE: DNA
<213> ORGANISM: Homo sapiens

<400> SEQUENCE: 9
acactgagct tgccacatcc ccaaggcggc cgaaccctcc gcaaccacca gcccaggtta      60
atccccagag gctccatgga gttccctggc ctggggtccc tggggaccctc agagcccctc    120 ccccagtttg tggatcctgc tctggtgtcc tccacaccag aatcagggt tttcttcccc      180 tctgggcctg agggcttgga tgcagcagct tcctccactg ccccgagcac agccaccgct    240
gcagctgcgg cactggccta ctacagggac gctgaggcct acagacactc cccagtcttt    300
caggtgtacc cattgctcaa ctgtatggag gggatcccag ggggctcacc atatgccggc    360
tgggcctacg gcaagacggg gctctaccct gcctcaactg tgtgtcccac ccgcgaggac    420
```

```
tctcctcccc aggccgtgga agatctggat ggaaaaggca gcaccagctt cctggagact    480
ttgaagacag agcggctgag cccagacctc ctgaccctgg gacctgcact gccttcatca    540
ctccctgtcc ccaatagtgc ttatgggggc cctgactttt ccagtacctt cttttctccc    600
accgggagcc ccctcaattc agcagcctat tcctctccca agcttcgtgg aactctcccc    660
ctgcctccct gtgaggccag ggagtgtgtg aactgcggag caacagccac tccactgtgg    720
cggagggaca ggacaggcca ctacctatgc aacgcctgcg gcctctatca aagatgaat     780 gggcagaaca ggcccctcat ccggcccaag aagcgcctga ttgtcagtaa acgggcaggt    840
actcagtgca ccaactgcca gacgaccacc acgacactgt ggcggagaaa tgccagtggg    900
gatcccgtgt gcaatgcctg cggcctctac tacaagctac accaggtgaa ccggccactg    960
accatgcgga aggatggtat tcagactcga accgcaagg catctggaaa agggaaaaag    1020
aaacggggct ccagtctggg aggcacagga gcagccgaag accagctgg tggctttatg    1080 gtggtggctg ggggcagcgg tagcgggaat tgtggggagg tggcttcagg cctgacactg    1140
ggccccccag gtactgccca tctctaccaa ggcctgggcc ctgtggtgct gtcagggcct    1200
gttagccacc tcatgccttt ccctggaccc ctactgggct cacccacggg ctccttcccc    1260
acaggcccca tgcccccac caccagcact actgtggtgg ctccgctcag ctcatgaggg    1320
cacagagcat ggcctccaga ggaggggtgg tgtccttctc ctcttgtagc cagaattctg    1380
gacaacccaa gtctctgggc cccaggcacc cctggcttg aaccttcaaa gcttttgtaa    1440
aataaaacca ccaaagtcct gaaa                                          1464

<210> SEQ ID NO 10
<211> LENGTH: 9484
<212> TYPE: DNA
<213> ORGANISM: Homo sapiens

<400> SEQUENCE: 10
gctaaccctg ctcctcgctg aagatggagg aagtaaaaac aggattaccc ttagctacag     60
atccactgcc ttagtttcca ccaccaactg cagtgcacaa acacacgtta ggcacaggaa    120
agaaagaaag acagaggaca cattaacagt aaacacaaac aaaagggtga tgggattatt    180
ttactgcatg cactgctgag cccgacattg tcacctcctc tttgaggggt tagaagaagc    240
tgagatctcc cgacagagct ggaaatggtg atgaatcttt tttaatcaaa ggacaatttc    300
ttttcattgc actttgacta tggaaacaga ggctattgat ggctatataa cgtgtgacaa    360 tgagcttttca cccgaaaggg agcactccaa tatggcaatt gacctcacct caagcacacc    420
caatggacag catgcctcac caagtcacat gacaagcaca aattcagtaa agctagaaat    480
gcagagtgat gaagagtgtg acaggaaacc cctgagccgt gaagatgaga tcagggccca    540
tgatgagggt agcagcctag aagaacccct aattgagagc agcgaggtgg ctgacaacag    600
gaaagtccag gagcttcaag gcgagggagg aatccggctt ccgaatggtg aacgcccctt    660
ccactgtaac cagtgtggag cttcttttac tcagaagggc aaccttctga cacacataaa    720
gttacactct ggagagaagc cgttcaaatg tcctttctgt agctacgcct gtagaagaag    780
ggacgccctc acaggacacc tcaggaccca ttctgtgggt aaacctcaca gtgcaacta    840 ctgtggacga agctacaagc agcgcagttc actggaggag cacaaggaac gctgccacaa    900
ctatctccag aatgtcagca tggaggctgc tgggcaggtc atgagtcacc atgtacctcc    960 tatgaagat tgtaaggaac aagagcctat tatgacaac aatatttctc tggtgccttt    1020
tgagagacct gctgtcatag agaagctcac ggggaatatg ggaaaacgta aaagctccac    1080
```

```
tccacaaaag tttgtggggg aaaagctcat gcgattcagc tacccagata ttcactttga    1140
tatgaactta acatatgaga aggaggctga gctgatgcag tctcatatga tggaccaagc    1200
catcaacaat gcaatcacct accttggagc tgaggccctt caccctctga tgcagcaccc    1260
gccaagcaca atcgctgaag tggcccccagt tataagctca gcttattctc aggtctatca    1320
tccaaatagg atagaaagac ccattagcag ggaaactgct gatagtcatg aaacaacat     1380
ggatggcccc atctctctca tcagaccaaa gagtcgaccc caggaaagag aggcctctcc    1440
cagcaatagc tgcctggatt ccactgactc agaaagcagc catgatgacc accagtccta    1500
ccaaggacac cctgccttaa atcccaagag gaaacaaagc ccagcttaca tgaaggagga    1560
tgtcaaagct ttggatacta ccaaggctcc taagggctct ctgaaggaca tctacaaggt    1620
cttcaatgga gaaggagaac agattagggc cttcaagtgt gagcactgcc gagtcctttt    1680
cctagaccat gtcatgtaca ccattcacat gggttgccat ggctaccggg acccactgga    1740
atgcaacatc tgtggctaca gaagccagga ccgttatgag ttttcatcac acattgttcg    1800
aggggagcac acattccact aggcctttc attccaaagg ggaccccctat gaagtaaaga    1860
actgcacatg aagaaatact gcacttacaa tcccacctt cctcaaatgt tgacatacct     1920
tttatttttt ttaatattat tactgttgat aattcttatt ttgtggaggc agtgtcattt    1980
gctctgccta attacgataa ggaagaaaca gaagagagaa ggggcgggaa tattgtttct    2040
ttatcacctg gcttgtttat tttgtgggaa tttaagcagc gtccatttct accaaggcat    2100
atcatgcttt gaaaaatcac ttgattcata aagattcacc taagagattc tgatttgcca    2160
ctgatattca gaattatgat ggaagacagg aaagttcaga gttttctggg taggactttg    2220
gtggtttaaa aatggtataa gtaactttat tcttgaaaga agaatgtgtt tcaaactgta    2280
aaccaatttt ttgttcttca gagatcatgg aacacaaaca cattgttatt ttcagtgata    2340
actcctaaga ggagctgagt tgttgtgggt tctatgttta cttcccctat ggaatttata    2400
attcagtatg ttttacactg taccatatag caaaacttt aaaactacagg tagttaaggg    2460
ccacctacaa tacatctgag gtcctgtgat cttattttc taaacgtaag cactgttttt     2520
ccatagttt gatgactggc attttataga cacctggca gccttacttt taacaccttt      2580
aaggaatagt attttatgt agttttcaga ataacatatg gtctaagagt ggataaaagg     2640
cagtcaataa tttctgggag ggacttctac tttcataaat ttgtttgaga ggttttcttt    2700
taaagttgta atgtgatggc agcatagtat atgtatttgt ttctaaaagt atgcttacga    2760
ttgtcacttt atcagcattt aatcagtgtt aaccagtcag cagaaaaata taattatgct    2820
aacagtaggg ggagaaaacc cacttagaaa tccctttct ggtatttctc ttttcactag     2880
ttttttttcaa gatgtgacct cccggtgttc tgtccatagt tcattcatcc tttactcttc    2940
gagtagaagg tcttaaaagt cttcctgtcg gctgtttctt tcaaaatctc ctcagagcaa    3000
ttgctaattt ggcctgaatc tggtaacttg aaccctgtaa ggttacagaa ctagggctat    3060
ttattttagc atttcttcag tagtatttac tactcttgtt gcaaagaaaa gggaatggga    3120
cttctttgta acctgtacct tggacaacag ataaaagaaa caaaaaaata agaaagttta    3180
cttttaccct tcttggagtc tagaatgtga cagaaccccc aaaggaaagt cctgcacatt    3240
tttctgtttc caaaacattt aattgtgtaa gtccttgtca gaaatgaatc tcaatccctt    3300
agtatagaat tccccttaca tggtataggt tgccatattt catgtgcaga ttttaatttc    3360
atttatgtgg gcgctctgtt ttttctttgc agtccagcca cattgagggg gaggaaccga    3420
gtgatattga ttcaagtcat tttagggga catacttgga aggcagaact tgctgcttct     3480
```

-continued

```
gtttggggag gacagacctg actgtgactg gattatctga taaccatttg tgaatactga    3540
aattctgtta ggcagtaact gataactgct ctaaaggatc attaaatagg atgctgaaat    3600
tatgtatctt aatacagtgt ggtatgagaa ttaccaagtc aagagaattg tggacataag    3660
caagtttggc cccaatactg ctcttaactc attttccagc ttactatttg ctatttaaat    3720
ggtaggcacc agctaagcac ttctaagcac taacacagct agaactaggc aaaaatggtt    3780
agaactcagc tctcttctac tagtccctgt cataattatt tttgggaaaa tgtccaaact    3840 gccccctttta aatctaaggg aatgcaccaa aacagagata tatagaatgt caaccatttc    3900
attttttttt ttctgcatgc cttggtacat agtgaacata caacctattt aaagataaag    3960 catgttttg agactcgctc acccccccccc acccaaccac tcccaaataa taattgggat    4020 gccattttt ttccttttgg atgaggtaaa taattttaag gttcacaatt ttgtctttta    4080
ctgcaattta aggaaacatt tggatgtcag tcaatatgtt cataattttg ctgtgtgcg    4140 aatttctgct ggcattatct atgaattttc ttcctactta ttttttttc agtatatgaa    4200 caatcatgta tctacctgcc ccaggatgaa actaaattta ggtggaccct aaaccttatg    4260
aagacagtgc tgaggcactt tccttttctg atttcatctt tttgggaatc tgttttattg    4320
aaggtagtta gtagttgaga gtgcatttgc tacaagcata tacttgtatc ttcctagctt    4380
catgaggaac agaaagaggt ggatatggct cagggtgtgg cagggacaat gaggacaaa    4440 gtcaattcaa atttgtgggt cagaaagaat ttttgtggac gtagtgtttt tggagaaact    4500
ctggatggtt atatgtgcat gccttttctt caaaaggaaa tacgcaaggt tgtagcatct    4560
aaaaataaac ataagagtca gacaccaaat aaatcaagtt ttacataaca gttgtatgcc    4620
cagtttgttt aggtgagatt tcacattaca gaaagtattt gaggagcatg aaaatgggtt    4680
atcttctgta ttttccagtt tggcaaaagt tcagaatttc atcacattgc tttgccctaa    4740
ttttgcccag aatttatct tagcctctct ctgacagtga tgaatcatgc tcaaaagcca    4800
ttctaattgg acctttttaa gacagggaaa gggatcagta ggcggattgg aagaaatttc    4860
aagtcattga atattccat tgagatttcc taaagggaca aaattgggaa aataagaaac    4920
tacgacttag atttggctac gtagtagaaa gtatctcccc tacatacata caggcaattg    4980
tatgtatgaa tcatagggta tatgtgtgtg tatactacac acacattctt ttaaagagaa    5040
ttcatggaaa aaaagcagt tggagtgatc agatgtattg caaaaacata cagagaattt    5100
aaatgacagt taataccaag aaattagttg ggtttacttt atcaggtcgt aataggaatc    5160
actaaagaag ttactagtgt gtctttagga ccagtggcaa ctcttaaact aaaactttgg    5220
gtccttatta tctacttaca gaacaaagtg aaacaaacaa tgattaagct gattggatat    5280
acattcaaag atatttaatg taaagttttt tggaatacga agaaaattca gaaaataaat    5340
attatcaaca gttacttatt ggcaaataga gaaagacaag aatagtttag tgagcccggt    5400
attttgtttt tatagttttt atctcagttg tacaactcac aaaaccatga agtctttggt    5460
attttataaa tgtttaacaa aatttacatc agattaaggc atttagatga aaattattat    5520
gttctcacta tcttccaaat tttatttcat cctatctcca aaatgatttc ttagggtaca    5580
aaaagagcag acgggctgt aaaaatacaa gcaaaaaact gtgtgcccct agtttcaggc    5640
agaacttaaa ctgtcagagg tactagctac atgatttgtt ttttaacttt ggattgttca    5700
cgtccaaaaa tggataaatt acatttgtgt ttatcatcag ttgcatttta tgtattattt    5760
taataaatac tatctgaatg aagactattc taaaccagaa aattccccaa atccaaaaga    5820
aaaaaaaagt gggaagaggt gaaattgaag tttgtgtata tgaaagttat cttagacata    5880
```

```
tttttaattc tccagtttct gcaaataat taaaatatac agtaactggt ctcctaaatc    5940
ctgaatttaa tgtattaaat acttatgttc tttatattgg tgccttttta aaatgcattg    6000
agagtgttgg ttagctgttg cagctgtaca acacttttaa tatgcattt  taaaaatcac    6060 ttaaaattga gtactatata attcatctct gcattttag  tgcaaatctt tagagcaatt    6120
tctaatagag aaattttcag ctcagctgtt aaaaggaaaa ggaaactttg aaactagact    6180
ttactacctt tttagtttca tagtatttct gaatatgatt acaagattat gcaggtaaaa    6240
tatagagtga aacttacct  gtgaattgaa ttataatttg tgttttgtt  ttgtttttaa    6300 ggaagaataa gttctgtatc aaacaagaat ttattagata attttttggt caataaaata    6360
cagtattcat ttggattttc atctccagac tagtattgtt ctagtcttgg aatctgtatt    6420
ttctaatctg ttagaaaata gagattgaaa attgatggaa taatgtgaaa aagcaggtaa    6480
ttaattctcc ttgaacaaag caaaactgaa cagtcatatc acattgctat tctccaaagc    6540
ataatctcaa atggtttcat atcatggttg tgtattactt gcaatgggtg tgttaggata    6600
tgacagcttt ttaaaaaaat gagctgctgg ttatacaaag caaatggcat atgaccaaga    6660
agctgtgata tgctagtgtt tctttttatc atagtgtatt actaggccaa ataatgacac    6720
cttgaatatt tttacattta ttgcagaaac cttaaacttt ggaatttcca taaggttttt    6780
atgtaatatt ctatttctag ctttttagtt ttatcttgct gtactgtaag tttgaggata    6840
tttttcacct gcactcttag gaataagttc ataattctgt ttatgggct  ttcctcccat    6900 aacactgcat ttgtatattt tctgtataaa atatgtgttg tgtattaacc tttatcccat    6960
acagagagtg gtacatgaat gactagtttt ctaagatgtc ctttttattg tgaataaaat    7020
ataaaagtta aaggccctct gctaagtcac ataaagtaca gcatataagt tcatataggt    7080
acaaataaat gagtttgcag tgaattgggc cttcaaatta cctcaagtga cagatagtaa    7140
gaaaagcttc ttgagcaggt ggaggtcact gaatccccta ctatgcactt accaagattt    7200
tacttacttt aatttactgg aaattgattt ttaaaaaaat gactcacactg taacaaggga    7260 agggatctgg gttttttgt  tgttttattc ttgttttttt taagtagttc aaattctgaa    7320
actgtgattt aaaaatttt  tacagtcaag cattctgatt ttgaacataa ctcccttccc    7380
tttctgtgta acaaaggtct ctctgttatc tcttaaattt tgttacatct ccctcagcct    7440 cttttctttgt ccgtctccct tctgtcattg tctatggatg tttacctctc tgttctccta    7500
aaagtttgaa gattaggtca actcttattt ctagttcatt ggtaatttaa tcttaattt     7560 tttttcgtga ttttgttgg  ttgtataatc tgctgacgta tttttatact caagtgtagt    7620
tttctattaa aaagaaaagt ggttggatta aaaatagtaa gctatgtaac cctcatgtta    7680
ctttcacttt caaatattgg gtacctaaaa cattacttca gagattatgt aatcctatta    7740
tagtatgttt gctttccttt attgttggat tttacattct gatttggctt tcctccaaaa    7800
aatgtatatc atgaaagact agacagttat ttgcaagtgt ttagaaaggt gttaaaaatg    7860
taaagcaaag agtcttaact ttctcctaat tgggagaaaa atgctttaac attactataa    7920
taatattcca ggtttggagg gggtctccag gccccatatt tgctgttaat agttggacct    7980
tttagaccat gtgttatttg caatcccaga atgattgctt ctgctattag ttaaaaagat    8040
actattcttt tctttctgta caagtgcaat actccccttg aagtcttaaa aactatggtg    8100 atttttttt  cttttctgac ctattcttcc tttagctaat gacaaaaaga aactcataaa    8160
agtcatagta tgttaaagga cacaacaagc aaagagaaaa acactccaca atcaaaagat    8220
tacagaatgt ggaaaccact agtctgatct catggtatct ttatttaagc taaatttcca    8280
```

-continued

```
tggaaattag taatcttttg cttgaaaaat gtgtcctaaa gttgaacttt ttacagattg      8340
aatcttctta gaccctcgcc caatgctcta aattaagaac ctaatactta atatttttat      8400
tttacttctc cccttttaga aataaacttt taaataaaag caaagcactt agctgagttt      8460
taaacactta catatcacct attggagaaa ttttttttaa aaatatttgg agcagtcctg      8520
ttttcataca aatttaagta agaggtattt ttcttataca tatttatatg tagtgtgcta      8580 atttttctttt tttataccctg tgtccctgta gtaaaactgc tgtaatataa atacatgttt      8640
tgttaaaaga taacatttct ttggcatttc ttttaaaggc agttactgca tttctgcatt      8700
tgtacagtat gtgtcttggc cattttagat attctttctt taacaatacc aaaggtaatt      8760
agactatttt aaagactaat tgcttgacag tttctagggt attttgtgtt ttagaagcaa      8820
aaaaagaaaa aaaaataggt caaaccagta aacctcattt ttttttcaaac taataatttg      8880 gggaaataaa aactattgtt taaaaagaa atatatatat atatatataa atatatatgt      8940
aaagttaaaa ttccatacct tgtatgtcag gtttgctaag tgtaatgtag tttttttaag      9000
gctcaaatac catacctcag aaaatgaggt ttactatgga aatactgaaa cagtctttgc      9060
agctgtgtga caagtcactc tactacatac tgatttggag acctccgcta aatagtttta      9120
tcactgcaga ctaaaatgtg ggacttgtat cttctttgtt tttaatgcac acacatacat      9180
gttctgtgca tgtatgtggt tactgtgtat atgtgtatga gtgttgtata tgcatgtgtg      9240
agtgtgtgtc tgtatgtgtg tacaactaaa gaagctgcag aaactttgta atactttgtg      9300
aaaaggatta tattataaag gtttgtactg tctgagtgca cagctactgg aataaattta      9360
gggaatctca ggaacaagca tataatttgt ccaagattta tttcttctca gaagtgtaag      9420
tgcagttttt aattctgtat attatttaat attttaccaa taaaataaac ttctgacata      9480
aaaa                                                                 9484
```

<210> SEQ ID NO 11
<211> LENGTH: 3083
<212> TYPE: DNA
<213> ORGANISM: Homo sapiens

<400> SEQUENCE: 11

```
gaacactgag ctgcctggcg ccgtcttgat actttcagaa agaatgcatt ccctgtaaaa       60
aaaaaaaaaa aatactgaga gagggagaga gagagagaag aagagagaga gacgagggga      120
gagcgagaca gagcgagcaa cgcaatctga ccgagcaggt cgtacgccgc cgcctcctcc      180
tcctctctgc tcttcgctac ccaggtgacc cgaggaggga ctccgcctcc gagcggctga      240 ggacccccggt gcagaggagc ctggctcgca gaattgcaga gtcgtcgccc ttttttacaa      300
cctggtcccg ttttattctg ccgtacccag ttttttggatt tttgtcttcc ccttcttctc      360
tttgctaaac gaccccctcca agataatttt taaaaaacct tctcctttgc tcacctttgc      420
ttcccagcct tccatccccc ccaccgaaag caaatcattc aacgaccccc gaccctccga      480
cggcaggagc ccccgacct cccaggcgga ccgccctccc tccccgcgcg cgggttccgg       540
gcccggcgag agggcgcgag cacagccgag gccatggagg tgacggcgga ccagccgcgc      600
tgggtgagcc accaccaccc cgccgtgctc aacgggcagc cccgacac gcaccacccg       660 ggcctcagcc actcctacat ggacgcggcg cagtacccgc tgccggagga ggtggatgtg      720 ctttttttaaca tcgacggtca aggcaaccac gtcccgccct actacggaaa ctcggtcagg      780
gccacggtgc agaggtaccc tccgacccac cacgggagca ggtgtgccg cccgcctctg       840 cttcatggat ccctaccctg ctggacggc ggcaaagccc tgggcagcca ccacaccgcc       900
```

| | |
|---|---|
| tcccctgga atctcagccc cttctccaag acgtccatcc accacggctc cccggggccc | 960 |
| ctctccgtct accccccggc ctcgtcctcc tccttgtcgg ggggccacgc cagcccgcac | 1020 |
| ctcttcacct tcccgcccac cccgccgaag gacgtctccc cggacccatc gctgtccacc | 1080 |
| ccaggctcgg ccggctcggc ccggcaggac gagaaagagt gcctcaagta ccaggtgccc | 1140 |
| ctgcccgaca gcatgaagct ggagtcgtcc cactcccgtg gcagcatgac cgccctgggt | 1200 |
| ggagcctcct cgtcgaccca ccaccccatc accacctacc cgccctacgt gcccgagtac | 1260 |
| agctccggac tcttcccccc cagcagcctg ctgggcggct ccccaccgg cttcggatgc | 1320 |
| aagtccaggc ccaaggcccg gtccagcaca gaaggcaggg agtgtgtgaa ctgtggggca | 1380 |
| acctcgaccc cactgtggcg gcgagatggc acgggacact acctgtgcaa cgcctgcggg | 1440 |
| ctctatcaca aaatgaacgg acagaaccgg cccctcatta gcccaagcg aaggctgtct | 1500 |
| gcagccagga gagcagggac gtcctgtgcg aactgtcaga ccaccacaac cacactctgg | 1560 |
| aggaggaatg ccaatgggga ccctgtctgc aatgcctgtg gctctacta caagcttcac | 1620 |
| aatattaaca gaccctgac tatgaagaag aaggcatcc agaccagaaa ccgaaaaatg | 1680 |
| tctagcaaat ccaaaaagtg caaaaaagtg catgactcac tggaggactt ccccaagaac | 1740 |
| agctcgttta accggccgc cctctccaga cacatgtcct ccctgagcca catctcgccc | 1800 |
| ttcagccact ccagccacat gctgaccacg cccacgccga tgcacccgcc atccagcctg | 1860 |
| tcctttggac acaccaccc ctccagcatg gtcaccgcca tgggttagag ccctgctcga | 1920 |
| tgctcacagg gccccagcg agagtccctg cagtccctt cgacttgcat ttttgcagga | 1980 |
| gcagtatcat gaagcctaaa cgcgatggat atatgttttt gaaggcagaa agcaaaatta | 2040 |
| tgtttgccac tttgcaaagg agctcactgt ggtgtctgtg ttccaaccac tgaatctgga | 2100 |
| ccccatctgt gaataagcca ttctgactca tatccctat ttaacagggt ctctagtgct | 2160 |
| gtgaaaaaaa aaatgctgaa cattgcatat aacttatatt gtaagaaata ctgtacaatg | 2220 |
| actttattgc atctgggtag ctgtaaggca tgaaggatgc caagaagttt aaggaatatg | 2280 |
| ggagaaatag tgtggaaatt aagaagaaac taggtctgat attcaaatgg acaaactgcc | 2340 |
| agtttttgttt cctttcactg gccacagttg tttgatgcat taaagaaaa taaaaaaaag | 2400 |
| aaaaaagaga aagaaaaaa aaagaaaaaa gttgtaggcg aatcatttgt tcaaagctgt | 2460 |
| tggcctctgc aaaggaaata ccagttctgg gcaatcagtg ttaccgttca ccagttgccg | 2520 |
| ttgagggttt cagagagcct ttttctaggc ctacatgctt tgtgaacaag tccctgtaat | 2580 |
| tgttgtttgt atgtataatt caaagcacca aaataagaaa agatgtagat ttatttcatc | 2640 |
| atattataca gaccgaactg ttgtataaat ttatttactg ctagtcttaa gaactgcttt | 2700 |
| ctttcgtttg tttgtttcaa tattttcctt ctctctcaat ttttggttga ataaactaga | 2760 |
| ttacattcag ttggcctaag gtggttgtgc tcggagggtt tcttgtttct tttccatttt | 2820 |
| gtttttggat gatatttatt aaatagcttc taagagtccg gcggcatctg tcttgtccct | 2880 |
| attcctgcag cctgtgctga gggtagcagt gtatgagcta ccagcgtgca tgtcagcgac | 2940 |
| cctggcccga caggccacgt cctgcaatcg gcccggctgc ctcttcgccc tgtcgtgttc | 3000 |
| tgtgttagtg atcactgcct ttaatacagt ctgttggaat aatattataa gcataataat | 3060 |
| aaagtgaaaa tattttaaaa cta | 3083 |

<210> SEQ ID NO 12
<211> LENGTH: 7449
<212> TYPE: DNA
<213> ORGANISM: Homo sapiens

<400> SEQUENCE: 12

```
gcgttgcctc tggagtaagc cggatcgcgg agccgcgccg actccgccga gccgggagcc      60
gggaggcgcg cagctcccgg gtcgctccga ggctcctcgg ccagggcagc ccgcgggca      120
cgcggtagag aagacggcgt cccctcggct gctggtcgat acaaacagat ccccctttcc    180
aaacacgcgc caagtccccg tgccctccag atgcagagag aggctgcgtt cagactgggg    240
cactgccatc ccctccgcat catggggtct gtggaccaag aagagccgaa tgcacataag    300
gtcgccagcc caccctccgg acccgcatac cccgatgatg tcctggacta tggcctcaag    360
ccatacagcc cccttgctag tctctctggc gagcccccg gccgattcgg agagccggat     420
agggtagggc cgcagaagtt tctgagcgcg gccaagccag caggggcctc gggcctgagc    480
cctcggatcg agatcactcc gtcccacgaa ctgatccagg cagtggggcc cctccgcatg    540
agagacgcgg gcctcctggt ggagcagccg cccctggccg gggtggccgc cagcccgagg    600
ttcaccctgc ccgtgcccgg cttcgagggc taccgcgagc cgctttgctt gagcccgct    660
agcagcggct cctctgccag cttcatttct gacaccttct cccctacac ctcgccctgc    720
gtctcgccca ataacggcgg gcccgacgac ctgtgtccgc agtttcaaaa catccctgct    780
cattattccc ccagaacctc gccaataatg tcacctcgaa ccagcctcgc cgaggacagc    840
tgcctgggcc gccactcgcc cgtgccccgt ccggcctccc gctcctcatc gcctggtgcc    900
aagcggaggc attcgtgcgc cgaggccttg gttgccctgc cgcccggagc ctcaccccag    960
cgctcccgga gccctcgcc gcagccctca tctcacgtgg caccccagga ccacggctcc    1020
ccggctgggt accccctgt ggctggctct gccgtgatca tggatgccct gaacagcctc    1080
gccacggact cgccttgtgg gatccccccc aagatgtgga agaccagccc tgaccctcg   1140
ccggtgtctg ccgccccatc caaggccggc ctgcctcgcc acatctaccc ggccgtggag    1200
ttcctggggc cctgcgagca gggcgagagg agaaactcgg ctccagaatc catcctgctg    1260
gttccgccca cttggcccaa gccgctggtg cctgccattc ccatctgcag catcccagtg    1320
actgcatccc tccctccact tgagtggccg ctgtccagtc agtcaggctc ttacgagctg    1380
cggatcgagg tgcagcccaa gccacatcac cgggcccact atgagacaga aggcagccga    1440
ggggctgtca agctccaac tggaggccac cctgtggttc agctccatgg ctacatggaa    1500
aacaagcctc tgggacttca gatcttcatt gggacagctg atgagcggat ccttaagccg    1560
cacgccttct accaggtgca ccgaatcacg gggaaaactg tcaccaccac cagctatgag    1620
aagatagtgg gcaacaccaa agtcctggag ataccccttgg agcccaaaaa caacatgagg    1680
gcaaccatcg actgtgcggg gatcttgaag cttagaaacg ccgacattga gctgcggaaa    1740
ggcgagacgg acattggaag aaagaacacg cgggtgagac tggttttccg agttcacatc    1800
ccagagtcca gtggcagaat cgtctctttta cagactgcat ctaaccccat cgagtgctcc    1860
cagcgatctg ctcacgagct gcccatggtt gaaagacaag acacagacag ctgcctggtc    1920
tatggcggcc agcaaatgat cctcacgggg cagaactta catccgagtc caaagttgtg    1980
tttactgaga agaccacaga tggacagcaa atttgggaga tggaagccac ggtggataag    2040
gacaagagcc agcccaacat gcttttttgtt gagatccctg aatatcggaa caagcatatc    2100
cgcacacctg taaaagtgaa cttctacgtc atcaatggga agagaaaacg aagtcagcct    2160
cagcacttta cctaccaccc agtcccagcc atcaagacgg agcccaccgga tgaatatgac    2220
cccactctga tctgcagccc cacccatgga ggcctgggga gccagcctta ctaccccag    2280
cacccgatgg tggccgagtc cccctcctgc ctcgtggcca ccatggctcc ctgccagcag    2340
```

```
ttccgcacgg ggctctcatc ccctgacgcc cgctaccagc aacagaaccc agcggccgta    2400
ctctaccagc ggagcaagag cctgagcccc agcctgctgg gctatcagca gccggccctc    2460
atggccgccc cgctgtccct tgcggacgct caccgctctg tgctggtgca cgccggctcc    2520
cagggccaga gctcagccct gctccacccc tctccgacca accagcaggc ctcgcctgtg    2580
atccactact cacccaccaa ccagcagctg cgctgcggaa gccaccagga gttccagcac    2640
atcatgtact gcgagaattt cgcaccaggc accaccagac ctggcccgcc ccggtcagt    2700 caaggtcaga ggctgagccc gggttcctac cccacagtca ttcagcagca gaatgccacg    2760
agccaaagag ccgccaaaaa cggacccccg gtcagtgacc aaaaggaagt attacctgcg    2820
ggggtgacca ttaaacagga gcagaacttg gaccagacct acttggatga tgagctgata    2880
gacacacacc ttagctggat acaaaacata ttatgaaaca gaatgactgt gatctttgat    2940
ccgagaaatc aaagttaaag ttaatgaaat tatcaggaag gagttttcag gacctcctgc    3000
cagaaatcag acgtaaaaga agccattata gcaagacacc ttctgtatct gacccctcgg    3060
agccctccac agccctcac cttctgtctc ctttcatgtt catctcccag cccggagtcc    3120
acacgcggat caatgtatgg gcactaagcg gactctcact taaggagctc gccacctccc    3180
tctaaacacc agagagaact cttctttttcg gtttatgttt taaatcccag agagcatcct    3240
ggttgatctt aatggtgttc cgtccaaata gtaagcacct gctgaccaaa gcacattct    3300 acatgagaca ggacactgga actcctctga aacagagtg actggagctt gggggggatgg    3360 acggggggaca gaagatgtgg gcactgtgat taaaccccag cccttgcgtt cgtttttcca    3420
ggtcacagat acagctcctg tacctttgga aggcaaggag ttctcagagc aaccaaagga    3480
acgtgaccca agagcccagc ttacaggctg aagaaaccca aaaccctcga tagagacaga    3540
aactgaactg tcagtcctta gagctcgccc agtccatgcc acaactgggc cacagctaaa    3600
gctttatttt tgaattctca ttccaaaacc aaactgtctt gcccagacaa gatcacctgt    3660
taagacttct tggcgttaag ttatgacatg tatacgcgtt tgttattatt atttttctg    3720 ctttaaaagg ctgaccaggg cacctagccc tggagctgtc ttggcgagct gttctttaac    3780
ccctgcagca cgcagtcctg ctaacacaat ttccatagac ttgggggggct gacccaggct    3840 gcagagagca agcacctgtc tgctgcagct gtacaacctg gatgctttgc aaggttccgg    3900
cttgctttct tcctagcagc cagagtgctt ttccgtaaag cggtggagaa tctcaagcat    3960
gtgcatttaa ttgaggaata gcagaagggc taaagcaacc aagaaaagaa gtgtgggtat    4020
ttttgttaag taaaacagcc caagtgcttc tggaggtggg tttctaccaa gatagaggaa    4080
aagggctgaa ttccctctaa gtgggacagc cgagctcagg atgtgcttcc cagcttcact    4140
ggttaatttg acctgaacct atttaaagat cccttctgcc cctgaagacc tatccgcact    4200
caaattctaa catgaagaaa tctactcgaa tgcatccttt actttgaatg agctctattc    4260
ggttgcatgt tatatgtgat ttccttcctc ccaactgttt ccactgagcg cacccagtct    4320
cccctagtct tcctctgtgg gtgtgatttt tgtgatttt acaaacaaaa cccttgaagt    4380
tcttggcaga tgtgtttgtt tctgtttgca tgtactgcag ataccccagg acaagcgggg    4440
gattcatttt tcagccattc agttgttttcc tcaataatcc gcagcaaagt gaaaatattc    4500
ttagcactca gactgtactt agagtgtttt ctcagtccag tctgtacagt ctgtaggcag    4560
aaggcctcag aagaaagtca tggccactca gtgccactg tgggctttgt aagtcctggc    4620
tctcccgtca aggttaccca gaggtaaaag cttcctggga gtggggccag gtgtgtttgg    4680
cactccagat agaaggcaaa atgctcagat tcgggcctgt gcacttgtat gcaacctgtc    4740
```

```
ggtcgatacc tagcatttat ttttccctga caatgaacga cctttccctc acccacccta    4800
agctcaaaga gtttagcaaa attctctttt aaataaacag aatgccagta agaggttgac    4860
ccctaccatg gaacttctgg gatgctaaat acttcctcat gaacaaaata agttccttat    4920
tataagttcc ttatactagc agcttcacct aaagaatttt ctctccagca atattgactt    4980
cactggggaa aagccaagag tgtgtggtga gtgatttgtt ctcactcgac ctggctagga    5040
ctggctagga gctgtttttt gtacatgagg gaatttgggc tttcctcagt tatctgaatg    5100
ttttacccaa gtgccttcct gctattgtag caaagtagct cagcttcctt gtccacaggg    5160
tgaaaaagga ctaatgcatt ttccatcagt tttctaacta tgttagcaaa aacggcctcc    5220
tggtagctca acctcctgta cgcgtgtgtg tgtgtaatac acacacaaat aaacccctct    5280 gttttttctaa gacatcttag ctggatatta taggaagcac tttcataaac aactgtaaca    5340
aatcgcaaag gaaagagaaa caaaagcatt agatttgaga cataaacagg caagagaaag    5400
tgtattagga actgacagct atcaaggaag ttttgtcagt tacaaatgct aggaggaaat    5460
tttgccaaga aggatggctc atgaaatatt tccagtacgg gaagaggcaa taagatcctc    5520
taagagaatg agaaagtagg ggtgtctaaa tggtaaagat gggtgtgttg cacgtgtgtt    5580
agaaggatct cagttgagtg aaggtttgca ctgctacatc taagttaatg taaatatgta    5640
gcactctgac aggtctaccg tgttgctgaa tgtagtatat ttccaaagtt tgcaagtctt    5700
cctgtattgt acaagatgc tgctgcttga taatatgtat agcaatccag attagtatgt    5760
tattaaattt tattttctta cctgtatttt tatgctttt acctgtcctc aaaatattac     5820
acccctgttg gaattagatt tatatttata aatggtcaga aatctttta agtgtctctt     5880 tttacacata ggttgatttt tttttcttaa gagaaatgat gtattcttga aacatttgtt     5940
actcattcca ggaaacaaaa acccatataa taaaaccccc actcagagcc tgttagtcac    6000
ctctctagaa gatggcatct caggagaagg aatggctttg tggaagaagg aatcacctt     6060 ttcttgctca agaattatgc tgacttcagc cctgagcctg gatctggtca ctgagaatca    6120
tcaagtgtct agatcctccc cccaaaataa ctaatttagt aggtgatttt gatttaaaa     6180 aattgacacc aaaaccctgc ctgcattgta atggaattcg aaaagaattc atgttcacag    6240
aactcaacgt tcaggctaat atttacagaa gggaccaaat ctaaatcctg gtagataact    6300
cctgtatgct ttatccaaag gacacccaca gttttccagc atagatataa ccaaggatga    6360
attgattcct tcaaagaact gggaggcacg gatattgcat ttttttgttta catccagtag    6420 ccaagacgcc tcagtgagcc agtcttgggc agaggctgtc acatttaggc agattggaag    6480
ttggtatgtt ctaattctca ctctggacta cagtgaggct gaatttatca tgtcaaaaaa    6540
aaaaaaaaaa aaagaccttt ccaagtgctt tctattgctc agaattgaaa gaatgttttc    6600
atttcaagtt tacaagaggc atggatggag ttgtgacgtt cttgacaagc tgggctaacc    6660
tttcccgaac ttgtttcccg gaggcaaggt gctcggtgac ccagcgcatc ttaaccttgg    6720
gtctcctagg ctcgaggcta gggcattacg tttcgtggaa ccaaagcagc caattgcata    6780
gcaagtattt tcctgcattc caattaaatg cttaagaaaa agcagcatcc tataaaattg    6840
tgatcataaa catccatttc cctcagcttt tgtgagtgcc ttgacttaca gccaacatca    6900
ctgtttaact cagtctgttt aaaaacaaac ttttctggtg gttgataaca gagagttgct    6960
ccctgagcca tcagggtcct gggagctgga agtgaaaggg ttattaacat tctaccttta    7020
tgcagctgtt ggctgaccag aataaactcc ctgctgagtt caagctttga atggaatgga    7080
tgcaaatgat gttgtttcca ttagagcagg tgctcacagc attctgattg gcctgagcag    7140
```

| | |
|---|---:|
| accgaggcta tggctgttgg acaagcttta gcatcctgga catcttgtca agaacctca | 7200 |
| ctcacccctc tggcctctac agccctcaga ggagagaaaa ccaattctcc aacaaacagg | 7260 |
| tctctccaac atggtggtgc tggcaggctt aggtttagaa atcctgact gttaaaggcg | 7320 |
| tttgaataca tcacattcct atgcaaatgt ttttaatctc cagtttaatg tagtttattt | 7380 |
| ttcctatatg taaagtattt ttatacggct tgtatcatga tagtttagca ataaaacagt | 7440 |
| tggaagcaa | 7449 |

<210> SEQ ID NO 13
<211> LENGTH: 164
<212> TYPE: PRT
<213> ORGANISM: Homo sapiens

<400> SEQUENCE: 13

```
Met Lys Trp Lys Ala Leu Phe Thr Ala Ala Ile Leu Gln Ala Gln Leu
1               5                   10                  15

Pro Ile Thr Glu Ala Gln Ser Phe Gly Leu Leu Asp Pro Lys Leu Cys
            20                  25                  30

Tyr Leu Leu Asp Gly Ile Leu Phe Ile Tyr Gly Val Ile Leu Thr Ala
        35                  40                  45

Leu Phe Leu Arg Val Lys Phe Ser Arg Ser Ala Asp Ala Pro Ala Tyr
    50                  55                  60

Gln Gln Gly Gln Asn Gln Leu Tyr Asn Glu Leu Asn Leu Gly Arg Arg
65                  70                  75                  80

Glu Glu Tyr Asp Val Leu Asp Lys Arg Arg Gly Arg Asp Pro Glu Met
                85                  90                  95

Gly Gly Lys Pro Gln Arg Arg Lys Asn Pro Gln Glu Gly Leu Tyr Asn
            100                 105                 110

Glu Leu Gln Lys Asp Lys Met Ala Glu Ala Tyr Ser Glu Ile Gly Met
        115                 120                 125

Lys Gly Glu Arg Arg Arg Gly Lys Gly His Asp Gly Leu Tyr Gln Gly
    130                 135                 140

Leu Ser Thr Ala Thr Lys Asp Thr Tyr Asp Ala Leu His Met Gln Ala
145                 150                 155                 160

Leu Pro Pro Arg
```

<210> SEQ ID NO 14
<211> LENGTH: 13013
<212> TYPE: DNA
<213> ORGANISM: Homo sapiens

<400> SEQUENCE: 14

| | |
|---|---:|
| gagcatgctc ccgctgcagt taactagccc aacctatttc tttaattcag cccatccctt | 60 |
| cgtttccctt aagggatact tttagttaat ttaatatcta tagaaacaat gctaatgact | 120 |
| ggtttgctgt taataaatat gtgggtaaat ctctgttcag ggttctcagc tctgaaggtt | 180 |
| gtaagatccc tgatttccca cttcacacct ctatatttcc ttttttttt tttttttttt | 240 |
| tgagacagag tctcactctc gcccaggctg gagtgcagtg gcacgatctc tgctcactgc | 300 |
| aagctccgcc tcccgggttc acgccattct cccgcctcag ccttccgagt agctgggact | 360 |
| acaggcgccc gccactacgc ccggctaatt ttttgtattt ttagtagaga cggggtttca | 420 |
| ccgtgttagc caggatggtc ttgatctcct gacttcgtga tccgcctgcc tcggcctccg | 480 |
| aaagtgctgg gattacaagc gtgagccacc gcgcccggcc tcacacctct atattctgt | 540 |
| gtgtgtgtct ttaattcctc tagcactgct gggttagggt ctccctgacc gagctggtct | 600 |

```
cggcagataa ggtttcacca tgttggccag gctggtctca aactcctgac ttcaggggat    660
ccccgcccca gcctcccaaa gagctgggat tacgggcatg agtcaccgtg cccagccaat    720
tttcttttgt tttttctttt gagacaggat ctcactctgt cacccaggct tgaatgcagt    780
ggtaccatct cggctcactg cagcctcaat cttctgggct caaatgatcc tcccaccttc    840
gcctcccgag cagctggggc tacaagtgca cactaccaag cccagctaat tttttttttt    900
tttttttttt tttgagacag agtcttgctg tgtccctcac ccaggttgga gagcagtggt    960
tcgatcttgg ctcactacaa cctctgcctc ccgtgttcaa gcaattctcg tgcctcagcc   1020
tcctcagtag ctgggattac aggcacgtgc caccatgccc agttaatttt tgtattttta   1080
atagagacgg ggtttcgcca tgttgaccag gctggtcttg aaccctgac tcagcctcc    1140
caaagtgctg agattacagg tgtgagccga catgctaggc ctatacattt caaaattatg   1200
ttgctatgtt cataaagatg tatatatggt aacttgtacc ttcaatcaac atgaaatacc   1260
cttctttgtc cttttaatgc ctttatgata aattctgtct catattaata ttgctacata   1320
tgctttcttt ccataaacat ttccataaac ataaaaatgg ctggtaagtc attttccttt   1380
tttttaaaaa aattttttgtt tttagaggc aggagctcat tctgtctccc aggttggagt   1440
acaatggttc aatcatagct catagtttac tgcagcctcg aactcctggg ttcaagggat   1500
cttaccacct ccgtcttccg agcagctggg actacaggtg caagtcacca cgcctggtta   1560
attttttaa attttttgta gagacaaggt cacaatatgt ttcccagcct ggtcttgaac   1620
tcctggcctc aagcaatcct cctgccttga gaaatatagt aaacaaaaaa tgtgaaataa   1680
catggcagaa ataagtccaa ataaataaat aatcaaaaat aaatacaaat gatttatatt   1740
ctcttcttaa aagagagctc tgagaaaccc caaagccagc tatatgttgt ttataaagag   1800
acatacataa aacaaaacag catgattaag aagataatat aacccattca catttatgtt   1860
ttattattta tatatttgga cttattcctg ccatgttatt ttctgttttc tgcttaccag   1920
tgtacagtat ttttctgttt tcccttttct ggaatgccta tttatttctg ttcctgtttt   1980
gtccacccctt tcctgactga ttctttctga ataatgactt tttttttttt tttttttttt   2040
tttgagaaag tctcactctg ttgaccaggc tggagtgcaa tggcacaatc ttggctaatt   2100
gcaacctctg cctcccaggt tcaagacatt atcctgcctc agcctcccca gtagctgaga   2160
ttacaggcgc ccccaccat gtccggctaa tttttgtatt tttagtagag actgggtttc   2220
accatgttgg ccaggctggt ctcgaactcc tgatctcagg tgatctgccc acctcggcct   2280
cccaaagtgc tgggattaca ggggtgagcc accgcgtttg gcctcaaaga ccgagaactt   2340
tgtaatttat atatttata gctcttatca caggtgtcta gtaaatattt ttaaacactt   2400
atggcacctg atgcaagaat taccaggttc attttataga gaggatatga aactgtccaa   2460
gggtttggac tcacatgttc aagactgcat ggacagcaat ctgtagtggg tcaaattatt   2520
gtttttagta tgatttaaag tgtttgtcaa aaatataaaa gttttgaaaa caagctgggg   2580
aagtgaattt caatatcgca ttaactaaga tcaaagtgca attcatcaac cttttttccc   2640
catcccgcac cctgtgcttt ctctactcag ttactcacta caccctgctg gactaaaagg   2700
gtcctccagc attttctttc ttacacagtg aaagacattc tcttggcatt aataaatgtt   2760
cacttaataa ataaaaaggg ccgggctctg tggttcctgc ctgcaatccc agcagtttgg   2820
gaggccaagg caagaggatc gcttgagcct aggagttcca gcctaggcaa cgtggcgaaa   2880
cccagtctca aaaaaaaaa aaaggaaaaa aaaggcatca aaaataaaa cgtaacaggt   2940
ggcatgacat gacatgactt ttctaacagc ctcttacagc tttccaaggt ctttaatat   3000
```

```
gaagctatag gtctcggcta aagacacct ccagacttct cccaaaacat ttcagaggcc    3060
cggagtaagt ctccccacat ctgaaggcac atcagaaccc aggtggccca agctgatgag    3120
agttaaacag gaagttggtt tcttggtccg gcagagactc caatcacccc cacctctttt    3180
ccaacccaca ggacagcacg tgctcaggag gctctggagt tgggacagcc cagttaaaaa    3240
aaaaaaaatc attgatttcc ctcccaacga agagggagaa aacacgttag gagactcgtg    3300
gcccagtcct ggcaaaaacc aaaactatgt cccctttagag ggcttagata tcaagagatg    3360
gacttgcttt tagttctttt tcccatcctg ttccctccct accaaaataa aattgaccag    3420
ctaatccgac ttaataacac taaagaatta cttaggaacc tgctatctta acatttcact    3480
ttttgcatat cctccaaata ccaggtagca gtcttactac tgtttgcacc cctagaacct    3540
ggaatagtgc tgcccgcaga ggaggaagca ataattactt gttagagaag gtattgctgt    3600
gcatttctgg ggaatttcac attttgtaat ttgctttaaa aaagtggac aggcatattt    3660 acggggtttt ctcggacttc tccatgttaa tattcgtgtg tataaatcgc tcccgtgctg    3720
ctctctgggg gcccctcttt cacaaacacc tggccaccct cacgccacaa tggccaggca    3780
ggaacctcga cctcccctcg gagaggggc tcagggtcaa ccccgggtc tcagtctcta    3840 catgtgacgt tttcctgtcc cctcatttaa aataacaaga ggctgggcgc agtggcttac    3900
gcctgtaatc ccagcacttt ggaggccga ggcgggcgat cacgaggtca ggagatggag    3960
accatcctgg ccaacacggt gaaacccgc ctctactaaa ctacaaaaaa ttagccgggt    4020
gtggtggcgg gcgcctgtag tcccagctac tcgggaggct gaggcaggag aattgcttga    4080
acccggaggc gaaggttgca gtgagctgag atctcgccac tgcactccag cctggtgaca    4140
gagcctgact ccgtctcaaa aataagaaa aaaaaataaa ataaaaataa tagaggccga    4200
agcgggaggt tcacttgagc tcagaagttc gagatcagcc tggcaacac agtgagacct    4260 cgtttctatt taaaaaataa aataaaacta aatttaaaaa aatgcacgct catagtacaa    4320
actttagaaa tggaacgaaa aactaaaatt gaaggtattc ccctccaacc cagagataac    4380
acctatcgtt tattaagccc tcactattgt taaacttagt tttaaagggc acgatctcat    4440
ttcttaaaga cttctattcc gcagaatttc tttccaggct ttttttcttt tcttttttg     4500 agacggagtc tcgctctgtc gcccaggccg gggtgcagtg gcgcgatctc ggctcactga    4560
aacctctgtc cagtcttttc gaacccaagg cccaactgcg ctctatctcg actttcggct    4620
ccactcggat cccgaagtgg cgcacgagat aaaatgttgt caggctgagg taattctctg    4680
ttagtcccgg taaaaattcg tcagtctgga aagctctcgg tttggaatta aattctgtca    4740
ctccggatgg aaataagtcc gcttaagggg ggaaaatccg tttgtggagg acacgctccc    4800
gcacgtaacc ccccgcggaa aatgaccca agtacctttg gccagggatt gccgctgcca    4860
cgccggactc catagccacg gtcctgaaac gccccgccgg gcaggccgga ccaatggacg    4920
ccgagctcgg ccgtgcgtca cgcgacgctg gccaatcgcg gagggccacg accgtagaaa    4980
ggccgggcgc ggcgaggctg ggcgctgggc ggctgcggcg cgcggtgcgc ggtgcgtagt    5040
ctggagctat ggtggtggtg gcagccgcgc cgaacccggc cgacgggacc cctaaagttc    5100
tgcttctgtc ggggcagccc gcctccgccg ccggagcccc ggccggccag gcctgccgc     5160 tcatggtgcc agcccagaga ggggccagcc cggaggcagc gagcggggg ctgccccagg    5220 cgcgcaagcg acagcgcctc acgcacctga gccccgagga gaaggcgctg aggaggtggg    5280
cgaggggccc gggtctgggg ccagatctga agccgggact agggacaggg gcaggggcag    5340
gggctgggag cggggaccca gcactggccg ccccgcaggg ctccgtcgcc tttggcctgg    5400
```

-continued

```
cgggtcggtg ccagcgtggc gcggggcggg gcaggaagcc cggactgacc ggatccgcca    5460
cgctgggaac ctaggcggc ccagggctct tttctgtact ttttaactct ctcgttagag     5520
atgaccagag ctggggatgc gggcacctgt cttccaggcc ctcttgctgt gtggccgcag    5580
actggtggtt cagcctctta actcggacat gaggtcgaat aatctgtttt ggtttactgc    5640
tatttctgga gaggcgcgga gctgaaataa cagagctgtt gaaagggctg ggaattctgc    5700
gaggctcact ggtctagctc agtatctgcg ttcttaaaat ggaacctact tcatgaggtc    5760
tttggggaga ttgagacttg gatataatgt gcctagcact tagtcctccg taaatgttca    5820
ctcttttgtg atcattgtgc cttctgtgat ttatgaagtg tctcttctga gttaattctt    5880
ttaaaaaaaa aagtgtctcc tccaacagac acggacccat cagcaggtca ctgcctagga    5940
tctcaacact agagatcagg gagtggcatc agcctctccc ttttctaaat tggactgggg    6000
gacggagggt tgatgtcata gcaagattgc agccttcact agattaatga ggccaggttg    6060
gatcctgttt aagagaactg gagacaggaa gcagcggggg aatagatggg gaaagaggaa    6120
agttccttat gatgcaagat gaatagtgtg tgtgtccagc cccagtgctg tgacggggat    6180
gagtctgagg tggacggatg atgcaatata ggagagaata aagcaggtct tcgagctaga    6240
ttgacagaag actgtatttt ttattttgtt ttattgaggg gaggagcctg aagtgtattt    6300
tatcattagt ctgtcttata ctgtaaataa aaatgaaagc accagctggt aaagttttca    6360
aataaagaca taaataaggt ttgatatgac tcagtgtggg atgttccttc tcttcctagg    6420
aaactgaaaa acagagtagc agctcagact gccagagatc gaaagaaggc tcgaatgagt    6480
gagctggaac agcaagtggt agatttagaa gaagaggtaa aactacttaa ggtcaaactc    6540
ttttatccat tgtataccct tccttggtga atgttctgat atttgcttcc catcccaagt    6600
tgtttcagcc cctattagaa tacaattgaa tatatgatta aaagttaaac taggctgggc    6660
atggtggctc atgcctgtaa tcccagcact ttgggagcct gagttgggca gatcacttga    6720
agccagcagt ttgagaccag cctagccaac atggtaaaat cccgtctcta cccaaaaata    6780
taccaaaaaa aaaaaaaaaa aaaaggccaa gcgtgagtgc ctgtagtccc agctactcgg    6840
gaggttgagg tgggaggatt gtttgaacct gggagaggga ggttgcagtg agctgagatc    6900
gcaccactgc actccagcct gggcaacaga gtgagactct gtctcaagaa aaaaaaaaa    6960 agtttgctgg gcaccggggc tcacacctgt aatcccagca cttggggagg ccaaggtggg    7020
tagataactt gagatcagga gttcgagacc agcctgacca acgtggtgaa accccatctc    7080
tattaaaaat acaaaaatta gccgggtgtc gtggcaggca cctgtaatcc cagctgctcc    7140
ggaggctgac gcaggagaat cacttgaacc caggaggcgg aggttgcagt gagctgagat    7200
cacgagatca tgccactgca ctccagtctg ggcgacagag caaaaaccct gtctcaaaaa    7260 aaaaaaaaa gttaatctaa gttaggacag agagttggtg aagtggtgaa gcttgttgag    7320
ggcagaagtg attgactttg tggcatttgg tgctagatgt atctcaaagt agatggattt    7380
aacaatgttt attgagtttg tagtaagaaa ttagcaaggg ctaataggaa ataattgctt    7440
aaactttaca ttcttcctgg catggccaga aattcactaa aggttccttt cccctctag     7500 ggtccacctg ttaatcaatc ttaaattgtt gccaattaca catcttgaat acatagagat    7560
tatttatatt gttttttaa ccccttggtc aatttgcata tattgagctt tttaaagttt     7620
taatcattag ttggttcttc taagaatcat gagtcaggag cagggatttt ttttaactta    7680
ttttggattt atagtcacca ctaccacttt tattattacc tgccagttca agatagttat    7740
ttatttttat tttatattat tattattatt attatcatca tcattatttt gagatggagt    7800
```

```
ctcactctgt tgcccaggct ggagtgcagt ggtgcaatct cggctcactg caacctctgc    7860
ctcccaggtt caagcaattc tccctgcttc agcctccaga ttagctggga ttacaggcac    7920
ccctcaccac atccagctaa ttttggatt ttttagtaga gatggggt tgccatgttg       7980
gccaggctgg ttttgaactc ttgacctcag gtgatccacc tgccttggcc tcccaaagtg    8040
ttaggattac aagtgtgagc caccgagcct ggccaagata gtttaaaaaa aaaattatat    8100
ctacattaaa gccacaagtc acccttgct gaagtcagta ttagtagttg gaagcagtgt     8160
gttattcttg accccatgaa gtggcactta ttaagtagct tgcttttcca taattatggc    8220
ctagcttttt aaaacctact atgaacacca caagcataga gttttccaaa agttcaagaa    8280
ggaaaggaaa ccaattatac tgaatcaggt agattcttaa ctgaaataat tagatgtttt    8340
aatagcctct tatgaacttt cttccagaac caaaacttt tgctagaaaa tcagctttta    8400
cgagagaaaa ctcatggcct tgtagttgag aaccaggagt taagacagcg cttgggatg    8460
gatgccctgg ttgctgaaga ggaggcggaa gccaaggtaa atcatctcct ttatttggtg    8520
cctcatgtga gtactggttc caagtgacat gacccagcga ttatgttac agtctggact    8580
tctgatcaag agcgttcttg aaattttcct tcagttttaa gacattttca tgcaggcaga    8640
gtgttcttcc cctaaaggca cttgacactc atttttaag tgtgtagtga acagtactaa    8700
gatctaataa tgaaaacaag ttacatggcc ccctaagaac aagtactaac aaatgcagta    8760
gccaacaaga ttaccatgca atcattaagg agaaccaaag taagagagcc actcaaacca    8820
gattttgaac gctactaaaa ttaaagtagt tctttgatga atatgaatga gtagggaaag    8880
gattcttgt aatagtgata cctctgtggt aagagaaggg tggtatgtga gttttagtct    8940
acagattatg gcaaattcag tgacaacaat caaatggtct aagattgaca gtagcacagt    9000
tttactctgt gaaggtaatg ttcaggacaa atttcaagaa aactagaaaa ccattcttta    9060
cagctgaaat ctttccctaa ccattgttat ttccactttt aagtcctcaa gagatgagaa    9120
aagggaggta aggcttcctt atacatttcc tgcacaatga acatttttc ctcctccagg     9180
caaagattca agcagaactg gcaaatatct tatcttgctc ttctcaataa taataatgtt    9240
gttagataat aaagttctat agcaatttaa ccctagaatc ttttgaaaa gtaattcttt     9300
aaagttgaga atcacagctg tctagcaagc atttccttgg gcacttgaag ctgtttattc    9360
actttggtct ttcctcccag gggaatgaag tgaggccagt ggccgggtct gctgagtccg    9420
cagcactcag actacgtgca cctctgcagc aggtgcaggc ccagttgtca cccctccaga    9480
acatctcccc atggattctg gcggtattga ctcttcagat tcagaggtag ggatcattct    9540
gacttattaa agagctatat aaccagttaa ttccatctgt ttgatgcttg acatccctaa    9600
ctagacagat gagggttgaa gttagttttt ggtggggttg gaggtgaaca tcaactacct    9660
tcctagttcc aggtaatata gaacatggag tgaagtgtag ataaatgggt ctggtgggtc    9720
ccgaggtcat cttatcacat aatgactaat ttacattatg gaacccagta caaagtgttc    9780
cagttagatt ttccattgta ttctgacagt tgtacttcat ttaattttg cctcttacag     9840
tctgatatcc tgttgggcat tctggacaac ttggacccag tcatgttctt caaatgccct    9900
tccccagagc ctgccagcct ggaggagctc ccagaggtct acccagaagg acccagttcc    9960
ttaccagcct cccttctct gtcagtgggg acgtcatcag ccaagctgga agccattaat    10020
gaactaattc gttttgacca catatatacc aagcccctag tcttagagat accctctgag    10080
acagagagcc aagctaatgt ggtagtgaaa atcgaggaag cacctctcag cccctcagag    10140
aatgatcacc ctgaattcat tgtctcagtg aaggaagaac ctgtagaaga tgacctcgtt    10200
```

```
ccggagctgg gtatctcaaa tctgctttca tccagccact gcccaaagcc atcttcctgc    10260
ctactggatg cttacagtga ctgtggatac gggggttccc tttccccatt cagtgacatg    10320
tcctctctgc ttggtgtaaa ccattcttgg gaggacactt ttgccaatga actctttccc    10380
cagctgatta gtgtctaagg aatgatccaa tactgttgcc cttttccttg actattacac    10440
tgcctggagg atagcagaga agcctgtctg tacttcattc aaaaagccaa aatagagagt    10500
atacagtcct agagaattcc tctatttgtt cagatctcat agatgacccc caggtattgt    10560
cttttgacat ccagcagtcc aaggtattga gacatattac tggaagtaag aaatattact    10620
ataattgaga actacagctt ttaagattgt acttttatct aaaagggtg gtagttttcc     10680 ctaaaatact tattatgtaa gggtcattag acaaatgtct tgaagtagac atggaattta    10740
tgaatggttc tttatcattt ctcttccccc ttttggcat cctggcttgc ctccagtttt      10800 aggtcctta gtttgcttct gtaagcaacg ggaacacctg ctgaggggc tctttccctc        10860 atgtatactt caagtaagat caagaatctt ttgtgaaatt atagaaattt actatgtaaa    10920
tgcttgatgg aattttttcc tgctagtgta gcttctgaaa ggtgctttct ccatttattt    10980
aaaactaccc atgcaattaa aaggtacaat gcagcatcct tgtttgattt cttctagggc    11040
cgtaagtctt gttttctctc cagatgttta tctgtgtgct gtggtaggaa ttaatccaac    11100
tgaagtgagc ctaacgcttt ttaaagtgac tgaaggcttt tccaccttaa ttactgcctg    11160
ctttaattct ggactgccat aagtgatata agctataatt tgagcagtta ctgtcttct     11220 gagacagatt cttgagccta actgaccaat atcacagcta gtaagtggaa gagctagaac    11280
cctaaccact atttgctaca ccatcttata aatgttaaac aaggacacac catcacatat    11340
cgagattctc ttgcccttat tatgggaatt aagagcattt tctagactga aactccctat    11400
tttcaactct gccactggta agctgggtaa cccaggggtt atatataatc acttatttcc    11460
tcatctgtaa agttggataa tggtatctct aaaggttaag attcaaagag acgatgcatt    11520
ataagcattt agtatatgct aggcaccatc ctaaacactg gaaagttagt tagttattat    11580
ctcctaatcc actttggaag ggttttaatc tcttccagaa ttatatttac tcaagaattt    11640
gtttcatcaa agaataaacc tcggccaggc gcggtggctc atgcctgtaa tcccagcact    11700
ttgggaggct gaggcgggtg gatcacgagg tcaggagatc gagaccatcc tgcctaacat    11760
ggggaaaccc tgtctctact aaaattacaa aaaattagcc aggcgtgtg gtgggcgcct     11820 gtaatcccag ctacttggga ggctgaggca ggagaatggc gtgaacccgg gaggcggagc    11880
ttgcggtgag gggagatcgc gccactgcac tccagcctgg gcaacagagc gagactctgt    11940
ctcaaaaaat aaataaataa ataaataaat aaataaataa acctcttcaa gaaaaaatcc    12000
tagtgatatt aatacaactc ccaaagactt gataacctcc tcatccttca tagcatcttt    12060
tccttggaaa tcttacaagg ttttacagga ctttacttat ttataaaaat ttcacctatg    12120
ccagtagatg aaatcattct atgccaattt agcatttaaa tgctatgttc ccaacttaca    12180
aagactaact ctggggaggt caaagtgaat gagtagaaaa aaggcaggat tcagagaatc    12240
ccaagcagca aggcaaagtg gattatagaa tacctttggt gtaggccagg tgtagtggct    12300
cacgcttgta atcccaacac tttgggaggc tgaggtgggc ggatcacctg aggtcaggag    12360
ttcatggcca gcctgaccaa catagtgaaa ccccatctct agtaaaaata caaaattagc    12420
tgggtgtggt ggcgcatatg cctgtaatcc cagctactca ggaggctgag gcggcagaat    12480
cacttgaacc cggaggcag aggatgcagc gagccgagat cgtgccattg cactccagcc     12540
tgggcaacaa gagcgaaact ccatttaaaa aagaaaaaaa aaaatagaat gcctttcatg    12600
```

```
tagtgactgg aggcaagtca gctagctgcc ttcaagatcc ggtcgttgaa gccagggccc    12660
aatcctggtg ctcagcaata caaacttgct taggctctta agtttcttca gaaacaggcc    12720
aggcatggtg gctcacacct ataatcccag cactttggga ggccgaggcc agcagattgc    12780
ttggttcaag actagcctgg acaacatggc aaaccgtct ctccatgaaa agtaaaaaaa    12840
aatagccagg catggtggtg tgcactggtg gtcacagcca ctcaggaagc tgaggtggga    12900
ggatcgcttg aggccagggg gcagaggttg cagtcagcca agatcgcagc actgcactcc    12960
agactgggtg aaaaagcaag actgcctaaa aaaaaaaagg ttctgtatat aag           13013
```

METHOD FOR TREATING DISEASE USING FOXP3+CD4+ T CELLS

CROSS-REFERENCE TO RELATED APPLICATIONS

This application is a continuation of U.S. patent application Ser. No. 17/523,431, filed on Nov. 10, 2021, which claims priority to U.S. Provisional Patent Application Ser. No. 63/111,905, filed on Nov. 10, 2020, the entire content of each of which is incorporated herein by reference.

SEQUENCE LISTING

A computer readable form (CRF) sequence listing text file having the file name 0016002_SequenceListing.txt and file size of 64.2 KB is being submitted herewith. The sequence information contained in this sequence listing is limited to the sequence information in the application as originally filed, and does not include any new matter.

BACKGROUND

This document relates to methods and materials for treating a mammal having an autoimmune disease. For example, this document provides materials and methods for producing a T cell comprising a forkhead box P3 (FOXP3) polypeptide and one or more transcription factors. This document also provides methods and materials for treating a mammal having an autoimmune disease, where the methods include administering to a mammal having an autoimmune disease an effective amount of the T cell.

Autoimmunity is a common disease in the United States, with more than 20 million people suffering from one of 81 known autoimmune diseases. Regulatory T cells (Tregs) are a subpopulation of T cells that modulate the immune system and maintain tolerance to self-antigens. Tregs play a role in preventing or treating autoimmune disease (Sakaguchi et al., *Int'l Immun.*, 21(10):1105-1111 (2009)). FOXP3, a transcription factor expressed in Tregs, has been implicated in maintaining Treg immunosuppressive functions (Hort et al., *Science*, 299:1057-1061 (2003)). FOXP3$^+$ Tregs may impair (e.g., eliminate and/or inhibit) responder T cells involved in causing autoimmune disease by a granzyme-dependent or perforin-dependent mechanism (Trzonkowski et al., *Clin. Immunol.*, 112:258-67 (2004)). FOXP3$^+$ Tregs also may impair (e.g., eliminate and/or inhibit) responder T cells involved in causing autoimmune disease, by delivering a negative signal to responder T cells via up-regulation of intracellular cyclic AMP, which causes inhibition of responder T cell proliferation (Gondex et al., *J. Immunol.*, 174:1783-6 (2005)).

SUMMARY

This document provides methods and materials that can be used to treat mammals identified as having an autoimmune disease. For example, this document provides materials and methods for a T cell containing a FOXP3 polypeptide and one or more transcription factors. In another example, this document provides materials and methods for producing a T cell containing a FOXP3 polypeptide, one or more transcription factors, and a therapeutic gene product. This document also provides materials and methods for producing a T cell containing a FOXP3 polypeptide, one or more transcription factors, and a therapeutic gene product and/or a binding agent. In addition, this document provides methods and materials for treating a mammal having an autoimmune disease, where the methods include administering to the mammal an effective amount of a T cell (e.g., any of the T cells described herein). The methods and materials provided herein can provide a way to enhance and/or stabilize the immunosuppressive effects of a T cell in order to treat the autoimmune disease.

In general, one aspect of this document features a method for increasing T cell function, where the method includes introducing into a T cell: (i) a first nucleic acid sequence encoding a FOXP3 polypeptide; and (ii) a second nucleic acid sequence encoding one or more transcription factors. In some embodiments, the one or more transcription activators, when present in a mammalian cell, elicit a T reg phenotype in the mammalian cell as compared to when the one or more transcription factors is/are not present in the mammalian cell. In some embodiments, the first nucleic acid sequence can include a mutation that results in nuclear localization of the FOXP3 polypeptide. In some embodiments, the mutation that results in nuclear localization of the FOXP3 polypeptide can be in a sequence encoding a nuclear export sequence. In some embodiments, the nuclear export sequence can include an amino acid substitution selected from the group of L69A, L71A, L74A, L76A, L242A, L246A, and L248A. In some embodiments, the first nucleic acid sequence can include a mutation that results in stabilization of the FOXP3 polypeptide. In some embodiments, the mutation that results in stabilization of the FOXP3 polypeptide can change the level of phosphorylation of the FOXP3 polypeptide compared to FOXP3 polypeptide not having the mutation. In some embodiments, the mutation can result in the expression of a FOXP3 polypeptide having an amino acid substitution selected from the group of S19A, S33A, S57A, S58A, S59A, T115A, S418D, and S422A. In some embodiments, the mutation that results in the stabilization of the FOXP3 polypeptide can change the level of acetylation of the FOXP3 polypeptide compared to FOXP3 polypeptide that not having the mutation. In some embodiments, the mutation can result in the production of a FOXP3 polypeptide having an amino acid substitution mutation selected from the group of K31R, K206R, K216R, K227R, K250R, K252R, K268R, and K277R. In some embodiments, the one or more transcription factors can be selected from the group of: BLIMPL EOS, ROR-gt, FOXO1, GATA1, HELIOS, ID2, ID3, IRF4, LEF1, SATB1, GATA3, NFATc2, RUNX1, BC111b, Foxp1, Fox4, BACH2, STAT3, and XBP1. In some embodiments, the one or more transcription factors can be selected from selected form the group of: BLIMPL EOS, GATA1, HELIOS, GATA3, and NFATc2. In some embodiments, the transcription factor can be BLIMP-1.

In some embodiments, the introducing step further includes introducing a nucleic acid construct, where the nucleic acid construct includes the first nucleic acid sequence and the second nucleic acid sequence. In some embodiments, the nucleic acid construct can further include a promoter operably linked to the first nucleic acid sequence. In some embodiments, the first nucleic acid sequence can be 5' positioned relative to the second nucleic acid sequence in the nucleic acid construct. In some embodiments, the nucleic acid construct further can include an additional nucleic acid sequence between the first nucleic acid sequence and the second nucleic acid sequence, where the additional nucleic acid sequence operably links the second nucleic acid sequence to the first nucleic acid sequence. In some embodiments, the second nucleic acid sequence is 5' positioned relative to the first nucleic acid sequence in the nucleic acid construct. In some embodiments, the nucleic acid construct further includes an additional nucleic acid sequence between the second nucleic acid sequence and the first nucleic acid sequence, where the additional nucleic acid sequence operably links the first nucleic acid sequence to the second nucleic acid sequence. In some embodiments, the additional nucleic acid sequence can encode an internal ribosome entry site (IRES) sequence or a self-cleaving amino acid. In some embodiments, the additional nucleic acid sequence can include a promoter or enhancer.

In some embodiments, the introducing step further includes introducing a third nucleic acid sequence encoding a therapeutic gene product into the T cell, where the third nucleic acid sequence is operably linked to a promoter. In some embodiments, the therapeutic gene product can be an antigen-binding antibody fragment or antibody that is capable of binding to an IL-6, an IL-6R, an IFN alpha receptor, or a TGF beta receptor polypeptide. In some embodiments, the therapeutic gene product can be an antigen-binding fragment or antibody that is capable of binding to a IL-6 polypeptide or an IL-6R polypeptide.

In some embodiments, the nucleic acid sequence construct further includes a third nucleic acid sequence encoding the therapeutic gene product. In some embodiments, the introducing step further can include introducing a third nucleic acid sequence encoding a therapeutic gene product into the T cell, where the third nucleic acid sequence is operably linked to a promoter. In some embodiments, the therapeutic gene product can be an antigen-binding antibody fragment or antibody that is capable of binding to an IL-6, an IL-6R, an IFN alpha receptor, or a TGF beta receptor polypeptide. In some embodiments, the therapeutic gene product is an antigen-binding fragment or antibody that is capable of binding to an IL-6 polypeptide or an IL-6R polypeptide. In some embodiments, the third sequence can be 5' positioned relative to the first sequence and the second sequence, where the third sequence is operably linked a promoter. In some embodiments, the third sequence can be 3' positioned relative to the first and second sequence, where the third sequence is operably linked to the first sequence and/or the second sequence.

In some embodiments, the introducing step further includes introducing a fourth nucleic acid sequence encoding a binding agent into the T cell, where the fourth nucleic acid sequence is operably linked to a promoter. In some embodiments, the nucleic acid construct further includes a fourth nucleic acid sequence encoding a binding agent. In some embodiments, the binding agent can be an antibody or antigen-binding fragment. In some embodiments, the antigen-binding domain can be an antigen-binding fragment selected from the group of a Fab, a F(ab')$_2$ fragment, a scFV, a scab, a dAb, a single domain heavy chain antibody, and a single domain light chain antibody. In some embodiments, the antigen-binding fragment can be a scFv that is capable of binding to an antigen on an autoimmune cell. In some embodiments, the scFv is capable of binding to a cell adhesion molecule. In some embodiments, the cell adhesion molecule can be ICAM-1, VCAM-1, or MADCAM-1. In some embodiments, the binding agent can be a LFA-1 polypeptide. In some embodiments, the binding agent is a chimeric antigen receptor, where the chimeric antigen receptor includes an extracellular domain, a transmembrane domain, and an intracellular domain, where the extracellular domain includes an antibody or antigen-binding fragment capable of binding to an antigen on an autoimmune cell, and where the intracellular domain includes a cytoplasmic signaling domain and one or more co-stimulatory domains. In some embodiments, the antigen-binding domain is an antigen-binding fragment can be selected from the group of a Fab, a F(ab')$_2$ fragment, a scFV, a scAb, a dAb, a single domain heavy chain antibody, and a single domain light chain antibody. In some embodiments, the antigen-binding fragment can be a scFv that is capable of binding to an antigen on an autoimmune cell. In some embodiments, the scFv can be capable of binding to a cell adhesion molecule. In some embodiments, the cell adhesion molecule can be ICAM-1, VCAM-1, or MADCAM-1. In some embodiments, the cytoplasmic signaling domain can be a CD3 zeta domain. In some embodiments, the co-stimulatory domain can include at least one of a CD48, 4-1BB, ICOS, X-40, or CD27 domain. In some embodiments, the fourth sequence can be 5' positioned relative to the first sequence and the second sequence, where the fourth sequence is operably linked a promoter. In some embodiments, the fourth sequence can be 3' positioned relative to the first and second sequence, where the fourth sequence is operably linked to the first sequence and/or the second sequence.

In some embodiments, the nucleic acid construct further includes a third sequence encoding any of the therapeutic gene products described herein and a fourth sequence encoding any of the binding agents described herein. In some embodiments, the third sequence can be operably linked to a promoter and/or operably linked the first sequence and/or second sequence, and where the fourth sequence is operably linked to a promoter and/or operably linked the first sequence and/or second sequence.

In some embodiments, the nucleic acid construct can include a viral vector selected from the group of a lentiviral vector, a retroviral vector, an adenoviral vector, or an adeno-associated viral (AAV) vector. In some embodiments, the viral vector can be a lentiviral vector. In some embodiments, the introducing step includes viral transduction.

In some embodiments, the T cell is a CD4$^+$ T cell or a CD4$^+$/CD45RA$^+$ T cell. In some embodiments, the method further includes: obtaining a T cell from a patient or obtaining T cells allogenic to the patient. In some embodiments, the method further includes: treating the obtained T cells to isolate a population of cells enriched for CD4$^+$ T cells or CD4$^+$/CD45RA$^+$ T cells.

In another aspect, this document features a T cell produced by any of the methods described herein. In another aspect, this document features a composition including any of the T cells described herein.

In another aspect, this document features a T-cell including: a first nucleic acid sequence encoding a FOXP3 polypeptide; and a second nucleic acid sequence encoding one or more transcription factors. In some embodiments, the one or more transcription factors, when present in a mammalian cell, elicit a T reg phenotype in the mammalian cell as compared to when the transcription factor is not present in the mammalian cell. In some embodiments, the nuclear export sequence of the FOX3P polypeptide can include an amino acid substitution selected from the group of L69A, L71A, L74A, L76A, L242A, L246A, and L248A. In some embodiments, the first nucleic acid sequence can include a mutation that results in stabilization of the FOXP3 polypeptide. In some embodiments, the mutation that results in stabilization of the FOXP3 polypeptide can change the level of phosphorylation of the FOXP3 polypeptide compared to FOXP3 polypeptide not having the mutation. In some embodiments, the mutation results in the production of a FOXP3 polypeptide having an amino acid substitution selected from the group of S19A, S33A, S57A, S58A, S59A, T115A, S418D, and S422A. In some embodiments, the mutation that results in the stabilization of the FOXP3 polypeptide can change the level of acetylation of the FOXP3 polypeptide compared to FOXP3 polypeptide that not having the mutation. In some embodiments, the mutation results in the production of a FOXP3 polypeptide having an amino acid substitution mutation selected from the group of K31R, K206R, K216R, K227R, K250R, K252R, K268R, and K277R. In some embodiments, the one or more transcription factors can be selected from the group of: BLIMP1, EOS, ROR-gt, FOXO1, GATA1, HELIOS, ID2, ID3, IRF4, LEF1, SATB1, GATA3, NFATc2, RUNX1, BC111b, Foxp1, Fox4, BACH2, STAT3, and XBP1. In some embodiments, the one or more transcription factors can be selected from selected form the group of: BLIMP1, EOS, GATA1, HELIOS, GATA3, and NFATc2. In some embodiments, the transcription factor can be BLIMP-1. In some embodiments, the first nucleic acid sequence can be operably linked to a promoter. In some embodiments, the second nucleic acid sequence can be operably linked to a promoter.

In some embodiments, the T-cell further includes a third nucleic acid sequence encoding a therapeutic gene product into the T cell, where the third nucleic acid sequence is operably linked to a promoter. In some embodiments, the therapeutic gene product can be an antigen-binding antibody fragment or antibody that is capable of binding to an IL-6, an IL-6R, an IFN alpha receptor, or a TGF beta receptor polypeptide. In some embodiments, the therapeutic gene product can be an antigen-binding fragment or antibody that is capable of binding to a IL-6 polypeptide or an IL-6R polypeptide.

In some embodiments, the T-cell further includes introducing a fourth nucleic acid sequence encoding a binding agent into the T cell, where the fourth nucleic acid sequence is operably linked to a promoter. In some embodiments, the binding agent can be an antibody or antigen-binding fragment. In some embodiments, the antigen-binding domain can be an antigen-binding fragment selected from the group of a Fab, a F(ab')$_2$ fragment, a scFV, a scAb, a dAb, a single domain heavy chain antibody, and a single domain light chain antibody. In some embodiments, the antigen-binding fragment can be a scFv that is capable of binding to an antigen on an autoimmune cell. In some embodiments, the scFv is capable of binding to a cell adhesion molecule. In some embodiments, the cell adhesion molecule can be ICAM-1, VCAM-1, or MADCAM-1. In some embodiments, the binding agent can be a LFA-1 polypeptide.

In some embodiments, the binding agent is a chimeric antigen receptor, where the chimeric antigen receptor includes an extracellular domain, a transmembrane domain, and an intracellular domain, where the extracellular domain includes an antibody or antigen-binding fragment capable of binding to an antigen on an autoimmune cell, and where the intracellular domain includes a cytoplasmic signaling domain and one or more co-stimulatory domains. In some embodiments, the antigen-binding domain can be an antigen-binding fragment selected from the group of a Fab, a F(ab')$_2$ fragment, a scFV, a scAb, a dAb, a single domain heavy chain antibody, and a single domain light chain antibody. In some embodiments, the antigen-binding fragment can be a scFv that is capable of binding to an antigen on an autoimmune cell. In some embodiments, the scFv is capable of binding to a cell adhesion molecule. In some embodiments, the cell adhesion molecule can be ICAM-1, VCAM-1, or MADCAM-1. In some embodiments, the cytoplasmic signaling domain can be a CD3 zeta domain. In some embodiments, the co-stimulatory domain can include at least one of a CD48, 4-1BB, ICOS, X-40, or CD27 domain.

In another aspect, this document features a composition including a T cell produced using any of the methods described herein.

In another aspect, this document features a method of producing a T cell population expressing an exogenous FOXP3 polypeptide and one or more transcription factors, where the method includes culturing a T cell (e.g., any of the exemplary T cells described herein) in growth media under conditions sufficient to expand the population of T cells.

In another aspect, this document features a population of T cells produced using any of the methods described herein. In another aspect, this document features a composition including the population of T cells produced using any of the methods described herein.

In another aspect, this document features a vector including a first nucleic acid sequence encoding a FOXP3 polypeptide and a second nucleic acid sequence encoding a one or more transcription factors. In some embodiments, the one or more transcription factors, when present in a mammalian cell, elicit a T reg phenotype in the mammalian cell as compared to when the transcription factor is not present in the mammalian cell. In some embodiments, the nuclear export sequence of the FOX3P polypeptide can include an amino acid substitution selected from the group of L69A, L71A, L74A, L76A, L242A, L246A, and L248A. In some embodiments, the first nucleic acid sequence can include a mutation that results in stabilization of the FOXP3 polypeptide. In some embodiments, the mutation that results in stabilization of the FOXP3 polypeptide can change the level of phosphorylation of the FOXP3 polypeptide compared to FOXP3 polypeptide not having the mutation. In some embodiments, the mutation results in the production of a FOXP3 polypeptide having an amino acid substitution selected from the group of S19A, S33A, S57A, S58A, S59A, T115A, S418D, and S422A. In some embodiments, the mutation that results in the stabilization of the FOXP3 polypeptide can change the level of acetylation of the FOXP3 polypeptide compared to FOXP3 polypeptide that not having the mutation. In some embodiments, the mutation can result in the production of a FOXP3 polypeptide having an amino acid substitution selected from the group of K31R, K206R, K216R, K227R, K250R, K252R, K268R, and K277R. In some embodiments, the one or more transcription factors can be selected from the group of: BLIMP1, EOS, ROR-gt, FOXO1, GATA1, HELIOS, ID2, ID3, IRF4, LEF1, SATB1, GATA3, NFATc2, RUNX1, BC111b, Foxp1, Fox4, BACH2, STAT3, and XBP1. In some embodiments, the one or more transcription factors can be selected from selected form the group of: BLIMP1, EOS, GATA1, HELIOS, GATA3, and NFATc2. In some embodiments, the transcription factor can be BLIMP-1.

In some embodiments, the vector further includes a promoter operably linked to the first nucleic acid sequence. In some embodiments, the first nucleic acid sequence can be 5' positioned relative to the second nucleic acid in the vector. In some embodiments, the vector further includes an additional nucleic acid sequence between the first nucleic acid sequence and the second nucleic acid sequence, where the additional nucleic acid sequence operably links the second nucleic acid sequence to the first nucleic acid sequence. In some embodiments, the second nucleic acid sequence can be 5' positioned relative to the first nucleic acid sequence in the vector. In some embodiments, the vector further includes an additional nucleic acid sequence between the second nucleic acid sequence and the first nucleic acid sequence, where the additional nucleic acid sequence operably links the first nucleic acid sequence to the second nucleic acid sequence. In some embodiments, the additional nucleic acid sequence can encode an internal ribosome entry site (IRES) sequence or a self-cleaving amino acid. In some embodiments, the additional nucleic acid sequence can include a promoter or enhancer.

In some embodiments, the vector further includes a third nucleic acid sequence encoding a therapeutic gene product. In some embodiments, the therapeutic gene product can be an antigen-binding antibody fragment or antibody that is capable of binding to an IL-6, an IL-6R, an IFN alpha receptor, or a TGF beta receptor polypeptide. In some embodiments, the therapeutic gene product can be an antigen-binding fragment or antibody that is capable of binding to an IL-6 polypeptide or an IL-6R polypeptide. In some embodiments, the third nucleic acid sequence can be 5' positioned relative to the first sequence and the second sequence, where the third nucleic acid sequence is operably linked to a promoter. In some embodiments, the third nucleic acid sequence can be 3' positioned relative to the first and second nucleic acid sequence, where the third nucleic acid sequence is operably linked to the first nucleic acid sequence and/or the second nucleic acid sequence.

In some embodiments, the vector further includes a fourth nucleic acid sequence encoding a binding agent. In some embodiments, the binding agent can be an antibody or antigen-binding fragment. In some embodiments, the antigen-binding domain can be an antigen-binding fragment selected from the group of a Fab, a F(ab')₂ fragment, a scFV, a scAb, a dAb, a single domain heavy chain antibody, and a single domain light chain antibody. In some embodiments, the antigen-binding fragment can be a scFv that is capable of binding to an antigen on an autoimmune cell. In some embodiments, the scFv is capable of binding to a cell adhesion molecule. In some embodiments, the cell adhesion molecule can be ICAM-1, VCAM-1, or MADCAM-1. In some embodiments, the binding agent can be a LFA-1 polypeptide.

In some embodiments, the binding agent is a chimeric antigen receptor, where the chimeric antigen receptor includes an extracellular domain, a transmembrane domain, and an intracellular domain, where the extracellular domain includes an antibody or antigen-binding fragment capable of binding to an antigen on an autoimmune cell, and where the intracellular domain includes a cytoplasmic signaling domain and one or more co-stimulatory domains. In some embodiments, the antigen-binding domain can be an antigen-binding fragment selected from the group of a Fab, a F(ab')₂ fragment, a scFV, a scAb, a dAb, a single domain heavy chain antibody, and a single domain light chain antibody. In some embodiments, the antigen-binding fragment can be a scFv that is capable of binding to an antigen on an autoimmune cell. In some embodiments, the scFv is capable of binding to a cell adhesion molecule. In some embodiments, the cell adhesion molecule can be ICAM-1, VCAM-1, or MADCAM-1. In some embodiments, the cytoplasmic signaling domain can be a CD3 zeta domain. In some embodiments, the co-stimulatory domain includes at least one of a CD48, 4-1BB, ICOS, X-40, or CD27 domain.

In some embodiments, the fourth nucleic acid sequence can be 5' positioned relative to the first nucleic acid sequence and the second nucleic acid sequence, where the fourth nucleic acid sequence is operably linked a promoter. In some embodiments, the fourth nucleic acid sequence can be 3' positioned relative to the first and second nucleic acid sequence, where the fourth nucleic acid sequence is operably linked to the first nucleic acid sequence and/or the second nucleic acid sequence. In some embodiments, the third nucleic acid sequence is operably linked to a promoter and/or operably linked the first nucleic acid sequence and/or second nucleic acid sequence, and where the fourth nucleic acid sequence is operably linked to a promoter and/or operably linked the first nucleic acid sequence and/or second nucleic acid sequence.

In some embodiments, the vector includes a viral vector selected from the group of a lentiviral vector, a retroviral vector, an adenoviral vector, or an adeno-associated viral (AAV) vector. In some embodiments, the viral vector can be a lentiviral vector.

In another aspect, this document features a composition including any of the vectors described herein. In another aspect, this document features a kit including any of the compositions described herein.

In another aspect, this document features a method of treating an autoimmune disease or disorder in a patient including administering any of the T cells described herein, or any of the compositions described herein. In some embodiments, the subject can be previously diagnosed or identified as having an autoimmune disease or disorder. In some embodiments, the autoimmune disease or disorder can be lupus, rheumatoid arthritis, multiple sclerosis, insulin dependent diabetes mellitis, myasthenia gravis, Graves disease, autoimmune hemolytic anemia, autoimmune thrombocytopenia purpura, Goodpasture's syndrome, pemphigus vulgaris, acute rheumatic fever, post-streptococcal glomerulonephritis, Crohn's disease, Celiac disease, or polyarteritis *nodosa*. In some embodiments, the administering of the autologous or allogenic T cell population can include intravenous injection or intravenous infusion. In some embodiments, the administering can result in amelioration of one or more symptoms of the autoimmune disease or disorder.

Unless otherwise defined, all technical and scientific terms used herein have the same meaning as commonly understood by one of ordinary skill in the art to which this invention pertains. Although methods and materials similar or equivalent to those described herein can be used to practice the invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

The details of one or more embodiments of the invention are set forth in the accompanying drawings and the description below. Other features, objects, and advantages of the invention will be apparent from the description and drawings, and from the claims.

DETAILED DESCRIPTION

Figure 1:
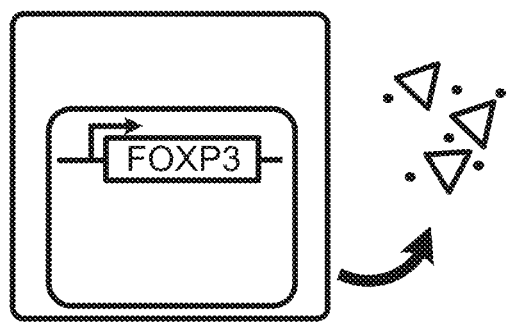
FIG. 1 is a diagram showing an exemplary targetable cell with enforced expression of a FOXP3 polypeptide. Enforced expression of a FOXP3 polypeptide results in a core Treg suppressive program (e.g., IL-2 consumption and increase in CD25 expression, an increase in adenosine, an increase in CD39 expression, and expression of CTLA-4).
Figure 2:
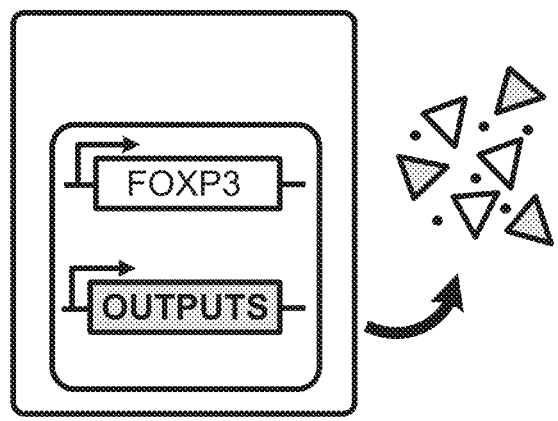
FIG. 2 is a diagram showing an exemplary targetable cell with enforced expression of a FOXP3 polypeptide and a therapeutic gene product. Expression of a therapeutic gene product in addition to a FOXP3 polypeptide can result in enhancement of a core Treg program. Examples of suitable therapeutic gene products include, without limitation, IL6R scFv, IFNαR scFv, IL-10, IL-4, IL-13, and any other anti-fibrotic-related output.

This document provides methods and materials that can be used to treat mammals identified as having an autoimmune disease. For example, this document provides materials and methods for producing a T cell containing a FOXP3 polypeptide and one or more transcription factors (miRNA). In another example, this document provides materials and methods for producing a T cell containing a FOXP3 polypeptide, one or more transcription factors, and a therapeutic gene product. In a third example, this document also provides materials and methods for producing a T cell containing a FOXP3 polypeptide, one or more transcription factors, and a binding agent. In a fourth example, this document provides materials and methods for producing a T cell containing a FOXP3 polypeptide, one or more transcription factors, a therapeutic gene product, and a binding agent. In addition, this document provides methods and materials for treating a mammal having an autoimmune disease, where the methods include administering to the mammal an effective amount of a T cell produced using any of the methods described herein.

This document provides methods and materials for introducing into a T cell (e.g., CD4+ T cell, CD4+ CD45RA+ T cell, CD4+ CD62L+ T cell, or central memory T cell) a first nucleic acid sequence encoding a FOXP3 polypeptide and a second nucleic acid sequence encoding one or more transcription factors. In some embodiments, the one or more transcription factors, when present in a mammalian cell, elicits a T reg phenotype in the mammalian cell as compared to when the transcription factor(s) is/are not present in the mammalian cell.

In some embodiments, a first nucleic acid sequence encoding a FOXP3 polypeptide having one or more mutations is introduced into a T cell (e.g., CD4+ T cell, CD4+ CD45RA+ T cell, CD4+CD62L+ T cell, or central memory T cell). For example, a mutation in the first nucleic acid sequence encoding a FOXP3 polypeptide can include, without limitation, mutations that result in an amino acid substitution that changes the stability (e.g., level of phosphorylation or acetylation), function (e.g., transcriptional regulation), or sub-cellular localization (e.g., nuclear localization) of the encoded FOXP3 polypeptide.

In some embodiments, a FOXP3 polypeptide can have an amino acid substitution in one or more nuclear export sequences (NES) that can result in nuclear localization of the FOXP3 polypeptide. Transducing cells with a FOXP3 polypeptide having one or more amino acid substitutions, amino acid insertions, and/or amino acid deletions in the nuclear export sequences can result in establishment, maintenance, or enhancement of a FOXP3 polypeptide-dependent expression profile that is indicative of expression profiles seen in native Treg cells (e.g., Treg cells isolated from a healthy human). In some cases, a cell (e.g., a CD4+ T cell) with a FOXP3 polypeptide-dependent expression profile can have increased immunosuppressive function. For example, a cell transduced with a FOXP3 polypeptide having one or more amino acid substitutions, amino acid insertions, and/or amino acid deletions as described herein can have increased expression of genes that are transcriptional targets of a FOXP3. Increased expression of these genes (e.g., Il-2, Ctla-4, and Tnfrsf18) can result in increased Treg cell function (e.g., inhibition of responder cell proliferation). In some embodiments, a FOXP3 polypeptide can having one or more amino acid substitutions, amino acid insertions, and/or amino acid deletions within a sequence encoding a NES. In cases where the FOXP3 polypeptide includes one or more amino acid deletions, the one or more deletions can be within a part of a NES (e.g., deletion of a part of a NES, deletion of an entire NES, or deletion of a larger fragment containing a NES sequence (e.g., corresponding to exon 2 or exon 7 of a FOXP3 polypeptide). For example, a FOXP3 polypeptide having the amino acids corresponding to exon 2-deleted (FOXP3d2), amino acids corresponding to exon 7 deleted (FOXP3d7), or amino acids corresponding to exon 2 and 7-deleted (FOXP3d2d7) can result in the nuclear localization of the FOXP3 polypeptide. In some embodiments, point mutations in the first nucleic acid sequence encoding the nuclear export sequences (e.g., NES1, having an amino acid sequence set forth in SEQ ID NO: 4, and NES2, having the amino acid sequence of SEQ ID NO: 5) can be any mutation (e.g., nucleic acid substitution, insertion, and/or deletion) that results in a change within the amino acid sequence of NES1 and/or NES2 and renders the nuclear export signal non-functional. Amino acid substitutions in NES1 and/or NES2 that can result in nuclear localization of a FOXP3 polypeptide include, without limitation: of L69A, L71A, L74A, L76A, L242A, L246A, and L248A. FOXP3 polypeptides harboring any one or more of these amino acid substitutions, amino acid insertions, and/or amino acid deletions can sequestered to the nucleus.

In some embodiments, the first nucleic acid sequence encoding the FOXP3 polypeptide can encode one or more fragments of a full length FOXP3 polypeptide (e.g., a full length FOXP3 polypeptide such as version NP_001107849.1). In some embodiments, a cell can be transduced with a first nucleic acid sequence encoding a FOXP3 polypeptide that includes at least the regions of FOXP3 that have DNA-binding properties (e.g., polypeptide fragments of FOXP3 that can bind to a ATAACA DNA sequence) (Li et al., *Acta Biochim. Biophysc. Sin.*, 49(9): 792-99 (2017)).

In some embodiments, an amino acid substitution in a FOXP3 polypeptide that changes the level of phosphorylation can stabilize the FOXP3 polypeptide (e.g., increase the half-life of the FOXP3 polypeptide). For example, a mutation in a first nucleic acid sequence encoding a FOXP3 polypeptide can result in an amino acid substitution that changes the level of phosphorylation of the FOXP3 polypeptide compared to a FOXP3 polypeptide not having the amino acid substitution. Non-limiting examples of amino acid substitutions that can change the level of phosphorylation of the FOXP3 polypeptide include S19A, S33A, S57A, S58A, S59A, T115A, S418D, and S422A.

In some embodiments, an amino acid substitution in a FOXP3 polypeptide is a phosphomimetic amino acid substitution. Phosphomimetics are amino acid substitutions that mimic a phosphorylated polypeptide or can encourage phosphorylation at a particular amino acid position, thereby activating or deactivating the polypeptide. For example, the phosphorylation of Ser418 can be enforced by a phosphoserine mimetic substitution of that residue into an alanine or aspartate. A mutation can be made in the first nucleic acid sequence encoding a FOXP3 polypeptide to produce a FOXP3 polypeptide having the S418D substitution. The S418D residue then serves as phosphomimetic amino acid residue. Additional amino acid residues that can be substituted to produce phosphomimetic amino acid residues include serines at positions 19, 33, 41, 88, and 422, threonines at sites 114 and 175 in FOXP3. See, Morawski, et al.,

*J Biol Chem.*, 288(34): 24494-24502 (2013). For example, phosphomimetics of these sites can be engineered by substituting the serine or threonine for alanine. These phosphomimetics can enhance the stability and immunosuppressive activity of a FOXP3 polypeptide.

In some embodiments, an amino acid substitution in a FOXP3 polypeptide that changes the level of acetylation can stabilize the FOXP3 polypeptide (e.g., increase the half-life of the FOXP3 polypeptide). For example, a mutation in a first nucleic acid sequence encoding a FOXP3 polypeptide can result in an amino acid substitution that changes the level of acetylation of the FOXP3 polypeptide compared to a FOXP3 polypeptide not having the amino acid substitution. Non-limiting examples of amino acid substitutions that can change the level of acetylation of the FOXP3 polypeptide include K31R, K206R, K216R, K227R, K250R, K252R, K268R, and K277R.

In some embodiments, a second nucleic acid encoding one or more transcription factors is introduced into a T cell (e.g., $CD4^+$ T cell, $CD4^+$ $CD45RA^+$ T cell, $CD4^+$ $CD62L^+$ T cell, or central memory T cell) along with the first nucleic acid sequence encoding the FOXP3 polypeptide. In some embodiments, introducing a first nucleic acid sequence encoding a FOXP3 polypeptide and a second nucleic acid sequence encoding one or more transcription factors into a $CD4^+$ T cell enhances the suppressive activity of the T cell. In some embodiments, introducing a second nucleic acid sequence encoding one or more transcription factors into a $CD4^+$ T cell elicits a T reg phenotype (e.g., immune suppression phenotype) in the T cell as compared to when the one or more transcription factors is/are not present in the mammalian cell. For example, introducing a second nucleic acid sequence encoding an NFATC2 polypeptide into a T cell (e.g., $CD4^+$ T cell or any of the other exemplary T cells described herein) can induce a T reg phenotype (e.g., immune suppression phenotype) in the T cell. In another example, introducing a second nucleic acid sequence encoding a GATA3 polypeptide into a T cell (e.g., CD4+ T cell or any of the other exemplary T cells described herein) can induce a T reg phenotype (e.g., immune suppression phenotype) in the T cell. Non-limiting examples of transcription factors that can be used to enhance the T reg phenotype of a T cell include BLIMP1, EOS, ROR-γt, FOXO1, GATA1, HELIOS, ID2, ID3, IRF4, LEF1, SATB1, GATA3, NFATc2, RUNX1, BC111b, Foxp1, Fox4, BACH2, STAT3, and XBP1. For example, a first nucleic acid sequence encoding the FOXP3 polypeptide and a second nucleic acid sequence encoding BLIMP-1 polypeptide can be introduced into a T cell (e.g., $CD4^+$ T cell, $CD4^+$ $CD45RA^+$ T cell, $CD4^+$ $CD62L^+$ T cell, or central memory T cell). Dntmt3a is responsible for methylation of genomic DNA encoding FOXP3 causing downregulation of FOXP3 and reducing the immunosuppressive functionality of the T cell. BLIMP1 blocks the upregulation of Dnmt3a. (See Garg, et al., *Cell Reports*, 26:1854-1868 (2019)). Expression of BLIMP1 prevents methylation (e.g., silencing) of FOXP3 thereby enabling continued expression of FOXP3 and maintenance of the T reg phenotype in the T cell. A T reg phenotype can include, e.g., one or more of IL-2 consumption, an increase in CD25 expression, an increase in adenosine, an increase in CD39 expression, and expression of CTLA-4. Additional markers of a T reg phenotype are known in the art.

This document provides methods and materials for introducing into a T cell (e.g., $CD4^+$ T cell, $CD4^+$ $CD45RA^+$ T cell, $CD4^+$ $CD62L^+$ T cell, or central memory T cell) a first nucleic acid sequence encoding a FOXP3 polypeptide (e.g., any of the exemplary FOXP3 polypeptides described herein) and a second nucleic acid sequence encoding one or more transcription factors (e.g., any of the exemplary transcription factors described herein), and a therapeutic gene product. Any appropriate therapeutic gene product that enhances the immunosuppressive effects of a T cell (e.g., a $CD4^+$ $CD45^+$ T cell) can be used. Examples of therapeutic gene products include, without limitation, antigen or antigen-binding fragments directed to interferon alpha receptor 1 (IFNAR1), interleukin 10 (IL-10, interleukin 4 (IL-4), interleukin 13 (IL-13), interleukin 6 (IL-6), IL-6 receptor (IL-6R), and any other anti-fibrotic agent. In some embodiments, the therapeutic gene product can enhance the immunosuppressive effect of the transduced cell. For example, a therapeutic gene product can be any polypeptide or other agent that prohibits an IL-6 polypeptide from binding to an IL-6 receptor (IL-6R). In such cases, a therapeutic gene product can be an antagonist for IL-6R (e.g., an antibody or antigen-binding fragment that binds to IL-6R) and/or blocking antibody or antigen-binding fragment of IL-6 (e.g., a scFv capable of binding to IL-6). Additional examples of therapeutic gene products include, without limitation, cytokines, cytokine receptors, differentiation factors, growth factors, growth factor receptors, peptide hormones, metabolic enzymes, receptors, T cell receptors, chimeric antigen receptors (CARs), transcriptional activators, transcriptional repressors, translation activators, translational repressors, immune-receptors, apoptosis inhibitors, apoptosis inducers, immune-activators, and immune-inhibitors.

This document provides methods and materials for introducing into a T cell (e.g., $CD4^+$ T cell, $CD4^+$ $CD45RA^+$ T cell, $CD4^+$ $CD62L^+$ T cell, or central memory T cell) a first nucleic acid sequence encoding a FOXP3 polypeptide (e.g., any of the exemplary FOXP3 polypeptides described herein) and a second nucleic acid sequence encoding one or more transcription factors (e.g., any of the exemplary transcription factors described herein), a therapeutic gene product (e.g., any of the exemplary therapeutic gene products as described herein), and a binding agent. Also provided herein are methods and materials for introducing into a T cell (e.g., $CD4^+$ T cell, CD4+CD45RA+ T cell, CD4+CD62L+ T cell, or central memory T cell) a first nucleic acid sequence encoding a FOXP3 polypeptide (e.g., any of the exemplary FOXP3 polypeptides described herein) and a second nucleic acid sequence encoding one or more transcription factors (e.g., any of the exemplary transcription factors described herein), and a binding agent.

As used herein, "binding agent" refers to any variety of extracellular substance that binds with specificity to its cognate binding partner. In some embodiments, a cell (e.g., a $CD4^+$ $CD45RA^+$ T cell) can be transduced with nucleic acid sequences encoding a mutated FOXP3 polypeptide as described herein, one or more transcription factors, and a binding agent. In some embodiments, a binding agent can be any polypeptide that enhances the immunosuppressive effect of a T cell (e.g., a $CD4^+$ $CD45RA^+$ T cell). In some embodiments, a binding agent can be a polypeptide that binds to molecules found specifically on autoimmune cells or tissues. For example, a binding agent can be a lymphocyte function associated antigen-1 (LFA-1) polypeptide. An LFA-1 can bind to cell adhesion molecules on the surface of cells associated with autoimmune diseases. Examples of binding partners for LFA-1 include, without limitation, ICAM-1, VCAM-1 and MADCAM-1. In another example, a binding agent can be a polypeptide that binds to a VCAM-1 polypeptide (e.g., a scFv capable of binding to a VCAM-1 polypeptide). In yet another example, a binding agent can be a polypeptide that binds to a MADCAM-1 polypeptide (e.g., a scFv capable of binding to a MAD-CAM-1 polypeptide). In some embodiments, a binding agent can be a chimeric antigen receptor (CAR) as described herein where the CAR has an extracellular domain, a transmembrane domain, and an intracellular domain. In cases where the binding agent is a CAR, the extracellular domain includes a polypeptide capable of binding to a molecule found specifically on autoimmune cells or tissues. For example, the extracellular domain can include an scFV capable of binding to antigen on an autoimmune cell.

As used herein, "FOXP3" refers to the FOXP3 gene or protein that is a transcription factor in the Forkhead box (Fox) family of transcription factors (Sakaguchi et al., Int'l Immun., 21(10):1105-1111 (2009); Pandiyan, et al., Cytokine, 76(1):13-24 (2015)), or a variant thereof (e.g., a FOXP3 protein having one or more (e.g., one, two, three, four, five, six, seven, eight, nine, ten, eleven, twelve, thirteen, fourteen, fifteen, sixteen, seventeen, eighteen, nineteen, or twenty amino acid substitutions, amino acid deletions, or amino acid insertions as compared to a wildtype FOXP3 protein). In some embodiments, when preparing a T cell to be used in the treatment of a mammal having an autoimmune disease by administering to the mammal the T cell, FOXP3 refers to human FOXP3 or a variant thereof. An example of a wildtype human FOXP3 polypeptide includes, without limitation, NCBI reference sequence: NP 001107849.1 or a fragment thereof.

As used herein, "nuclear localization" means an increase in the level of FOXP3 (e.g., any of the FOXP3 polypeptides described herein) in the nucleus of a mammalian cell (e.g., any of the T cells described herein) as compared to a control mammalian cell (e.g., a mammalian cell expressing wildtype FOXP3 or a mammalian cell not genetically modified to include any of a first, second, third, and fourth nucleic acid sequences as described herein).

In some embodiments referring to a first nucleic acid sequence encoding a FOXP3 (e.g., full length FOXP3) polypeptide, the nucleic acid sequence is at least 70% (e.g., at least 75%, 80%, 85%, 90%, 95%, 99% and 100%) identical to:

(SEQ ID NO: 1)
AGTTTCCCACAAGCCAGGCTGATCCTTTTCTGTCAGTCCACTTCACCAAG

CCTGCCCTTGGACAAGGACCCGATGCCCAACCCCAGGCCTGGCAAGCCCT

CGGCCCCTTCCTTGGCCCTTGGCCCATCCCCAGGAGCCTCGCCCAGCTGG

AGGGCTGCACCCAAAGCCTCAGACCTGCTGGGGGCCCGGGGCCCAGGGGG

AACCTTCCAGGGCCGAGATCTTCGAGGCGGGGCCCATGCCTCCTCTTCTT

CCTTGAACCCCATGCCACCATCGCAGCTGCAGCTCTCAACGGTGGATGCC

CACGCCCGGACCCCTGTGCTGCAGGTGCACCCCTGGAGAGCCCAGCCAT

GATCAGCCTCACACCACCCACCACCGCCACTGGGGTCTTCTCCCTCAAGG

CCCGGCCTGGCCTCCCACCTGGGATCAACGTGGCCAGCCTGGAATGGGTG

TCCAGGGAGCCGGCACTGCTCTGCACCTTCCCAAATCCCAGTGCACCCAG

GAAGGACAGCACCCTTTCGGCTGTGCCCCAGAGCTCCTACCCACTGCTGG

CAAATGGTGTCTGCAAGTGGCCCGGATGTGAGAAGGTCTTCGAAGAGCCA

GAGGACTTCCTCAAGCACTGCCAGGCGGACCATCTTCTGGATGAGAAGGG

CAGGGCACAATGTCTCCTCCAGAGAGAGATGGTACAGTCTCTGGAGCAGC

AGCTGGTGCTGGAGAAGGAGAAGCTGAGTGCCATGCAGGCCCACCTGGCT

GGGAAAATGGCACTGACCAAGGCTTCATCTGTGGCATCATCCGACAAGGG

CTCCTGCTGCATCGTAGCTGCTGGCAGCCAAGGCCCTGTCGTCCCAGCCT

GGTCTGGCCCCCGGGAGGCCCCTGACAGCCTGTTTGCTGTCCGGAGGCAC

CTGTGGGGTAGCCATGGAAACAGCACATTCCCAGAGTTCCTCCACAACAT

GGACTACTTCAAGTTCCACAACATGCGACCCCCTTTCACCTACGCCACGC

TCATCCGCTGGGCCATCCTGGAGGCTCCAGAGAAGCAGCGGACACTCAAT

GAGATCTACCACTGGTTCACACGCATGTTTGCCTTCTTCAGAAACCATCC

TGCCACCTGGAAGAACGCCATCCGCCACAACCTGAGTCTGCACAAGTGCT

TTGTGCGGGTGGAGAGCGAGAAGGGGGCTGTGTGGACCGTGGATGAGCTG

GAGTTCCGCAAGAAACGGAGCCAGAGGCCCAGCAGGTGTTCCAACCCTAC

ACCTGGCCCCTGACCTCAAGATCAAGGAAAGGAGGATGGACGAACAGGGG

CCAAACTGGTGGGAGGCAGAGGTGGTGGGGGCAGGGATGATAGGCCCTGG

ATGTGCCCACAGGGACCAAGAAGTGAGGTTTCCACTGTCTTGCCTGCCAG

GGCCCCTGTTCCCCCGCTGGCAGCCACCCCCTCCCCCATCATATCCTTTG

CCCCAAGGCTGCTCAGAGGGGCCCCGGTCCTGGCCCCAGCCCCCACCTCC

GCCCCAGACACACCCCCAGTCGAGCCCTGCAGCCAAACAGAGCCTTCAC

AACCAGCCACACAGAGCCTGCCTCAGCTGCTCGCACAGATTACTTCAGGG

CTGGAAAAGTCACACAGACACACAAAATGTCACAATCCTGTCCCTCACTC

AACACAAACCCCAAAACACAGAGAGCCTGCCTCAGTACACTCAAACAACC

TCAAAGCTGCATCATCACACAATCACACACAAGCACAGCCCTGACAACCC

ACACACCCCAAGGCACGCACCCACAGCCAGCCTCAGGGCCCACAGGGGCA

CTGTCAACACAGGGGTGTGCCCAGAGGCCTACACAGAAGCAGCGTCAGTA

CCCTCAGGATCTGAGGTCCCAACACGTGCTCGCTCACACACACGGCCTGT

TAGAATTCACCTGTGTATCTCACGCATATGCACACGCACAGCCCCCCAGT

GGGTCTCTTGAGTCCCGTGCAGACACACACAGCCACACACACTGCCTTGC

CAAAAATACCCCGTGTCTCCCCTGCCACTCACCTCACTCCCATTCCCTGA

GCCCTGATCCATGCCTCAGCTTAGACTGCAGAGGAACTACTCATTTATTT

GGGATCCAAGGCCCCCAACCCACAGTACCGTCCCCAATAAACTGCAGCCG

AGCTCCCCA.

In some embodiments referring to a first nucleic acid sequence encoding a FOXP3 polypeptide having a mutation in exon 2, the nucleic acid sequence corresponding to FOXP3 exon 2 is at least 80% (e.g., at least 85%, 90%, 95%, 99% and 100%) identical to: CCTGCCCTTGGACAAGGACCCGATGCC-CAACCCCAGGCCTGGCAAGCCCTCGGCCC CTTCCTTGGCCCTTGGCCCATCCCCAG-GAGCCTCGCCCAGCTGGAGGGCTGCACCCA AAGCCTCA-GACCTGCTGGGGGCCCGGGGCCCAGGGG-GAACCTTCCAGGGCCGAGAT CTTCGAGGCGGGGCCCATGCCTCCTCTTCTTCCTT-GAACCCCATGCCACCATCGCAG CTGCAG (SEQ ID NO: 2). In some embodiments referring to a first nucleic acid sequence encoding a FOXP3 polypeptide having a deleted exon 2, the nucleic acid sequence that is deleted from full length FOXP3 polypeptide (SEQ ID NO: 1) is SEQ ID NO: 2 or a fragment of SEQ ID NO: 2.

In some embodiments referring to a first nucleic acid sequence encoding a FOXP3 polypeptide having a mutation in exon 7, the nucleic acid sequence corresponding to FOXP3 exon 7 is at least 80% (e.g., at least 85%, 90%, 95%, 99% and 100%) identical to: CTGGTGCTG-GAGAAGGAGAAGCTGAGTGCCATGCAGGCC-CACCTGGCTGGGAAAAT GGCACTGACCAAGGCTT-CATCTGTG (SEQ ID NO: 3). In some embodiments referring to a first nucleic acid sequence encoding a FOXP3 polypeptide having a deleted exon 7, the nucleic acid sequence that is deleted from full length FOXP3 (SEQ ID NO: 1) is SEQ ID NO: 3 or a fragment of SEQ ID NO: 3. In some embodiments referring to a first nucleic acid sequence encoding a FOXP3 polypeptide having a deleted exon 2 and a deleted exon 7, the nucleic acid sequences that are deleted from full length FOXP3 (SEQ ID NO: 1) are SEQ ID NO: 2 or a fragment thereof and SEQ ID NO: 3 or a fragment thereof.

In some embodiments referring to a mutation in a nuclear export sequence of FOXP3, the amino acid sequence corresponding to the NES1 is QLQLPTLPL (SEQ ID NO: 4). In some embodiments referring to a mutation in a nuclear export sequence of FOXP3, the amino acid sequence corresponding to the NES2 is VQSLEQQLVL (SEQ ID NO: 5).

As used herein, the term "chimeric antigen receptor" or "CAR" refers to a chimeric antigen receptor comprising an extracellular domain, a transmembrane domain, and an intracellular domain. In some cases, the extracellular domain can comprise an antigen-binding domain as described herein. In some cases, the transmembrane domain can comprise a transmembrane domain derived from a natural polypeptide obtained from a membrane-binding or transmembrane protein. For example, a transmembrane domain can include, without limitation, a transmembrane domain from a T cell receptor alpha or beta chain, a CD3 zeta chain, a CD28 polypeptide, or a CD8 polypeptide. In some cases, the intracellular domain can comprise a cytoplasmic signaling domain as described herein. In some cases, the intracellular domain can comprise a co-stimulatory domain as described herein.

As used herein, "T-cell function" refers to a T cell's (e.g., any of the exemplary T cells described herein) survival, stability, and/or ability to execute its intended function. For example, a CD4+ T cell can have an immunosuppressive function. A CD4+ T cell including a first nucleic acid sequence encoding a FOXP3 polypeptide can have a FOXP3-dependent expression profile that increases the immunosuppressive function of the T cell. For example, a cell transduced with a mutated FOXP3 polypeptide as described herein can have increased expression of genes that are transcriptional targets of a FOXP3 that can result in increased T reg cell function. In some embodiments, a T cell is considered to have T reg function if the T cell exhibits or maintains the potential to exhibit an immune suppression function.

As used herein, the term "activation" refers to induction of a signal on an immune cell (e.g., a B cell or T cell) that to results in initiation of the immune response (e.g., T cell activation). In some cases, upon binding of an antigen to a T cell receptor (TCR) or an exogenous chimeric antigen receptor (CAR), the immune cell can undergo changes in protein expression that result in the activation of the immune response. In some cases, a TCR or CAR includes a cytoplasmic signaling sequence that can drive T cell activation. For example, upon binding of the antigen, a chimeric antigen receptor comprising an intracellular domain that includes a cytoplasmic signaling sequence (e.g., an immune-receptor tyrosine-based inhibition motifs (ITAM)) that can be phosphorylated. A phosphorylated ITAM results in the induction of a T cell activation pathway that ultimately results in a T cell immune response. Examples of ITAMs include, without limitation, CD3 gamma, CD3 delta, CD3 epsilon, TCR zeta, FcR gamma, FcR beta, CD5, CD22, CD79a, and CD66d.

As used herein, the term "stimulation" refers to stage of TCR or CAR signaling where a co-stimulatory signal can be used to achieve a robust and sustained TCR or CAR signaling response. As described herein, a co-stimulatory domain can be referred to as a signaling domain. In some cases, a signaling domain (e.g., co-stimulatory domain) can be a CD27, CD28, OX40, CD30, CD40, B7-H3, NKG2C, LIGHT, CD7, CD2, 4-1BB, or PD-1.

In some embodiments where the chimeric antigen receptor polypeptide includes a CD3 zeta cytoplasmic signaling domain, the CD3 zeta cytoplasmic signaling domain has an amino acid sequence that is at least 80% (e.g., at least 85%, 90%, 95%, 99% and 100%) identical to: MKWKA-LFTAAILQAQLPITEAQSFGLLDPKLCYLLDGILF IYGVILTALF LRVKFSRSADAPAYQQGQNQ LYNELNLGRR EEYDVLDKRR GRDPEMGGKP QRRKNPQEGL YNELQKDKMAEAYSEIGMKG ERRRGKGHDG LYQGLSTATK DTYDALHMQA LPPR (NCBI Reference No.: NP_932170) (SEQ ID NO: 13), or a fragment thereof that has activating or stimulatory activity.

In some embodiments where the chimeric antigen receptor polypeptide includes a CD28 co-stimulatory domain, the CD28 co-stimulatory domain is at least 80% (e.g., at least 85%, 90%, 95%, 99% and 100%) identical to:

(SEQ ID NO: 6)
IEVMYPPPYLDNEKSNGTIIHVKGKHLCPSPLFPGPSKPFWVLVVVGGVL

ACYSLLVTVAFIIFWVRSKRSRLLHSDYMNMTPRRPGPTRKHYQPYAPPR

DFAAY.

Transcription Factors

As used herein, the term "transcription factor" refers to a polypeptide possessing one or more domains that bind to a DNA-regulatory sequence (e.g., promoter, enhancer, or silencer) to modulate the rate of gene transcription. This may result in increased or decreased gene transcription, protein synthesis, and subsequent altered cellular function.

As used herein, BLIMP1 also known as PRDM1 refers to PR/SET domain 1 polypeptide. When preparing a T cell or treating a mammal with a T cell, BLIMP1 or PRDM1 refers to human BLIMP1 or PRDM1. An example of a human BLIMP1 or PRDM1 polypeptide includes, without limitation, NCBI reference sequence: NP_001189.2. In some embodiments referring to a second nucleic acid sequence encoding a BLIMP1 (e.g., full length BLIMP1) polypeptide, the nucleic acid sequence is at least 70% (e.g., at least 75%, at least 80%, at least 85%, at least 90%, at least 95%, at least 99%, or at least 100%) identical to:

(SEQ ID NO: 7)
AACACAGACAAAGTGCTGCCGTGACACTCGGCCCTCCAGTGTTGCGGAGAGGCAAG

AGCAGCGACCGCGGCACCTGTCCGCCCGGAGCTGGGACGCGGGCGCCCGGGCGGCC

GGACGAAGCGAGGAGGGACCGCCGAGGTGCGCGTCTGTGCGGCTCAGCCTGGCGGG

-continued

```
GGACGCGGGGAGAATGTGGACTGGGTAGAGATGAACGAGACTTTTCTCAGATGTTG
GATATTTGCTTGGAAAAACGTGTGGGTACGACCTTGGCTGCCCCCAAGTGTAACTCC
AGCACTGTGAGGTTTCAGGGATTGGCAGAGGGGACCAAGGGGACCATGAAAATGGA
CATGGAGGATGCGGATATGACTCTGTGGACAGAGGCTGAGTTTGAAGAGAAGTGTA
CATACATTGTGAACGACCACCCCTGGGATTCTGGTGCTGATGGCGGTACTTCGGTTC
AGGCGGAGGCATCCTTACCAAGGAATCTGCTTTTCAAGTATGCCACCAACAGTGAA
GAGGTTATTGGAGTGATGAGTAAAGAATACATACCAAAGGGCACACGTTTTGGACC
CCTAATAGGTGAAATCTACACCAATGACACAGTTCCTAAGAACGCCAACAGGAAAT
ATTTTTGGAGGATCTATTCCAGAGGGGAGCTTCACCACTTCATTGACGGCTTTAATG
AAGAGAAAAGCAACTGGATGCGCTATGTGAATCCAGCACACTCTCCCCGGGAGCAA
AACCTGGCTGCGTGTCAGAACGGGATGAACATCTACTTCTACACCATTAAGCCCATC
CCTGCCAACCAGGAACTTCTTGTGTGGTATTGTCGGGACTTTGCAGAAAGGCTTCAC
TACCCTTATCCCGGAGAGCTGACAATGATGAATCTCACACAAACACAGAGCAGTCT
AAAGCAACCGAGCACTGAGAAAAATGAACTCTGCCCAAAGAATGTCCCAAAGAGA
GAGTACAGCGTGAAAGAAATCCTAAAATTGGACTCCAACCCCTCCAAAGGAAAGGA
CCTCTACCGTTCTAACATTTCACCCCTCACATCAGAAAAGGACCTCGATGACTTTAG
AAGACGTGGGAGCCCCGAAATGCCCTTCTACCCTCGGGTCGTTTACCCCATCCGGGC
CCCTCTGCCAGAAGACTTTTTGAAAGCTTCCCTGGCCTACGGGATCGAGAGACCCAC
GTACATCACTCGCTCCCCCATTCCATCCTCCACCACTCCAAGCCCCTCTGCAAGAAG
CAGCCCCGACCAAAGCCTCAAGAGCTCCAGCCCTCACAGCAGCCCTGGGAATACGG
TGTCCCCTGTGGGCCCCGGCTCTCAAGAGCACCGGGACTCCTACGCTTACTTGAACG
CGTCCTACGGCACGGAAGGTTTGGGCTCCTACCCTGGCTACGCACCCCTGCCCCACC
TCCCGCCAGCTTTCATCCCCTCGTACAACGCTCACTACCCCAAGTTCCTCTTGCCCCC
CTACGGCATGAATTGTAATGGCCTGAGCGCTGTGAGCAGCATGAATGGCATCAACA
ACTTTGGCCTCTTCCCGAGGCTGTGCCCTGTCTACAGCAATCTCCTCGGTGGGGGCA
GCCTGCCCCACCCCATGCTCAACCCCACTTCTCTCCCGAGCTCGCTGCCCTCAGATG
GAGCCCGGAGGTTGCTCCAGCCGGAGCATCCCAGGGAGGTGCTTGTCCCGGCGCCC
CACAGTGCCTTCTCCTTTACCGGGGCCGCCGCCAGCATGAAGGACAAGGCCTGTAGC
CCCACAAGCGGGTCTCCCACGGCGGGAACAGCCGCCACGGCAGAACATGTGGTGCA
GCCCAAAGCTACCTCAGCAGCGATGGCAGCCCCCAGCAGCGACGAAGCCATGAATC
TCATTAAAAACAAAAGAAACATGACCGGCTACAAGACCCTTCCCTACCCGCTGAAG
AAGCAGAACGGCAAGATCAAGTACGAATGCAACGTTTGCGCCAAGACTTTCGGCCA
GCTCTCCAATCTGAAGGTCCACCTGAGAGTGCACAGTGGAGAACGGCCTTTCAAATG
TCAGACTTGCAACAAGGGCTTTACTCAGCTCGCCCACCTGCAGAAACACTACCTGGT
ACACACGGGAGAAAAGCCACATGAATGCCAGGTCTGCCACAAGAGATTTAGCAGCA
CCAGCAATCTCAAGACCCACCTGCGACTCCATTCTGGAGAGAAACCATACCAATGC
AAGGTGTGCCCTGCCAAGTTCACCCAGTTTGTGCACCTGAAACTGCACAAGCGTCTG
CACACCCGGGAGCGGCCCCACAAGTGCTCCCAGTGCCACAAGAACTACATCCATCT
CTGTAGCCTCAAGGTTCACCTGAAAGGGAACTGCGCTGCGGCCCCGGCGCCTGGGC
TGCCCTTGGAAGATCTGACCCGAATCAATGAAGAAATCGAGAAGTTTGACATCAGT
GACAATGCTGACCGGCTCGAGGACGTGGAGGATGACATCAGTGTGATCTCTGTAGT
```

```
GGAGAAGGAAATTCTGGCCGTGGTCAGAAAAGAGAAAGAAGAAACTGGCCTGAAA

GTGTCTTTGCAAAGAAACATGGGGAATGGACTCCTCTCCTCAGGGTGCAGCCTTTAT

GAGTCATCAGATCTACCCCTCATGAAGTTGCCTCCCAGCAACCCACTACCTCTGGTA

CCTGTAAAGGTCAAACAAGAAACAGTTGAACCAATGGATCCTTAAGATTTTCAGAA

AACACTTATTTTGTTTCTTAAGTTATGACTTGGTGAGTCAGGGTGCCTGTAGGAAGT

GGCTTGTACATAATCCCAGCTCTGCAAAGCTCTCTCGACAGCAAATGGTTTCCCCTC

ACCTCTGGAATTAAAGAAGGAACTCCAAAGTTACTGAAATCTCAGGGCATGAACAA

GGCAAAGGCCATATATATATATATATATATCTGTATACATATTATATATACTTATT

TACACCTGTGTCTATATATTTGCCCCTGTGTATTTTGAATATTTGTGTGGACATGTTT

GCATAGCCTTCCCATTACTAAGACTATTACCTAGTCATAATTATTTTTTCAATGATAA

TCCTTCATAATTTATTATACAATTTATCATTCAGAAAGCAATAATTAAAAAAGTTTAC

AATGACTGGAAAGATTCCTTGTAATTTGAGTATAAATGTATTTTTGTCTTGTGGCCAT

TCTTTGTAGATAATTTCTGCACATCTGTATAAGTACCTAAGATTTAGTTAAACAAATA

TATGACTTCAGTCAACCTCTCTCTCTAATAATGGTTTGAAAATGAGGTTTGGGTAATT

GCCAATGTTGGACAGTTGATGTGTTCATTCCTGGGATCCTATCATTTGAACAGCATT

GTACATAACTTGGGGGTATGTGTGCAGGATTACCCAAGAATAACTTAAGTAGAAGA

AACAAGAAAGGGAATCTTGTATATTTTTGTTGATAGTTCATGTTTTTCCCCCAGCCAC

AATTTTACCGGAAGGGTGACAGGAAGGCTTTACCAACCTGTCTCTCCCTCCAAAGA

GCAGAATCCTCCCACCGCCCTGCCCTCCCCACCGAGTCCTGTGGCCATTCAGAGCGG

CCACATGACTTTTGCATCCATTGTATTATCAGAAAATGTGAAGAAGAAAAAAATGCC

ATGTTTTAAAACCACTGCGAAAATTTCCCCAAAGCATAGGTGGCTTTGTGTGTGTGC

GATTTGGGGGCTTGAGTCTGGGTGGTGTTTTGTTGTTGGTTTTTGTTGCTTTTTTTTT

TTTTTTTTTTAATGTCAAAATTGCACAAACATGGTGCTCTACCAGGAAGGATTCGA

GGTAGATAGGCTCAGGCCACACTTTAAAAACAAACACACAAACAACAAAAAACGG

GTATTCTAGTCATCTTGGGGTAAAAGCGGGTAATGAACATTCCTATCCCCAACACAT

CAATTGTATTTTTTCTGTAAAACTCAGATTTTCCTCAGTATTTGTGTTTTTACATTTTA

TGGTTAATTTAATGGAAGATGAAAGGGCATTGCAAAGTTGTTCAACAACAGTTACCT

CATTGAGTGTGTCCAGTAGTGCAGGAAATGATGTCTTATCTAATGATTTGCTTCTCTA

GAGGAGAAACCGAGTAAATGTGCTCCAGCAAGATAGACTTTGTGTTATTCTATCTTT

TATTCTGCTAAGCCCAAAGATTACATGTTGGTGTTCAAAGTGTAGCAAAAAATGATG

TATATTTATAAATCTATTTATACCACTATATCATATGTATATATATTTATAACCACTT

AAATTGTGAGCCAAGCCATGTAAAAGATCTACTTTTTCTAAGGGCAAAAAAAAAAA

AAAAAAAAAAAGAACACTCCTTTCTGAGACTTTGCTTAATACTTGGTGACCTCACAA

TCACGTCGGTATGATTGGGCACCCTTGCCTACTGTAAGAGACCCTAAAACCTTGGTG

CAGTGGTGGGGACCACAAAACAACCAGGGAGGAAGAGATACATCATTTTTTAGTAT

TAAGGACCATCTAAGACAGCTCTATTTTTTTTTGCCACTTTATGATTATGTGGTCAC

ACCCAAGTCACAGAAATAAAAAACTGACTTTACCGCTGCAATTTTTCTGTTTTCCTCC

TTACTAAATACTGATACATTACTCCAATCTATTTTATAATTATATTTGACATTTTGTTC

ACATCAACTAATGTTCACCTGTAGAAGAGAACAAATTTCGAATAATCCAGGGAAAC

CCAAGAGCCTTACTGGTCTTCTGTAACTTCCAAGACTGACAGCTTTTTATGTATCAGT

GTTTGATAAACACAGTCCTTAACTGAAGGTAAACCAAAGCATCACGTTGACATTAGA
```

```
CCAAATACTTTTGATTCCCAACTACTCGTTTGTTCTTTTTCTCCTTTTGTGCTTTCCCA

TAGTGAGAATTTTTATAAAGACTTCTTGCTTCTCTCACCATCCATCCTTCTCTTTTCTG

CCTCTTACATGTGAATGTTGAGCCCACAATCAACAGTGGTTTTATTTTTTCCTCTACT

CAAAGTTAAAACTGACCAAAGTTACTGGCTTTTTACTTTGCTAGAACAACAAACTAT

CTTATGTTTACATACTGGTTTACAATGTTATTTATGTGCAAATTGTCAAAATGTAAAT

TAAATATAAATGTTCATGCTTTACCAAAA.
```

As used herein, EOS also known as Ikzf4 refers to Ikaros family zinc finger 4 polypeptide. When preparing a T cell or treating a mammal with a T cell, EOS or Ikzf4 refers to human EOS or Ikzf4. An example of a human EOS or Ikzf4 polypeptide includes, without limitation, NCBI reference sequence: NP_001338018.1. In some embodiments referring to a second nucleic acid sequence encoding a EOS (e.g., full length EOS) polypeptide, the nucleic acid sequence is at least 70% (e.g., at least 75%, at least 80%, at least 85%, at least 90%, at least 95%, at least 99%, or at least 100%) identical to:

```
                                              (SEQ ID NO: 8)
CCCTTCTCAGGTGAAGCTGCTGATGGAGATGGAGCCGCCGCCACCGCCGCCTCTGAG

CGCCCGGGTCCTGGCTCCGGCCCGGCGACTGCCGCCGCCTCAGTGACCCCACTCCCC

CCGCACTGGGCCGCCCGGGCCAGAGTGGGGGACCCCCGCCCCCTCGCCTCCCTCTCC

CCCAACACTGTCCCCTCTCCCCAACCCCTCACAGCCTGCGCGCGCGCGGAGACACCT

CAGTCTACATGGGGAGGACAGAGAAGCGCAAAGAACAAGAGAAAAGATGCATCCA

TCTGAGATCTAAAAGGAGACAATGAGAATCTCTTTAAAATGGACATAGAAGACTGC

AATGGCCGCTCCTATGTGTCTGTAGGACCAATGAAGGAATTATTGGCATGCACTAAA

GGAGATAGCAAGATGGGTCAGACACACATATGAGAGTCATTGGCAACACCCGGGTA

ATGTAAGGAATCCACGCTTCCTGGAAGGTGAGTGGCTGGGCTCACCCCTGCCTGCCA

CTGAGACGCAGACATGCATACACCACCCGCACTCCCTCGCCGTTTCCAAGGCGGCG

GCCGCGTTCGCACCCCAGGGTCTCACCGGCAAGGGAAGGATAATCTGGAGAGGGAT

CCCTCAGGAGGGTGTGTTCCGGATTTCTTGCCTCAGGCCCAAGACTCCAACCATTTT

ATAATGGAATCTTTATTTTGTGAAAGTAGCGGGGACTCATCTCTGGAGAAGGAGTTC

CTCGGGGCCCCAGTGGGGCCCTCGGTGAGCACCCCCAACAGCCAGCACTCTTCTCCT

AGCCGCTCACTCAGTGCCAACTCCATCAAGGTGGAGATGTACAGCGATGAGGAGTC

AAGCAGACTGCTGGGGCCAGATGAGCGGCTCCTGGAAAAGGACGACAGCGTGATTG

TGGAAGATTCATTGTCTGAGCCCCTGGGCTACTGTGATGGGAGTGGGCCAGAGCCTC

ACTCCCCTGGGGGCATCCGGCTGCCCAATGGCAAGCTCAAGTGTGACGTCTGCGGC

ATGGTCTGTATTGGACCCAACGTGCTCATGGTGCACAAGCGCAGTCACACTGGTGAA

AGGCCCTTCCATTGCAACCAGTGTGGTGCCTCCTTCACCCAGAAGGGGAACCTGCTG

CGCCACATCAAGCTGCACTCTGGGGAGAAGCCCTTTAAATGTCCCTTCTGCAACTAT

GCCTGCCGCCGGCGTGATGCACTCACTGGTCACCTCCGCACACACTCAGTCTCCTCT

CCCACAGTGGGCAAGCCCTACAAGTGTAACTACTGTGGCCGGAGCTACAAACAGCA

GAGTACCCTGGAGGAGCACAAGGAGCGGTGCCATAACTACCTACAGAGTCTCAGCA

CTGAAGCCCAAGCTTTGGCTGGCCAACCAGGTGACGAAATACGTGACCTGGAGATG

GTGCCAGACTCCATGCTGCACTCATCCTCTGAGCGGCCAACTTTCATCGATCGTCTG

GCCAATAGCCTCACCAAACGCAAGCGTTCCACACCCCAGAAGTTTGTAGGCGAAAA

GCAGATGCGCTTCAGCCTCTCAGACCTCCCCTATGATGTGAACTCGGGTGGCTATGA

AAAGGATGTGGAGTTGGTGGCACACCACAGCCTAGAGCCTGGCTTTGGAAGTTCCCT
```

-continued

```
GGCCTTTGTGGGTGCAGAGCATCTGCGTCCCCTCCGCCTTCCACCCACCAATTGCAT

CTCAGAACTCACGCCTGTCATCAGCTCTGTCTACACCCAGATGCAGCCCCTCCCTGG

TCGACTGGAGCTTCCAGGATCCCGAGAAGCAGGTGAGGGACCTGAGGACCTGGCTG

ATGGAGGTCCCCTCCTCTACCGGCCCCGAGGCCCCCTGACTGACCCTGGGGCATCCC

CCAGCAATGGCTGCCAGGACTCCACAGACACAGAAAGCAACCACGAAGATCGGGTT

GCGGGGTGGTATCCCTCCCTCAGGGTCCCCCACCCCAGCCACCTCCCACCATTGTG

GTGGGCCGGCACAGTCCTGCCTACGCCAAAGAGGACCCCAAGCCACAGGAGGGGTT

ATTGCGGGCACCCCAGGCCCCTCCAAGGAAGTGCTTCGGGTGGTGGGCGAGAGTG

GTGAGCCTGTGAAGGCCTTCAAGTGTGAGCACTGCCGTATCCTCTTCCTGGACCACG

TCATGTTCACTATCCACATGGGCTGCCATGGCTTCAGAGACCCTTTTGAGTGCAACA

TCTGTGGTTATCACAGCCAGGACCGGTACGAATTCTCTTCCCACATTGTCCGGGGGG

AGCATAAGGTGGGCTAGCAACCTCTCCCTCTCTCCTCAGTCCACCACTCCACTGCCC

TGACTACAGGCATTGATCCCTGTCCCCACCATTTCCCAAGGAGTTTTGCTTTGTAGCC

CTCACTACTGGCCACCTGACCTCACACCTGACCCTGACCCCTCCTCACCTATTCTCTT

CCTCTATCCTGACCGATGTAAGCATTGTGATGAAACAGATCTTTTGCTTATGTTTTTC

CTTTTTATCTTCTCTCATCCCAGCATACTGAGTTATTTATTAATTAGTTGATTTATTTT

TGCCTTTTTAAATTTTAACTTATATCAGTCACTTGCCACTCCCCCACCCTCCTGTCCA

CAACTCCTTTCCACTTTAGGCCAATTTTTCTCTCTTAGATCTTCCAGCAGCCCCAGGG

GTAGGAAGCTCCTCTTAGTACTAAGAGACTTCAAGCTTCTTGCTTTAAGTCCTCACCC

TTTACATTATCTAATTCTTCAGTTTTGATGCTGATACCTGCCCCCGGCCCTACCTTAG

CTCTGTGGCATTATATCTCCTCTCTGGGACTCTTCAACCTGGTACTCCATACCTCTTG

TGCCCTCTCACTTTAGGCAGCTTGCACTATTCTTGAATGAATGAAGAATTATTTCCTC

ATTTGGAAGTAGGAGGGACTGAAGAAATTCTCCCCAGGCACTGTGGGACTGAGAGT

CCTATTCCCCTAGTAATAGGTCATATTCCCCTAGTAATATGAGTTCTCAAAGCCTACA

TTCAGGATCTCCCTCTAGGATGTGATAGATCTGGTCCCTCTCCTTGAACTACCCCTCC

ACACGCTCTAGTCCCTTCAACCTACCGGTCTATTAAGTGGTGGCTTTTCTCTCCTTGG

AGTGCCCCAATTTTATATTCTCAGGGGCCAAGGCTAGGTCTGCAACCCTCTGTCTCT

GACAGATTGGGAGCCACAGGTGCCTAATTGGGAACCAGGGCATGGGAAAGGAGTG

GGTCAAAATTCTTCTCTTTCTCCTCCACCTCTCAAACTTCTTCACTATAGTGACCTTCC

TAGGCTCTCAGGGGCTCCTTCAGTCCCCATCCTATGAGAAACTAGTGGGTTGCTGCC

TGATGACAAGGGGTTGTTTCAGCCCCTCAGTCATGCTGCCTTCTGCTGCTCCCTCCCA

GCAGGATTCACCCTCTCATTCCCGGGCTCCTGGGCCCTGTTCTTAGGATCAGTGGCA

GGGAGAAACGGGTATCTCTTTTCTCTCTTCTAATTTTCAGTATAACCAAAAATTATCC

CAGCATGAGCACGGGCACGTGCCCTTCACCCCATTCCACCCTTGTTCCAGCAAGACT

GGGATGGGTACAACTGAACTGGGGTCTTCCTTTACTACCCCCTTCTACACTCAGCTC

CCAGACACAGGGTAGGAGGGGGACTGCTGGCTACTGCAGAGACCCTTGGCTATTT

GAGTAACCTAGGATTAGTGAGAAGGGGCAGAAGGAGATACAACTCCACTGCAAGTG

GAGGTTTCTTTCTACAAGAGTTTTCTGCCCAAGGCCACAGCCATCCCACTCTCTGCTT

CCTTGAGATTCAAACCAAAGGCTGTTTTTCTATGTTTAAAGAAAAAAAAAAGTAAAA

ACCAAACACAACACCTCACAAGTTGTAACTCTTGGTCCTTCTCTCTCTCCTTTTCTCT

TCCCTTCCTTCCCCTTCCATCTTTCTTTCCACATGTCCTTTCCTTATTGGCTCTTTTACC
```

```
-continued
TCCTACTTTTCTCACTCCCTATCAGGGATATTTTGGGGGGGGATGGTAAAGGGTGGG

CTAAGGAACAGACCCTGGGATTAGGGCCTTAAGGGCTCTGAGAGGAGTCTACCTTG

CCTTCTTATGGGAAGGGAGACCCTAAAAAACTTTCTCCTCTTTGTCCTCCTTTTTCTC

CCCCACTCTGAGGTTTCCCCAAGAGAACCAGATTGGCAGGGAGAAGCATTGTGGGG

CAATTGTTCCTCCTTGACAATGTAGCAATAAATAGATGCTGCCAAGGGCAGAAAATG

GGGAGGTTAGCTCAGAGCAGAGTAGTCTCTAGAGAAAGGAAGAATCCTCAACGGCA

CCCTGGGGTGCTAGCTCCTTTTTAGAATGTCAGCAGAGCTGAGATTAATATCTGGGC

TTTTCCTGAACTATTCTGGTTATTGAGCCCTTCCTGTTAGACCTACCGCCTCCCACCT

CTTCTGTGTCTGCTGTGTATTTGGTGACACTTCATAAGGACTAGTCCCTTCTGGGGTA

TCAGAGCCTTAGGGTGCCCCCATCCCCTTCCCCAGTCAACTGTGGCACCTGTAACCT

CCCGGAACATGAAGGACTATGCTCTGAGGCTATACTCTGTGCCCATGAGAGCAGAG

ACTGGAAGGGCAAGACCAGGTGCTAAGGAGGGGAGAGGGGGCATCCTGTCTCTCTC

CAGACCATCACTGCACTTTAACCAGGGTCTTAGGTACAAAATCCTACTTTTCAGAGC

CTTCCAGCTCTGGAACCTCAAACATCCTCATGCTCTCTCCCAGCTCCTTTTGCATAAA

AAAAAAAGTAAAGAAAAAGAAAAAAAAATACACACACACTGAAACCCACATGGAG

AAAAGAGGTGTTTCCTTTTATATTGCTATTCAAAATCAATACCACCAACAAAATATT

TCTAAGTAGACACTTTTCCAGACCTTTGTTTTTTTGTGTCAGTGTCCAAGCTGCAGAT

AGGATTTTGTAATACTTCTGGCAGCTTCTTTCCTTGTGTACATAATATATATATATAC

ATATATATATATATTTTTAATCAGAAGTTATGAAGAACAAAAAGAAAAAATAAACA

CAGAAGCAAGTGCAATACCACCTCTCTTCTCCCTCTCTCCTAGGGTTTCCTTTGTAGC

CTATGTTTGGTGTCTCTTTTGACCTTTACCCCTTCACCTCCTCCTCTCTTCTTCTGATT

CCCCTCCCCCCCTTTTTAAAGAGTTTTTCTCCTTTCTCAAGGGGAGTTAAACTAGCT

TTTGAGACTTATTGCAAAGCATTTTGTATATGTAATATATTGTAAGTAAATATTTGTG

TAACGGAGATATACTACTGTAAGTTTTGTACTGTACTGGCTGAAAGTCTGTTATAAA

TAAACATGAGTAATTTAACA.
```

As used herein, GATA1 refers to a GATA binding protein 1 polypeptide. When preparing a T cell or treating a mammal with a T cell, GATA1 refers to human GATA1. An example of a human GATA1 polypeptide includes, without limitation, NCBI reference sequence: NP_002040.1. In some embodiments referring to a second nucleic acid sequence encoding a GATA1 (e.g., full length GATA1) polypeptide, the nucleic acid sequence is at least 70% (e.g., at least 75%, at least 80%, at least 85%, at least 90%, at least 95%, at least 99%, or at least 100%) identical to:

```
                                               (SEQ ID NO: 9)
ACACTGAGCTTGCCACATCCCCAAGGCGGCCGAACCCTCCGCAACCACCAGCCCAG

GTTAATCCCCAGAGGCTCCATGGAGTTCCCTGGCCTGGGGTCCCTGGGGACCTCAGA

GCCCCTCCCCCAGTTTGTGGATCCTGCTCTGGTGTCCTCCACACCAGAATCAGGGGT

TTTCTTCCCCTCTGGGCCTGAGGGCTTGGATGCAGCAGCTTCCTCCACTGCCCCGAG

CACAGCCACCGCTGCAGCTGCGGCACTGGCCTACTACAGGGACGCTGAGGCCTACA

GACACTCCCCAGTCTTTCAGGTGTACCCATTGCTCAACTGTATGGAGGGGATCCCAG

GGGGCTCACCATATGCCGGCTGGGCCTACGGCAAGACGGGGCTCTACCCTGCCTCA

ACTGTGTGTCCCACCCGCGAGGACTCTCCTCCCCAGGCCGTGGAAGATCTGGATGGA

AAAGGCAGCACCAGCTTCCTGGAGACTTTGAAGACAGAGCGGCTGAGCCCAGACCT

CCTGACCCTGGGACCTGCACTGCCTTCATCACTCCCTGTCCCCAATAGTGCTTATGG

GGGCCCTGACTTTTCCAGTACCTTCTTTTCTCCCACCGGGAGCCCCCTCAATTCAGCA
```

-continued
```
GCCTATTCCTCTCCCAAGCTTCGTGGAACTCTCCCCCTGCCTCCCTGTGAGGCCAGG

GAGTGTGTGAACTGCGGAGCAACAGCCACTCCACTGTGGCGGAGGGACAGGACAGG

CCACTACCTATGCAACGCCTGCGGCCTCTATCACAAGATGAATGGGCAGAACAGGC

CCCTCATCCGGCCCAAGAAGCGCCTGATTGTCAGTAAACGGGCAGGTACTCAGTGC

ACCAACTGCCAGACGACCACCACGACACTGTGGCGGAGAAATGCCAGTGGGGATCC

CGTGTGCAATGCCTGCGGCCTCTACTACAAGCTACACCAGGTGAACCGGCCACTGAC

CATGCGGAAGGATGGTATTCAGACTCGAAACCGCAAGGCATCTGGAAAAGGGAAAA

AGAAACGGGGCTCCAGTCTGGGAGGCACAGGAGCAGCCGAAGGACCAGCTGGTGG

CTTTATGGTGGTGGCTGGGGGCAGCGGTAGCGGGAATTGTGGGGAGGTGGCTTCAG

GCCTGACACTGGGCCCCCCAGGTACTGCCCATCTCTACCAAGGCCTGGGCCCTGTGG

TGCTGTCAGGGCCTGTTAGCCACCTCATGCCTTTCCCTGGACCCCTACTGGGCTCACC

CACGGGCTCCTTCCCCACAGGCCCCATGCCCCCCACCACCAGCACTACTGTGGTGGC

TCCGCTCAGCTCATGAGGGCACAGAGCATGGCCTCCAGAGGAGGGGTGGTGTCCTT

CTCCTCTTGTAGCCAGAATTCTGGACAACCCAAGTCTCTGGGCCCCAGGCACCCCT

GGCTTGAACCTTCAAAGCTTTTGTAAAATAAAACCACCAAAGTCCTGAAA.
```

As used herein, IKZF2 refers to a IKAROS family zinc finger 2 polypeptide. When preparing a T cell or treating a mammal with a T cell, IKZF2 refers to human IKZF2. An example of a human IKZF2 polypeptide includes, without limitation, NCBI reference sequence: NP_001072994.1. In some embodiments referring to a second nucleic acid sequence encoding a IKZF2 (e.g., full length IKZF2) polypeptide, the nucleic acid sequence is at least 70% (e.g., at least 75%, at least 80%, at least 85%, at least 90%, at least 95%, at least 99%, or at least 100%) identical to:

```
                                                  (SEQ ID NO: 10)
GCTAACCCTGCTCCTCGCTGAAGATGGAGGAAGTAAAAACAGGATTACCCTTAGCT

ACAGATCCACTGCCTTAGTTTCCACCACCAACTGCAGTGCACAAACACACGTTAGGC

ACAGGAAAGAAAGAAAGACAGAGGACACATTAACAGTAAACACAAACAAAAGGGT

GATGGGATTATTTTACTGCATGCACTGCTGAGCCCGACATTGTCACCTCCTCTTTGAG

GGGTTAGAAGAAGCTGAGATCTCCCGACAGAGCTGGAAATGGTGATGAATCTTTTTT

AATCAAAGGACAATTTCTTTTCATTGCACTTTGACTATGGAAACAGAGGCTATTGAT

GGCTATATAACGTGTGACAATGAGCTTTCACCCGAAAGGGAGCACTCCAATATGGC

AATTGACCTCACCTCAAGCACACCCAATGGACAGCATGCCTCACCAAGTCACATGA

CAAGCACAAATTCAGTAAAGCTAGAAATGCAGAGTGATGAAGAGTGTGACAGGAA

ACCCCTGAGCCGTGAAGATGAGATCAGGGGCCATGATGAGGGTAGCAGCCTAGAAG

AACCCCTAATTGAGAGCAGCGAGGTGGCTGACAACAGGAAAGTCCAGGAGCTTCAA

GGCGAGGGAGGAATCCGGCTTCCGAATGGTGAACGCCCCTTCCACTGTAACCAGTG

TGGAGCTTCTTTTACTCAGAAGGGCAACCTTCTGAGACACATAAAGTTACACTCTGG

AGAGAAGCCGTTCAAATGTCCTTTCTGTAGCTACGCCTGTAGAAGAAGGGACGCCCT

CACAGGACACCTCAGGACCCATTCTGTGGGTAAACCTCACAAGTGCAACTACTGTG

GACGAAGCTACAAGCAGCGCAGTTCACTGGAGGAGCACAAGGAACGCTGCCACAA

CTATCTCCAGAATGTCAGCATGGAGGCTGCTGGGCAGGTCATGAGTCACCATGTACC

TCCTATGGAAGATTGTAAGGAACAAGAGCCTATTATGGACAACAATATTTCTCTGGT

GCCTTTTGAGAGACCTGCTGTCATAGAGAAGCTCACGGGGAATATGGGAAAACGTA

AAAGCTCCACTCCACAAAAGTTTGTGGGGAAAAGCTCATGCGATTCAGCTACCCA

GATATTCACTTTGATATGAACTTAACATATGAGAAGGAGGCTGAGCTGATGCAGTCT
```

-continued

```
CATATGATGGACCAAGCCATCAACAATGCAATCACCTACCTTGGAGCTGAGGCCCTT

CACCCTCTGATGCAGCACCCGCCAAGCACAATCGCTGAAGTGGCCCCAGTTATAAG

CTCAGCTTATTCTCAGGTCTATCATCCAAATAGGATAGAAAGACCCATTAGCAGGGA

AACTGCTGATAGTCATGAAAACAACATGGATGGCCCCATCTCTCTCATCAGACCAAA

GAGTCGACCCCAGGAAAGAGAGGCCTCTCCCAGCAATAGCTGCCTGGATTCCACTG

ACTCAGAAAGCAGCCATGATGACCACCAGTCCTACCAAGGACACCCTGCCTTAAAT

CCCAAGAGGAAACAAAGCCCAGCTTACATGAAGGAGGATGTCAAAGCTTTGGATAC

TACCAAGGCTCCTAAGGGCTCTCTGAAGGACATCTACAAGGTCTTCAATGGAGAAG

GAGAACAGATTAGGGCCTTCAAGTGTGAGCACTGCCGAGTCCTTTTCCTAGACCATG

TCATGTACACCATTCACATGGGTTGCCATGGCTACCGGGACCCACTGGAATGCAACA

TCTGTGGCTACAGAAGCCAGGACCGTTATGAGTTTTCATCACACATTGTTCGAGGGG

AGCACACATTCCACTAGGCCTTTTCATTCCAAAGGGGACCCCTATGAAGTAAAGAAC

TGCACATGAAGAATACTGCACTTACAATCCCACCTTTCCTCAAATGTTGACATACC

TTTTATTTTTTTAATATTATTACTGTTGATAATTCTTATTTTGTGGAGGCAGTGTCAT

TTGCTCTGCCTAATTACGATAAGGAAGAAACAGAAGAGAGAAGGGGCGGGAATATT

GTTTCTTTATCACCTGGCTTGTTTATTTTGTGGGAATTTAAGAGCAGTCCATTTCTAC

CAAGGCATATCATGCTTTGAAAAATCACTTGATTCATAAAGATTCACCTAAGAGATT

CTGATTTGCCACTGATATTCAGAATTATGATGGAAGACAGGAAAGTTCAGAGTTTTC

TGGGTAGGACTTTGGTGGTTTAAAAATGGTATAAGTAACTTTATTCTTGAAAGAAGA

ATGTGTTTCAAACTGTAAACCAATTTTTTGTTCTTCAGAGATCATGGAACACAAACA

CATTGTTATTTTCAGTGATAACTCCTAAGAGGAGCTGAGTTGTTGTGGGTTCTATGTT

TACTTCCCCTATGGAATTTATAATTCAGTATGTTTTACACTGTACCATATAGCAAAAC

TTTTAAACTACAGGTAGTTAAGGGCCACCTACAATACATCTGAGGTCCTGTGATCTT

ATTTTTCTAAACGTAAGCACTGTTTTTCCATAGTTTTGATGACTGGCATTTTATAGAC

ACCCTGGCAGCCTTACTTTTAACACCTTTAAGGAATAGTATTTTTATGTAGTTTTCAG

AATAACATATGGTCTAAGAGTGGATAAAAGGCAGTCAATAATTTCTGGGAGGGACT

TCTACTTTCATAAATTTGTTTGAGAGGTTTTCTTTTAAAGTTGTAATGTGATGGCAGC

ATAGTATATGTATTTGTTTCTAAAAGTATGCTTACGATTGTCACTTTATCAGCATTTA

ATCAGTGTTAACCAGTCAGCAGAAAAATATAATTATGCTAACAGTAGGGGGAGAAA

ACCCACTTAGAAATCCCTTTTCTGGTATTTCTCTTTTCACTAGTTTTTTTCAAGATGTG

ACCTCCCGGTGTTCTGTCCATAGTTCATTCATCCTTTACTCTTCGAGTAGAAGGTCTT

AAAAGTCTTCCTGTCGGCTGTTTCTTTCAAAATCTCCTCAGAGCAATTGCTAATTTGG

CCTGAATCTGGTAACTTGAACCCTGTAAGGTTACAGAACTAGGGCTATTTATTTTAG

CATTTCTTCAGTAGTATTTACTACTCTTGTTGCAAAGAAAAGGGAATGGGACTTCTTT

GTAACCTGTACCTTGGACAACAGATAAAAGAAACAAAAAAATAAGAAAGTTTACTT

TTACCCTTCTTGGAGTCTAGAATGTGACAGAACCCCCAAAGGAAAGTCCTGCACATT

TTTCTGTTTCCAAAACATTTAATTGTGTAAGTCCTTGTCAGAAATGAATCTCAATCCC

TTAGTATAGAATTCCCCTTACATGGTATAGGTTGCCATATTTCATGTGCAGATTTTAA

TTTCATTTATGTGGGCGCTCTGTTTTTTCTTTGCAGTCCAGCCACATTAGAGGGGAGG

AACCGAGTGATATTGATTCAAGTCATTTTAGGGGGACATACTTGGAAGGCAGAACTT

GCTGCTTCTGTTTGGGGAGGACAGACCTGACTGTGACTGGATTATCTGATAACCATT
```

-continued

```
TGTGAATACTGAAATTCTGTTAGGCAGTAACTGATAACTGCTCTAAAGGATCATTAA
ATAGGATGCTGAAATTATGTATCTTAATACAGTGTGGTATGAGAATTACCAAGTCAA
GAGAATTGTGGACATAAGCAAGTTTGGCCCCAATACTGCTCTTAACTCATTTTCCAG
CTTACTATTTGCTATTTAAATGGTAGGCACCAGCTAAGCACTTCTAAGCACTAACAC
AGCTAGAACTAGGCAAAAATGGTTAGAACTCAGCTCTCTTCTACTAGTCCCTGTCAT
AATTATTTTTGGGAAAATGTCCAAACTGCCCCCTTTAAATCTAAGGGAATGCACCAA
AACAGAGATATATAGAATGTCAACCATTTCATTTTTTTTTTCTGCATGCCTTGGTAC
ATAGTGAACATACAACCTATTTAAAGATAAAGCATGTTTTTGAGACTCGCTCACCCC
CCCCCACCCAACCACTCCCAAATAATAATTGGGATGCCATTTTTTTCCTTTTGGATG
AGGTAAATAATTTTAAGGTTCACAATTTTGTCTTTTACTGCAATTTAAGGAAACATTT
GGATGTCAGTCAATATGTTCATAATTTTGGCTGTGTGCGAATTTCTGCTGGCATTATC
TATGAATTTTCTTCCTACTTATTTTTTTTTCAGTATATGAACAATCATGTATCTACCTG
CCCCAGGATGAAACTAAATTTAGGTGGACCCTAAACCTTATGAAGACAGTGCTGAG
GCACTTTCCTTTTCTGATTTCATCTTTTTGGGAATCTGTTTTATTGAAGGTAGTTAGTA
GTTGAGAGTGCATTTGCTACAAGCATATACTTGTATCTTCCTAGCTTCATGAGGAAC
AGAAAGAGGTGGATATGGCTCAGGGTGTGGCAGGGACAATTGAGGACAAAGTCAAT
TCAAATTTGTGGGTCAGAAAGAATTTTTGTGGACGTAGTGTTTTGGAGAAACTCTG
GATGGTTATATGTGCATGCCTTTTCTTCAAAAGGAAATACGCAAGGTTGTAGCATCT
AAAAATAAACATAAGAGTCAGACACCAAATAAATCAAGTTTTACATAACAGTTGTA
TGCCCAGTTTGTTTAGGTGAGATTTCACATTACAGAAAGTATTTGAGGAGCATGAAA
ATGGGTTATCTTCTGTATTTTCCAGTTTGGCAAAAGTTCAGAATTTCATCACATTGCT
TTGCCCTAATTTTGCCCAGAATTTTATCTTAGCCTCTCTCTGACAGTGATGAATCATG
CTCAAAAGCCATTCTAATTGGACCTTTTTAAGACAGGGAAAGGGATCAGTAGGCGG
ATTGGAAGAAATTTCAAGTCATTGAAATATTCCATTGAGATTTCCTAAAGGGACAAA
ATTGGGAAAATAAGAAACTACGACTTAGATTTGGCTACGTAGTAGAAAGTATCTCCC
CTACATACATACAGGCAATTGTATGTATGAATCATAGGGTATATGTGTGTATACT
ACACACACATTCTTTTAAAGAGAATTCATGGAAAAAAAAGCAGTTGGAGTGATCAG
ATGTATTGCAAAAACATACAGAGAATTTAAATGACAGTTAATACCAAGAAATTAGT
TGGGTTTACTTTATCAGGTCGTAATAGGAATCACTAAAGAAGTTACTAGTGTGTCTT
TAGGACCAGTGGCAACTCTTAAACTAAAACTTTGGGTCCTTATTATCTACTTACAGA
ACAAAGTGAAACAAACAATGATTAAGCTGATTGGATATACATTCAAAGATATTTAA
TGTAAAGTTTTTTGGAATACGAAGAAAATTCAGAAAATAAATATTATCAACAGTTAC
TTATTGGCAAATAGAGAAAGACAAGAATAGTTTAGTGAGCCCGGTATTTTGTTTTTA
TAGTTTTTATCTCAGTTGTACAACTCACAAAACCATGAAGTCTTTGGTATTTTATAAA
TGTTTAACAAAATTTACATCAGATTAAGGCATTTAGATGAAAATTATTATGTTCTCA
CTATCTTCCAAATTTTATTTCATCCTATCTCCAAAATGATTTCTTAGGGTACAAAAAG
AGCAGACGGGGCTGTAAAAATACAAGCAAAAAACTGTGTGCCCCTAGTTTCAGGCA
GAACTTAAACTGTCAGAGGTACTAGCTACATGATTTGTTTTTTAACTTTGGATTGTTC
ACGTCCAAAAATGGATAAATTACATTTGTGTTTATCATCAGTTGCATTTTATGTATTA
TTTTAATAAATACTATCTGAATGAAGACTATTCTAAACCAGAAAATTCCCCAAATCC
AAAAGAAAAAAAAAGTGGGAAGAGGTGAAATTGAAGTTTGTGTATATGAAAGTTAT
```

-continued

```
CTTAGACATATTTTTAATTCTCCAGTTTCTGCAAAATAATTAAAATATACAGTAACTG

GTCTCCTAAATCCTGAATTTAATGTATTAAATACTTATGTTCTTTATATTGGTGCCTTT

TTAAAATGCATTGAGAGTGTTGGTTAGCTGTTGCAGCTGTACAACACTTTTAATATG

CATTTTTAAAAATCACTTAAAATTGAGTACTATATAATTCATCTCTGCATTTTTAGTG

CAAATCTTTAGAGCAATTTCTAATAGAGAAATTTTCAGCTCAGCTGTTAAAAGGAAA

AGGAAACTTTGAAACTAGACTTTACTACCTTTTTAGTTTCATAGTATTTCTGAATATG

ATTACAAGATTATGCAGGTAAAATATAGAGTGAAACTTTACCTGTGAATTGAATTAT

AATTTGTGTTTTTGTTTTGTTTTTAAGGAAGAATAAGTTCTGTATCAAACAAGAATTT

ATTAGATAATTTTTTGGTCAATAAAATACAGTATTCATTTGGATTTTCATCTCCAGAC

TAGTATTGTTCTAGTCTTGGAATCTGTATTTTCTAATCTGTTAGAAAATAGAGATTGA

AAATTGATGGAATAATGTGAAAAAGCAGGTAATTAATTCTCCTTGAACAAAGCAAA

ACTGAACAGTCATATCACATTGCTATTCTCCAAAGCATAATCTCAAATGGTTTCATA

TCATGGTTGTGTATTACTTGCAATGGGTGTGTTAGGATATGACAGCTTTTTAAAAAA

ATGAGCTGCTGGTTATACAAAGCAAATGGCATATGACCAAGAAGCTGTGATATGCT

AGTGTTTCTTTTTATCATAGTGTATTACTAGGCCAAATAATGACACCTTGAATATTTT

TACATTTATTGCAGAAACCTTAAACTTTGGAATTTCCATAAGGTTTTTATGTAATATT

CTATTTCTAGCTTTTTAGTTTTATCTTGCTGTACTGTAAGTTTGAGGATATTTTTCACC

TGCACTCTTAGGAATAAGTTCATAATTCTGTTTATGGGGCTTTCCTCCCATAACACTG

CATTTGTATATTTTCTGTATAAAATATGTGTTGTGTATTAACCTTTATCCCATACAGA

GAGTGGTACATGAATGACTAGTTTTCTAAGATGTCCTTTTTATTGTGAATAAAATAT

AAAAGTTAAAGGCCCTCTGCTAAGTCACATAAAGTACAGCATATAAGTTCATATAG

GTACAAATAAATGAGTTTGCAGTGAATTGGGCCTTCAAATTACCTCAAGTGACAGAT

AGTAAGAAAAGCTTCTTGAGCAGGTGGAGGTCACTGAATCCCCTACTATGCACTTAC

CAAGATTTTACTTACTTTAATTTACTGGAAATTGATTTTTTAAAAAATGACTACACTG

TAACAAGGGAAGGGATCTGGGTTTTTTTGTTGTTTTATTCTTGTTTTTTTTAAGTAGTT

CAAATTCTGAAACTGTGATTTAAAAATTTTTTACAGTCAAGCATTCTGATTTTGAACA

TAACTCCCTTCCCTTTCTGTGTAACAAAGGTCTCTCTGTTATCTCTTAAATTTTGTTAC

ATCTCCCTCAGCCTCTTTCTTTGTCCGTCTCCCTTCTGTCATTGTCTATGGATGTTTAC

CTCTCTGTTCTCCTAAAAGTTTGAAGATTAGGTCAACTCTTATTTCTAGTTCATTGGT

AATTTAATCTTAATTTTTTTTCGTGATTTTTGTTGGTTGTATAATCTGCTGACGTATT

TTTATACTCAAGTGTAGTTTTCTATTAAAAAGAAAAGTGGTTGGATTAAAAATAGTA

AGCTATGTAACCCTCATGTTACTTTCACTTTCAAATATTGGGTACCTAAAACATTACT

TCAGAGATTATGTAATCCTATTATAGTATGTTTGCTTTCCTTTATTGTTGGATTTTACA

TTCTGATTTGGCTTTCCTCCAAAAAATGTATATCATGAAAGACTAGACAGTTATTTGC

AAGTGTTTAGAAAGGTGTTAAAAATGTAAAGCAAAGAGTCTTAACTTTCTCCTAATT

GGGAGAAAAATGCTTTAACATTACTATAATAATATTCCAGGTTTGGAGGGGGTCTCC

AGGCCCCATATTTGCTGTTAATAGTTGGACCTTTTAGACCATGTGTTATTTGCAATCC

CAGAATGATTGCTTCTGCTATTAGTTAAAAAGATACTATTCTTTTCTTTCTGTACAAG

TGCAATACTCCCCTTGAAGTCTTAAAAACTATGGTGATTTTTTTTCTTTTCTGACCT

ATTCTTCCTTTAGCTAATGACAAAAAGAAACTCATAAAAGTCATAGTATGTTAAAGG

ACACAACAAGCAAAGAGAAAAACACTCCACAATCAAAAGATTACAGAATGTGGAA
```

```
-continued
ACCACTAGTCTGATCTCATGGTATCTTTATTTAAGCTAAATTTCCATGGAAATTAGTA

ATC TTTTGCTTGAAAAATGTGTCCTAAAGTTGAACTTTTTACAGATTGAATCTTCTTA

GACCCTCGCCCAATGCTCTAAATTAAGAACCTAATACTTAATATTTTTATTTTACTTC

TCCCCTTTTAGAAATAAACTTTTAAATAAAAGCAAAGCACTTAGCTGAGTTTTAAAC

ACTTACATATCACCTATTGGAGAAATTTTTTTAAAAATATTTGGAGCAGTCCTGTTT

TCATACAAATTTAAGTAAGAGGTATTTTTCTTATACATATTTATATGTAGTGTGCTAA

TTTTCTTTTTTTATACCTGTGTCCCTGTAGTAAAACTGCTGTAATATAAATACATGTTT

TGTTAAAAGATAACATTTCTTTGGCATTTCTTTTAAAGGCAGTTACTGCATTTCTGCA

TTTGTACAGTATGTGTCTTGGCCATTTTAGATATTCTTTCTTTAACAATACCAAAGGT

AATTAGACTATTTTAAAGACTAATTGCTTGACAGTTTCTAGGGTATTTTGTGTTTTAG

AAGCAAAAAAGAAAAAAAAATAGGTCAAACCAGTAAACCTCATTTTTTTTCAAAC

TAATAATTTGGGGAAATAAAAACTATTGTTTAAAAAAGAAATATATATATATATATA

TAAATATATATGTAAAGTTAAAATTCCATACCTTGTATGTCAGGTTTGCTAAGTGTA

ATGTAGTTTTTTTAAGGCTCAAATACCATACCTCAGAAAATGAGGTTTACTATGGAA

ATACTGAAACAGTCTTTGCAGCTGTGTGACAAGTCACTCTACTACATACTGATTTGG

AGACCTCCGCTAAATAGTTTTATCACTGCAGACTAAAATGTGGGACTTGTATCTTCTT

TGTTTTTAATGCACACACATACATGTTCTGTGCATGTATGTGGTTACTGTGTATATGT

GTATGAGTGTTGTATATGCATGTGTGAGTGTGTGTCTGTATGTGTGTACAACTAAAG

AAGCTGCAGAAACTTTGTAATACTTTGTGAAAAGGATTATATTATAAAGGTTTGTAC

TGTCTGAGTGCACAGCTACTGGAATAAATTTAGGGAATCTCAGGAACAAGCATATA

ATTTGTCCAAGATTTATTTCTTCTCAGAAGTGTAAGTGCAGTTTTTAATTCTGTATAT

TATTTAATATTTTACCAATAAAATAAACTTCTGACATAAAAA.
```

As used herein, GATA3 refers to a GATA binding protein 3 polypeptide. When preparing a T cell or treating a mammal with a T cell, GATA3 refers to human GATA3. An example of a human GATA3 polypeptide includes, without limitation, NCBI reference sequence: NP_001002295.1. In some embodiments referring to a second nucleic acid sequence encoding a GATA3 (e.g., full length GATA3) polypeptide, the nucleic acid sequence is at least 70% (e.g., at least 75%, at least 80%, at least 85%, at least 90%, at least 95%, at least 99%, or at least 100%) identical to:

```
(SEQ ID NO: 11)
GAACACTGAGCTGCCTGGCGCCGTCTTGATACTTTCAGAAAGAATGCATTCCCTGTA

AAAAAAAAAAAAAAATACTGAGAGAGGGAGAGAGAGAGAGAAGAAGAGAGAGAG

ACGGAGGGAGAGCGAGACAGAGCGAGCAACGCAATCTGACCGAGCAGGTCGTACG

CCGCCGCCTCCTCCTCCTCTCTGCTCTTCGCTACCCAGGTGACCCGAGGAGGGACTC

CGCCTCCGAGCGGCTGAGGACCCCGGTGCAGAGGAGCCTGGCTCGCAGAATTGCAG

AGTCGTCGCCCCTTTTTACAACCTGGTCCCGTTTTATTCTGCCGTACCCAGTTTTTGG

ATTTTTGTCTTCCCCTTCTTCTCTTTGCTAAACGACCCCTCCAAGATAATTTTTAAAA

AACCTTCTCCTTTGCTCACCTTTGCTTCCCAGCCTTCCCATCCCCCCACCGAAAGCAA

ATCATTCAACGACCCCCGACCCTCCGACGGCAGGAGCCCCCGACCTCCCAGGCGG

ACCGCCCTCCCTCCCCGCGCGCGGGTTCCGGGCCCGGCGAGAGGGCGCGAGCACAG

CCGAGGCCATGGAGGTGACGGCGGACCAGCCGCGCTGGGTGAGCCACCACCACCCC

GCCGTGCTCAACGGGCAGCACCCGGACACGCACCACCCGGGCCTCAGCCACTCCTA

CATGGACGCGGCGCAGTACCCGCTGCCGGAGGAGGTGGATGTGCTTTTTAACATCG

ACGGTCAAGGCAACCACGTCCCGCCCTACTACGGAAACTCGGTCAGGGCCACGGTG
```

-continued

```
CAGAGGTACCCTCCGACCCACCACGGGAGCCAGGTGTGCCGCCCGCCTCTGCTTCAT

GGATCCCTACCCTGGCTGGACGGCGGCAAAGCCCTGGGCAGCCACCACACCGCCTC

CCCCTGGAATCTCAGCCCCTTCTCCAAGACGTCCATCCACCACGGCTCCCCGGGGCC

CCTCTCCGTCTACCCCCGGCCTCGTCCTCCTCCTTGTCGGGGGGCCACGCCAGCCC

GCACCTCTTCACCTTCCCGCCCACCCCGCCGAAGGACGTCTCCCCGGACCCATCGCT

GTCCACCCCAGGCTCGGCCGGCTCGGCCCGGCAGGACGAGAAAGAGTGCCTCAAGT

ACCAGGTGCCCCTGCCCGACAGCATGAAGCTGGAGTCGTCCCACTCCCGTGGCAGC

ATGACCGCCCTGGGTGGAGCCTCCTCGTCGACCCACCACCCCATCACCACCTACCCG

CCCTACGTGCCCGAGTACAGCTCCGGACTCTTCCCCCCCAGCAGCCTGCTGGGCGGC

TCCCCCACCGGCTTCGGATGCAAGTCCAGGCCCAAGGCCCGGTCCAGCACAGAAGG

CAGGGAGTGTGTGAACTGTGGGCAACCTCGACCCCACTGTGGCGGCGAGATGGCA

CGGGACACTACCTGTGCAACGCCTGCGGGCTCTATCACAAAATGAACGGACAGAAC

CGGCCCCTCATTAAGCCCAAGCGAAGGCTGTCTGCAGCCAGGAGAGCAGGGACGTC

CTGTGCGAACTGTCAGACCACCACAACCACACTCTGGAGGAGGAATGCCAATGGGG

ACCCTGTCTGCAATGCCTGTGGGCTCTACTACAAGCTTCACAATATTAACAGACCCC

TGACTATGAAGAAGGAAGGCATCCAGACCAGAAACCGAAAAATGTCTAGCAAATCC

AAAAAGTGCAAAAAAGTGCATGACTCACTGGAGGACTTCCCCAAGAACAGCTCGTT

TAACCCGGCCGCCCTCTCCAGACACATGTCCTCCCTGAGCCACATCTCGCCCTTCAG

CCACTCCAGCCACATGCTGACCACGCCCACGCCGATGCACCCGCCATCCAGCCTGTC

CTTTGGACCACACCACCCCTCCAGCATGGTCACCGCCATGGGTTAGAGCCCTGCTCG

ATGCTCACAGGGCCCCCAGCGAGAGTCCCTGCAGTCCCTTTCGACTTGCATTTTTGC

AGGAGCAGTATCATGAAGCCTAAACGCGATGGATATATGTTTTTGAAGGCAGAAAG

CAAAATTATGTTTGCCACTTTGCAAAGGAGCTCACTGTGGTGTCTGTGTTCCAACCA

CTGAATCTGGACCCCATCTGTGAATAAGCCATTCTGACTCATATCCCCTATTTAACA

GGGTCTCTAGTGCTGTGAAAAAAAAAATGCTGAACATTGCATATAACTTATATTGTA

AGAAATACTGTACAATGACTTTATTGCATCTGGGTAGCTGTAAGGCATGAAGGATGC

CAAGAAGTTTAAGGAATATGGGAGAAATAGTGTGGAAATTAAGAAGAAACTAGGTC

TGATATTCAAATGGACAAACTGCCAGTTTTGTTTCCTTTCACTGGCCACAGTTGTTTG

ATGCATTAAAAGAAAATAAAAAAAAGAAAAAAGAGAAAAGAAAAAAAAAGAAAA

AAGTTGTAGGCGAATCATTTGTTCAAAGCTGTTGGCCTCTGCAAAGGAAATACCAGT

TCTGGGCAATCAGTGTTACCGTTCACCAGTTGCCGTTGAGGGTTTCAGAGAGCCTTT

TTCTAGGCCTACATGCTTTGTGAACAAGTCCCTGTAATTGTTGTTTGTATGTATAATT

CAAAGCACCAAAATAAGAAAAGATGTAGATTTATTTCATCATATTATACAGACCGA

ACTGTTGTATAAATTTATTTACTGCTAGTCTTAAGAACTGCTTTCTTTCGTTTGTTTGT

TTCAATATTTTCCTTCTCTCTCAATTTTTGGTTGAATAAACTAGATTACATTCAGTTG

GCCTAAGGTGGTTGTGCTCGGAGGGTTTCTTGTTTCTTTTCCATTTTGTTTTTGGATG

ATATTTATTAAATAGCTTCTAAGAGTCCGGCGGCATCTGTCTTGTCCCTATTCCTGCA

GCCTGTGCTGAGGGTAGCAGTGTATGAGCTACCAGCGTGCATGTCAGCGACCCTGGC

CCGACAGGCCACGTCCTGCAATCGGCCCGGCTGCCTCTTCGCCCTGTCGTGTTCTGT

GTTAGTGATCACTGCCTTTAATACAGTCTGTTGGAATAATATTATAAGCATAATAAT

AAAGTGAAAATATTTTAAAACTA.
```

As used herein, NFATC2 refers to a nuclear factor of activated T cells 2 polypeptide. When preparing a T cell or treating a mammal with a T cell, NFATC2 refers to human NFATC2. An example of a human NFATC2 polypeptide includes, without limitation, NCBI reference sequence: NP_001129493.1. In some embodiments referring to a second nucleic acid sequence encoding a NFATC2 (e.g., full length NFATC2) polypeptide, the nucleic acid sequence is at least 70% (e.g., at least 75%, at least 80%, at least 85%, at least 90%, at least 95%, at least 99%, or at least 100%) identical to:

(SEQ ID NO: 12)
GCGTTGCCTCTGGAGTAAGCCGGATCGCGGAGCCGCGCCGACTCCGCCGAGCCGGG

AGCCGGGAGGCGCGCAGCTCCCGGGTCGCTCCGAGGCTCCTCGGCCAGGGCAGCCC

CGCGGGCACGCGGTAGAGAAGACGGCGTCCCCTCGGCTGCTGGTCGATACAAACAG

ATCCCCCTTTCCAAACACGCGCCAAGTCCCCGTGCCCTCCAGATGCAGAGAGAGGCT

GCGTTCAGACTGGGGCACTGCCATCCCCTCCGCATCATGGGGTCTGTGGACCAAGAA

GAGCCGAATGCACATAAGGTCGCCAGCCCACCCTCCGGACCCGCATACCCCGATGA

TGTCCTGGACTATGGCCTCAAGCCATACAGCCCCCTTGCTAGTCTCTCTGGCGAGCC

CCCCGGCCGATTCGGAGAGCCGGATAGGGTAGGGCCGCAGAAGTTTCTGAGCGCGG

CCAAGCCAGCAGGGCCTCGGGCCTGAGCCCTCGGATCGAGATCACTCCGTCCCAC

GAACTGATCCAGGCAGTGGGGCCCCTCCGCATGAGAGACGCGGGCCTCCTGGTGGA

GCAGCCGCCCTGGCCGGGGTGGCCGCCAGCCCGAGGTTCACCCTGCCCGTGCCCG

GCTTCGAGGGCTACCGCGAGCCGCTTTGCTTGAGCCCCGCTAGCAGCGGCTCCTCTG

CCAGCTTCATTTCTGACACCTTCTCCCCCTACACCTCGCCCTGCGTCTCGCCCAATAA

CGGCGGGCCCGACGACCTGTGTCCGCAGTTTCAAAACATCCCTGCTCATTATTCCCC

CAGAACCTCGCCAATAATGTCACCTCGAACCAGCCTCGCCGAGGACAGCTGCCTGG

GCCGCCACTCGCCCGTGCCCCGTCCGGCCTCCCGCTCCTCATCGCCTGGTGCCAAGC

GGAGGCATTCGTGCGCCGAGGCCTTGGTTGCCCTGCCGCCCGGAGCCTCACCCCAGC

GCTCCCGGAGCCCCTCGCCGCAGCCCTCATCTCACGTGGCACCCCAGGACCACGGCT

CCCCGGCTGGGTACCCCCCTGTGGCTGGCTCTGCCGTGATCATGGATGCCCTGAACA

GCCTCGCCACGGACTCGCCTTGTGGGATCCCCCCAAGATGTGGAAGACCAGCCCTG

ACCCCTCGCCGGTGTCTGCCGCCCCATCCAAGGCCGGCCTGCCTCGCCACATCTACC

CGGCCGTGGAGTTCCTGGGGCCCTGCGAGCAGGGCGAGAGGAGAAACTCGGCTCCA

GAATCCATCCTGCTGGTTCCGCCCACTTGGCCCAAGCCGCTGGTGCCTGCCATTCCC

ATCTGCAGCATCCCAGTGACTGCATCCCTCCCTCCACTTGAGTGGCCGCTGTCCAGT

CAGTCAGGCTCTTACGAGCTGCGGATCGAGGTGCAGCCCAAGCCACATCACCGGGC

CCACTATGAGACAGAAGGCAGCCGAGGGGCTGTCAAAGCTCCAACTGGAGGCCACC

CTGTGGTTCAGCTCCATGGCTACATGGAAAACAAGCCTCTGGGACTTCAGATCTTCA

TTGGGACAGCTGATGAGCGGATCCTTAAGCCGCACGCCTTCTACCAGGTGCACCGA

ATCACGGGGAAAACTGTCACCACCACCAGCTATGAGAAGATAGTGGGCAACACCAA

AGTCCTGGAGATACCCTTGGAGCCCAAAAACAACATGAGGGCAACCATCGACTGTG

CGGGGATCTTGAAGCTTAGAAACGCCGACATTGAGCTGCGGAAAGGCGAGACGGAC

ATTGGAAGAAAGAACACGCGGGTGAGACTGGTTTTCCGAGTTCACATCCCAGAGTC

CAGTGGCAGAATCGTCTCTTTACAGACTGCATCTAACCCCATCGAGTGCTCCCAGCG

ATCTGCTCACGAGCTGCCCATGGTTGAAAGACAAGACACAGACAGCTGCCTGGTCT

ATGGCGGCCAGCAAATGATCCTCACGGGGCAGAACTTTACATCCGAGTCCAAAGTT

GTGTTTACTGAGAAGACCACAGATGGACAGCAAATTTGGGAGATGGAAGCCACGGT

-continued

```
GGATAAGGACAAGAGCCAGCCCAACATGCTTTTTGTTGAGATCCCTGAATATCGGA
ACAAGCATATCCGCACACCTGTAAAAGTGAACTTCTACGTCATCAATGGGAAGAGA
AAACGAAGTCAGCCTCAGCACTTTACCTACCACCCAGTCCCAGCCATCAAGACGGA
GCCCACGGATGAATATGACCCCACTCTGATCTGCAGCCCCACCCATGGAGGCCTGG
GGAGCCAGCCTTACTACCCCCAGCACCCGATGGTGGCCGAGTCCCCCTCCTGCCTCG
TGGCCACCATGGCTCCCTGCCAGCAGTTCCGCACGGGGCTCTCATCCCCTGACGCCC
GCTACCAGCAACAGAACCCAGCGGCCGTACTCTACCAGCGGAGCAAGAGCCTGAGC
CCCAGCCTGCTGGGCTATCAGCAGCCGGCCCTCATGGCCGCCCCGCTGTCCCTTGCG
GACGCTCACCGCTCTGTGCTGGTGCACGCCGGCTCCCAGGGCCAGAGCTCAGCCCTG
CTCCACCCCTCTCCGACCAACCAGCAGGCCTCGCCTGTGATCCACTACTCACCCACC
AACCAGCAGCTGCGCTGCGGAAGCCACCAGGAGTTCCAGCACATCATGTACTGCGA
GAATTTCGCACCAGGCACCACCAGACCTGGCCCGCCCCCGGTCAGTCAAGGTCAGA
GGCTGAGCCCGGGTTCCTACCCCACAGTCATTCAGCAGCAGAATGCCACGAGCCAA
AGAGCCGCCAAAAACGGACCCCCGGTCAGTGACCAAAAGGAAGTATTACCTGCGGG
GGTGACCATTAAACAGGAGCAGAACTTGGACCAGACCTACTTGGATGATGAGCTGA
TAGACACACACCTTAGCTGGATACAAAACATATTATGAAACAGAATGACTGTGATCT
TTGATCCGAGAAATCAAAGTTAAAGTTAATGAAATTATCAGGAAGGAGTTTTCAGG
ACCTCCTGCCAGAAATCAGACGTAAAAGAAGCCATTATAGCAAGACACCTTCTGTAT
CTGACCCCTCGGAGCCCTCCACAGCCCCTCACCTTCTGTCTCCTTTCATGTTCATCTC
CCAGCCCGGAGTCCACACGCGGATCAATGTATGGGCACTAAGCGGACTCTCACTTA
AGGAGCTCGCCACCTCCCTCTAAACACCAGAGAGAACTCTTCTTTTCGGTTTATGTTT
TAAATCCCAGAGAGCATCCTGGTTGATCTTAATGGTGTTCCGTCCAAATAGTAAGCA
CCTGCTGACCAAAAGCACATTCTACATGAGACAGGACACTGGAACTCTCCTGAGAA
CAGAGTGACTGGAGCTTGGGGGGATGGACGGGGGACAGAAGATGTGGGCACTGTG
ATTAAACCCCAGCCCTTGCGTTCGTTTTTCCAGGTCACAGATACAGCTCCTGTACCTT
TTGAAGGCAAGGAGTTCTCAGAGCAACCAAAGGAACGTGACCCAAGAGCCCAGCTT
ACAGGCTGAAGAAACCCAAAACCCTCGATAGAGACAGAAACTGAACTGTCAGTCCT
TAGAGCTCGCCCAGTCCATGCCACAACTGGGCCACAGCTAAAGCTTTATTTTTGAAT
TCTCATTCCAAAACCAAACTGTCTTGCCCAGACAAGATCACCTGTTAAGACTTCTTG
GCGTTAAGTTATGACATGTATACGCGTTTGTTATTATTATTTTTTCTGCTTTAAAAGG
CTGACCAGGGCACCTAGCCCTGGAGCTGTCTTGGCGAGCTGTTCTTTAACCCCTGCA
GCACGCAGTCCTGCTAACACAATTTCCATAGACTTGGGGGGCTGACCCAGGCTGCA
GAGAGCAAGCACCTGTCTGCTGCAGCTGTACAACCTGGATGCTTTGCAAGGTTCCGG
CTTGCTTTCTTCCTAGCAGCCAGAGTGCTTTTCCGTAAAGCGGTGGAGAATCTCAAG
CATGTGCATTTAATTGAGGAATAGCAGAAGGGCTAAAGCAACCAAGAAAAGAAGTG
TGGGTATTTTTGTTAAGTAAAACAGCCCAAGTGCTTCTGGAGGTGGGTTTCTACCAA
GATAGAGGAAAAGGGCTGAATTCCCTCTAAGTGGGACAGCCGAGCTCAGGATGTGC
TTCCCAGCTTCACTGGTTAATTTGACCTGAACCTATTTAAAGATCCCTTCTGCCCCTG
AAGACCTATCCGCACTCAAATTCTAACATGAAGAAATCTACTCGAATGCATCCTTTA
CTTTGAATGAGCTCTATTCGGTTGCATGTTATATGTGATTTCCTTCCTCCCAACTGTTT
CCACTGAGCGCACCCAGTCTCCCCTAGTCTTCCTCTGTGGGTGTGATTTTTGTGATTT
```

-continued

```
TTACAAACAAAACCCTTGAAGTTCTTGGCAGATGTGTTTGTTTCTGTTTGCATGTACT

GCAGATACCCCAGGACAAGCGGGGGATTCATTTTTCAGCCATTCAGTTGTTTCCTCA

ATAATCCGCAGCAAAGTGAAAATATTCTTAGCACTCAGACTGTACTTAGAGTGTTTT

CTCAGTCCAGTCTGTACAGTCTGTAGGCAGAAGGCCTCAGAAGAAAGTCATGGCCA

CTCAGTGCCCACTGTGGGCTTTGTAAGTCCTGGCTCTCCCGTCAAGGTTACCCAGAG

GTAAAAGCTTCCTGGGAGTGGGGCCAGGTGTGTTTGGCACTCCAGATAGAAGGCAA

AATGCTCAGATTCGGGCCTGTGCACTTGTATGCAACCTGTCGGTCGATACCTAGCAT

TTATTTTTCCCTGACAATGAACGACCTTTCCCTCACCCACCCTAAGCTCAAAGAGTTT

AGCAAAATTCTCTTTTAAATAAACAGAATGCCAGTAAGAGGTTGACCCCTACCATGG

AACTTCTGGGATGCTAAATACTTCCTCATGAACAAAATAAGTTCCTTATTATAAGTT

CCTTATACTAGCAGCTTCACCTAAAGAATTTTCTCTCCAGCAATATTGACTTCACTGG

GGAAAAGCCAAGAGTGTGTGGTGAGTGATTTGTTCTCACTCGACCTGGCTAGGACTG

GCTAGGAGCTGTTTTTTGTACATGAGGGAATTTGGGCTTTCCTCAGTTATCTGAATGT

TTTACCCAAGTGCCTTCCTGCTATTGTAGCAAAGTAGCTCAGCTTCCTTGTCCACAGG

GTGAAAAAGGACTAATGCATTTTCCATCAGTTTTCTAACTATGTTAGCAAAAACGGC

CTCCTGGTAGCTCAACCTCCTGTACGCGTGTGTGTGTAATACACACACAAATAAA

CCCCTCTGTTTTTCTAAGACATCTTAGCTGGATATTATAGGAAGCACTTTCATAAACA

ACTGTAACAAATCGCAAAGGAAAGAGAAACAAAAGCATTAGATTTGAGACATAAAC

AGGCAAGAGAAAGTGTATTAGGAACTGACAGCTATCAAGGAAGTTTTGTCAGTTAC

AAATGCTAGGAGGAAATTTTGCCAAGAAGGATGGCTCATGAAATATTTCCAGTACG

GGAAGAGGCAATAAGATCCTCTAAGAGAATGAGAAAGTAGGGGTGTCTAAATGGTA

AAGATGGGTGTGTTGCACGTGTGTTAGAAGGATCTCAGTTGAGTGAAGGTTTGCACT

GCTACATCTAAGTTAATGTAAATATGTAGCACTCTGACAGGTCTACCGTGTTGCTGA

ATGTAGTATATTTCCAAAGTTTGCAAGTCTTCCTGTATTGTACAAAGATGCTGCTGCT

TGATAATATGTATAGCAATCCAGATTAGTATGTTATTAAATTTTATTTTCTTACCTGT

ATTTTTATGCTTTTTACCTGTCCTCAAAATATTACACCCCTGTTGGAATTAGATTTAT

ATTTATAAATGGTCAGAAATCTTTTTAAGTGTCTCTTTTTACACATAGGTTGATTTTT

TTTTCTTAAGAGAAATGATGTATTCTTGAAACATTTGTTACTCATTCCAGGAAACAA

AAACCCATATAATAAAACCCCCACTCAGAGCCTGTTAGTCACCTCTCTAGAAGATGG

CATCTCAGGAGAAGGAATGGCTTTGTGGAAGAAGGAATCACCTTTTTCTTGCTCAAG

AATTATGCTGACTTCAGCCCTGAGCCTGGATCTGGTCACTGAGAATCATCAAGTGTC

TAGATCCTCCCCCCAAAATAACTAATTTAGTAGGTGATTTTGATTTAAAAAATTGA

CACCAAAACCCTGCCTGCATTGTAATGGAATTCGAAAAGAATTCATGTTCACAGAAC

TCAACGTTCAGGCTAATATTTACAGAAGGGACCAAATCTAAATCCTGGTAGATAACT

CCTGTATGCTTTATCCAAAGGACACCCACAGTTTTCCAGCATAGATATAACCAAGGA

TGAATTGATTCCTTCAAAGAACTGGGAGGCACGGATATTGCATTTTTTGTTTACATCC

AGTAGCCAAGACGCCTCAGTGAGCCAGTCTTGGGCAGAGGCTGTCACATTTAGGCA

GATTGGAAGTTGGTATGTTCTAATTCTCACTCTGGACTACAGTGAGGCTGAATTTAT

CATGTCAAAAAAAAAAAAAAAAAAAGACCTTTCCAAGTGCTTTCTATTGCTCAGAA

TTGAAAGAATGTTTTCATTTCAAGTTTACAAGAGGCATGGATGGAGTTGTGACGTTC

TTGACAAGCTGGGCTAACCTTTCCCGAACTTGTTTCCCGGAGGCAAGGTGCTCGGTG
```

-continued

```
ACCCAGCGCATCTTAACCTTGGGTCTCCTAGGCTCGAGGCTAGGGCATTACGTTTCG

TGGAACCAAAGCAGCCAATTGCATAGCAAGTATTTTCCTGCATTCCAATTAAATGCT

TAAGAAAAAGCAGCATCCTATAAAATTGTGATCATAAACATCCATTTCCCTCAGCTT

TTGTGAGTGCCTTGACTTACAGCCAACATCACTGTTTAACTCAGTCTGTTTAAAAAC

AAACTTTTCTGGTGGTTGATAACAGAGAGTTGCTCCCTGAGCCATCAGGGTCCTGGG

AGCTGGAAGTGAAAGGGTTATTAACATTCTACCTTTATGCAGCTGTTGGCTGACCAG

AATAAACTCCCTGCTGAGTTCAAGCTTTGAATGGAATGGATGCAAATGATGTTGTTT

CCATTAGAGCAGGTGCTCACAGCATTCTGATTGGCCTGAGCAGACCGAGGCTATGGC

TGTTGGGACAAGCTTAGCATCCTGGACATCTTGTCAAAGAACCTCACTCACCCCTCT

GGCCTCTACAGCCCTCAGAGGAGAGAAAACCAATTCTCCAACAAACAGGTCTCTCC

AACATGGTGGTGCTGGCAGGCTTAGGTTTAGAAAATCCTGACTGTTAAAGGCGTTTG

AATACATCACATTCCTATGCAAATGTTTTTAATCTCCAGTTTAATGTAGTTTATTTTT

CCTATATGTAAAGTATTTTTATACGGCTTGTATCATGATAGTTTAGCAATAAAACAG

TTGGAAGCAA.
```

As used herein, XBP1 also known as refers to an X-box binding protein 1 polypeptide. When preparing a T cell or treating a mammal with a T cell, XBP1 refers to human XBP1. An example of a human XBP1 polypeptide includes, without limitation, NCBI reference sequence: NP_005071.2. In some embodiments referring to a second nucleic acid sequence encoding a XBP1 (e.g., full length XBP1) polypeptide, the nucleic acid sequence is at least 70% (e.g., at least 75%, at least 80%, at least 85%, at least 90%, at least 95%, at least 99%, or at least 100%) identical to:

```
                                          (SEQ ID NO: 14)
GAGCATGCTCCCGCTGCAGTTAACTAGCCCAACCTATTTCTTTAATTCAGCCCATCCC

TTCGTTTCCCTTAAGGGATACTTTTAGTTAATTTAATATCTATAGAAACAATGCTAAT

GACTGGTTTGCTGTTAATAAATATGTGGGTAAATCTCTGTTCAGGGTTCTCAGCTCTG

AAGGTTGTAAGATCCCTGATTTCCCACTTCACACCTCTATATTTCCTTTTTTTTTTTT

TTTTTTTTGAGACAGAGTCTCACTCTCGCCCAGGCTGGAGTGCAGTGGCACGATCTC

TGCTCACTGCAAGCTCCGCCTCCCGGGTTCACGCCATTCTCCCGCCTCAGCCTTCCGA

GTAGCTGGGACTACAGGCGCCCGCCACTACGCCCGGCTAATTTTTTGTATTTTTAGT

AGAGACGGGGTTTCACCGTGTTAGCCAGGATGGTCTTGATCTCCTGACTTCGTGATC

CGCCTGCCTCGGCCTCCGAAAGTGCTGGGATTACAAGCGTGAGCCACCGCGCCCGG

CCTCACACCTCTATATTTCTGTGTGTGTGTCTTTAATTCCTCTAGCACTGCTGGGTTA

GGGTCTCCCTGACCGAGCTGGTCTCGGCAGATAAGGTTTCACCATGTTGGCCAG

GCTGGTCTCAAACTCCTGACTTCAGGGGATCCCCGCCCCAGCCTCCCAAAGAGCTGG

GATTACGGGCATGAGTCACCGTGCCCAGCCAATTTTCTTTTGTTTTTTCTTTTGAGAC

AGGATCTCACTCTGTCACCCAGGCTTGAATGCAGTGGTACCATCTCGGCTCACTGCA

GCCTCAATCTTCTGGGCTCAAATGATCCTCCCACCTTAGCCTCCCGAGCAGCTGGGG

CTACAAGTGCACACTACCAAGCCCAGCTAATTTTTTTTTTTTTTTTTTTTGAGAC

AGAGTCTTGCTGTGTCCCTCACCCAGGTTGGAGAGCAGTGGTTCGATCTTGGCTCAC

TACAACCTCTGCCTCCCGTGTTCAAGCAATTCTCGTGCCTCAGCCTCCTCAGTAGCTG

GGATTACAGGCACGTGCCACCATGCCCAGTTAATTTTTGTATTTTTAATAGAGACGG

GGTTTCGCCATGTTGACCAGGCTGGTCTTGAACCCCTGACCTCAGCCTCCCAAAGTG

CTGAGATTACAGGTGTGAGCCGACATGCTAGGCCTATACATTTCAAAATTATGTTGC
```

```
-continued
TATGTTCATAAAGATGTATATATGGTAACTTGTACCTTCAATCAACATGAAATACC

CTTCTTTGTCCTTTTAATGCCTTTATGATAAATTCTGTCTCATATTAATATTGCTACAT

ATGCTTTCTTTCCATAAACATTTCCATAAACATAAAAATGGCTGGTAAGTCATTTTCC

TTTTTTTAAAAAAATTTTTGTTTTTTAGAGGCAGGAGCTCATTCTGTCTCCCAGGTT

GGAGTACAATGGTTCAATCATAGCTCATAGTTTACTGCAGCCTCGAACTCCTGGGTT

CAAGGGATCTTACCACCTCCGTCTTCCGAGCAGCTGGGACTACAGGTGCAAGTCACC

ACGCCTGGTTAATTTTTTAAATTTTTTGTAGAGACAAGGTCACAATATGTTTCCCAG

CCTGGTCTTGAACTCCTGGCCTCAAGCAATCCTCCTGCCTTGAGAAATATAGTAAAC

AAAAAATGTGAAATAACATGGCAGAAATAAGTCCAAATAAATAAATAATCAAAAAT

AAATACAAATGATTTATATTCTCTTCTTAAAAGAGAGCTCTGAGAAACCCCAAAGCC

AGCTATATGTTGTTTATAAAGAGACATACATAAAACAAAACAGCATGATTAAGAAG

ATAATATAACCCATTCACATTTATGTTTTATTATTTATATATTTGGACTTATTCCTG

CCATGTTATTTTCTGTTTTCTGCTTACCAGTGTACAGTATTTTTCTGTTTTCCCTTTTCT

GGAATGCCTATTTATTTCTGTTCCTGTTTTGTCCACCCTTTCCTGACTGATTCTTTCTG

AATAATGACTTTTTTTTTTTTTTTTTTTTTTGAGAAAGTCTCACTCTGTTGACCAG

GCTGGAGTGCAATGGCACAATCTTGGCTAATTGCAACCTCTGCCTCCCAGGTTCAAG

ACATTATCCTGCCTCAGCCTCCCCAGTAGCTGAGATTACAGGCGCCCCCCACCATGT

CCGGCTAATTTTTGTATTTTTAGTAGAGACTGGGTTTCACCATGTTGGCCAGGCTGGT

CTCGAACTCCTGATCTCAGGTGATCTGCCCACCTCGGCCTCCCAAAGTGCTGGGATT

ACAGGGGTGAGCCACCGCGTTTGGCCTCAAAGACCGAGAACTTTGTAATTTATATAT

TTTATAGCTCTTATCACAGGTGTCTAGTAAATATTTTTAAACACTTATGGCACCTGAT

GCAAGAATTACCAGGTTCATTTTATAGAGAGGATATGAAACTGTCCAAGGGTTTGGA

CTCACATGTTCAAGACTGCATGGACAGCAATCTGTAGTGGGTCAAATTATTGTTTTT

AGTATGATTTAAAGTGTTTGTCAAAAATATAAAAGTTTTGAAAACAAGCTGGGGAA

GTGAATTTCAATATCGCATTAACTAAGATCAAAGTGCAATTCATCAACCTTTTTTCCC

CATCCCGCACCCTGTGCTTTCTCTACTCAGTTACTCACTACACCCTGCTGGACTAAAA

GGGTCCTCCAGCATTTTCTTTCTTACACAGTGAAAGACATTCTCTTGGCATTAATAAA

TGTTCACTTAATAAATAAAAAGGGCCGGGCTCTGTGGTTCCTGCCTGCAATCCCAGC

AGTTTGGGAGGCCAAGGCAAGAGGATCGCTTGAGCCTAGGAGTTCCAGCCTAGGCA

ACGTGGCGAAACCCAGTCTCAAAAAAAAAAAAAAGGAAAAAAAAGGCATCAAAAA

ATAAAACGTAACAGGTGGCATGACATGACATGACTTTTCTAACAGCCTCTTACAGCT

TTCCAAGGTCTTTTAATATGAAGCTATAGGTCTCGGCTAGAAGACACCTCCAGACTT

CTCCCAAAACATTTCAGAGGCCCGGAGTAAGTCTCCCCACATCTGAAGGCACATCA

GAACCCAGGTGGCCCAAGCTGATGAGAGTTAAACAGGAAGTTGGTTTCTTGGTCCG

GCAGAGACTCCAATCACCCCCACCTCTTTTCCAACCCACAGGACAGCACGTGCTCAG

GAGGCTCTGGAGTTGGGACAGCCCAGTTAAAAAAAAAAAAATCATTGATTTCCCTC

CCAACGAAGAGGGAGAAAACACGTTAGGAGACTCGTGGCCCAGTCCTGGCAAAAA

CCAAAACTATGTCCCTTTAGAGGGCTTAGATATCAAGAGATGGACTTGCTTTTAGTT

CTTTTTCCCATCCTGTTCCCTCCCTACCAAAATAAAATTGACCAGCTAATCCGACTTA

ATAACACTAAAGAATTACTTAGGAACCTGCTATCTTAACATTTCACTTTTTGCATATC

CTCCAAATACCAGGTAGCAGTCTTACTACTGTTTGCACCCCTAGAACCTGGAATAGT
```

-continued

```
GCTGCCCGCAGAGGAGGAAGCAATAATTACTTGTTAGAGAAGGTATTGCTGTGCATT

TCTGGGGAATTTCACATTTTGTAATTTGCTTTAAAAAAAGTGGACAGGCATATTTAC

GGGGGTTTCTCGGACTTCTCCATGTTAATATTCGTGTGTATAAATCGCTCCCGTGCTG

CTCTCTGGGGGCCCCTCTTTCACAAACACCTGGCCACCCTCACGCCACAATGGCCAG

GCAGGAACCTCGACCTCCCCTCGGAGAGGGGGCTCAGGGTCAACCCCGGGGTCTCA

GTCTCTACATGTGACGTTTTCCTGTCCCCTCATTTAAAATAACAAGAGGCTGGGCGC

AGTGGCTTACGCCTGTAATCCCAGCACTTTGGGAGGCCGAGGCGGGCGATCACGAG

GTCAGGAGATGGAGACCATCCTGGCCAACACGGTGAAACCCCGCCTCTACTAAACT

ACAAAAAATTAGCCGGGTGTGGTGGCGGGCGCCTGTAGTCCCAGCTACTCGGGAGG

CTGAGGCAGGAGAATTGCTTGAACCCGGAGGCGAAGGTTGCAGTGAGCTGAGATCT

CGCCACTGCACTCCAGCCTGGTGACAGAGCCTGACTCCGTCTCAAAAAATAAGAAA

AAAAAATAAAATAAAAATAATAGAGGCCGAAGCGGGAGGTTCACTTGAGCTCAGA

AGTTCGAGATCAGCCTGGGCAACACAGTGAGACCTCGTTTCTATTTAAAAAATAAAA

TAAAACTAAATTTAAAAAAATGCACGCTCATAGTACAAACTTTAGAAATGGAACGA

AAAACTAAAATTGAAGGTATTCCCCTCCAACCCAGAGATAACACCTATCGTTTATTA

AGCCCTCACTATTGTTAAACTTAGTTTTAAAGGGCACGATCTCATTTCTTAAAGACTT

CTATTCCGCAGAATTTCTTTCCAGGCTTTTTTCTTTTTCTTTTTTGAGACGGAGTCTC

GCTCTGTCGCCCAGGCCGGGGTGCAGTGGCGCGATCTCGGCTCACTGAAACCTCTGT

CCAGTCTTTTCGAACCCAAGGCCCAACTGCGCTCTATCTCGACTTTCGGCTCCACTCG

GATCCCGAAGTGGCGCACGAGATAAAATGTTGTCAGGCTGAGGTAATTCTCTGTTAG

TCCCGGTAAAAATTCGTCAGTCTGGAAAGCTCTCGGTTTGGAATTAAATTCTGTCAC

TCCGGATGGAAATAAGTCCGCTTAAGGGGGGAAAATCCGTTTGTGGAGGACACGCT

CCCGCACGTAACCCCCCGCGGAAAATGACCCCAAGTACCTTTGGCCAGGGATTGCC

GCTGCCACGCCGGACTCCATAGCCACGGTCCTGAAACGCCCCGCCGGGCAGGCCGG

ACCAATGGACGCCGAGCTCGGCCGTGCGTCACGCGACGCTGGCCAATCGCGGAGGG

CCACGACCGTAGAAAGGCCGGGCGCGGCGAGGCTGGGCGCTGGGCGGCTGCGGCG

CGCGGTGCGCGGTGCGTAGTCTGGAGCTATGGTGGTGGTGGCAGCCGCGCCGAACC

CGGCCGACGGGACCCCTAAAGTTCTGCTTCTGTCGGGGCAGCCCGCCTCCGCCGCCG

GAGCCCCGGCCGGCCAGGCCCTGCCGCTCATGGTGCCAGCCCAGAGAGGGGCCAGC

CCGGAGGCAGCGAGCGGGGGCTGCCCCAGGCGCGCAAGCGACAGCGCCTCACGC

ACCTGAGCCCCGAGGAGAAGGCGCTGAGGAGGTGGGCGAGGGGCCGGGGTCTGGG

GCCAGATCTGAAGCCGGGACTAGGGACAGGGGCAGGGGCAGGGCTGGGAGCGGG

GACCCAGCACTGGCCGCCCCGCAGGGCTCCGTCGCCTTTGGCCTGGCGGGTCGGTGC

CAGCGTGGCGCGGGCGGGGCAGGAAGCCCGGACTGACCGGATCCGCCACGCTGG

GAACCTAGGGCGGCCCAGGGCTCTTTTCTGTACTTTTTAACTCTCTCGTTAGAGATGA

CCAGAGCTGGGGATGCGGGCACCTGTCTTCCAGGCCCTCTTGCTGTGTGGCCGCAGA

CTGGTGGTTCAGCCTCTTAACTCGGACATGAGGTCGAATAATCTGTTTTGGTTTACTG

CTATTTCTGGAGAGGCGCGGAGCTGAAATAACAGAGCTGTTGAAAGGGCTGGGAAT

TCTGCGAGGCTCACTGGTCTAGCTCAGTATCTGCGTTCTTAAAATGGAACCTACTTC

ATGAGGTCTTTGGGGAGATTGAGACTTGGATATAATGTGCCTAGCACTTAGTCCTCC

GTAAATGTTCACTCTTTTGTGATCATTGTGCCTTCTGTGATTTATGAAGTGTCTCTTCT
```

-continued
```
GAGTTAATTCTTTTAAAAAAAAAAGTGTCTCCTCCAACAGACACGGACCCATCAGCA

GGTCACTGCCTAGGATCTCAACACTAGAGATCAGGGAGTGGCATCAGCCTCTCCCTT

TTCTAAATTGGACTGGGGGACGGAGGGTTGATGTCATAGCAAGATTGCAGCCTTCAC

TAGATTAATGAGGCCAGGTTGGATCCTGTTTAAGAGAACTGGAGACAGGAAGCAGC

GGGGGAATAGATGGGGAAAGAGGAAAGTTCCTTATGATGCAAGATGAATAGTGTGT

GTGTCCAGCCCCAGTGCTGTGACGGGGATGAGTCTGAGGTGGACGGATGATGCAAT

ATAGGAGAGAATAAAGCAGGTCTTCGAGCTAGATTGACAGAAGACTGTATTTTTAT

TTTGTTTTATTGAGGGGAGGAGCCTGAAGTGTATTTTATCATTAGTCTGTCTTATACT

GTAAATAAAAATGAAAGCACCAGCTGGTAAAGTTTTCAAATAAAGACATAAATAAG

GTTTGATATGACTCAGTGTGGTATGTTCCTTCTCTTCCTAGGAAACTGAAAAACAGA

GTAGCAGCTCAGACTGCCAGAGATCGAAAGAAGGCTCGAATGAGTGAGCTGGAACA

GCAAGTGGTAGATTTAGAAGAAGAGGTAAAACTACTTAAGGTCAAACTCTTTTATCC

ATTGTATACCCTTCCTTGGTGAATGTTCTGATATTTGCTTCCCATCCCAAGTTGTTTC

AGCCCCTATTAGAATACAATTGAATATATGATTAAAAGTTAAACTAGGCTGGGCATG

GTGGCTCATGCCTGTAATCCCAGCACTTTGGGAGCCTGAGTTGGGCAGATCACTTGA

AGCCAGCAGTTTGAGACCAGCCTAGCCAACATGGTAAAATCCCGTCTCTACCCAAA

AATATACCAAAAAAAAAAAAAAAAAAAAGGCCAAGCGTGAGTGCCTGTAGTCCCA

GCTACTCGGGAGGTTGAGGTGGGAGGATTGTTTGAACCTGGGAGAGGGAGGTTGCA

GTGAGCTGAGATCGCACCACTGCACTCCAGCCTGGGCAACAGAGTGAGACTCTGTC

TCAAGAAAAAAAAAAAAAGTTTGCTGGGCACCGGGGCTCACACCTGTAATCCCAGC

ACTTTGGGAGGCCAAGGTGGGTAGATAACTTGAGATCAGGAGTTCGAGACCAGCCT

GACCAACGTGGTGAAACCCCATCTCTATTAAAAATACAAAAATTAGCCGGGTGTCGT

GGCAGGCACCTGTAATCCCAGCTGCTCCGGAGGCTGACGCAGGAGAATCACTTGAA

CCCAGGAGGCGGAGGTTGCAGTGAGCTGAGATCACGAGATCATGCCACTGCACTCC

AGTCTGGGCGACAGAGCAAAAACCCTGTCTCAAAAAAAAAAAAAAAGTTAATCTAA

GTTAGGACAGAGAGTTGGTGAAGTGGTGAAGCTTGTTGAGGGCAGAAGTGATTGAC

TTTGTGGCATTTGGTGCTAGATGTATCTCAAAGTAGATGGATTTAACAATGTTTATTG

AGTTTGTAGTAAGAAATTAGCAAGGGCTAATAGGAAATAATTGCTTAAACTTTACAT

TCTTCCTGGCATGGCCAGAAATTCACTAAAGGTTCCTTTCCCCCTCTAGGGTCCACCT

GTTAATCAATCTTAAATTGTTGCCAATTACACATCTTGAATACATAGAGATTATTTAT

ATTGTTTTTTAACCCCTTGGTCAATTTGCATATATTGAGCTTTTTAAAGTTTTAATCA

TTAGTTGGTTCTTCTAAGAATCATGAGTCAGGAGCAGGGATTTTTTTTAACTTATTTT

GGATTTATAGTCACCACTACCACTTTTATTATTACCTGCCAGTTCAAGATAGTTATTT

ATTTTTATTTTATATTATTATTATTATTATCATCATCATTATTTTGAGATGGAGTC

TCACTCTGTTGCCCAGGCTGGAGTGCAGTGGTGCAATCTCGGCTCACTGCAACCTCT

GCCTCCCAGGTTCAAGCAATTCTCCCTGCTTCAGCCTCCAGATTAGCTGGGATTACA

GGCACCCCTCACCACATCCAGCTAATTTTTGGATTTTTTAGTAGAGATGGGGGTTTG

CCATGTTGGCCAGGCTGGTTTTGAACTCTTGACCTCAGGTGATCCACCTGCCTTGGCC

TCCCAAAGTGTTAGGATTACAAGTGTGAGCCACCGAGCCTGGCCAAGATAGTTTAA

AAAAAAATTATATCTACATTAAAGCCACAAGTCACCCTTTGCTGAAGTCAGATATTA

GTAGTTGGAAGCAGTGTGTTATTCTTGACCCCATGAAGTGGCACTTATTAAGTAGCT
```

```
-continued
TGCTTTTCCATAATTATGGCCTAGCTTTTTAAAACCTACTATGAACACCACAAGCATA

GAGTTTTCCAAAAGTTCAAGAAGGAAAGGAAACCAATTATACTGAATCAGGTAGAT

TCTTAACTGAAATAATTAGATGTTTTAATAGCCTCTTATGAACTTTCTTCCAGAACCA

AAAACTTTTGCTAGAAAATCAGCTTTTACGAGAGAAAACTCATGGCCTTGTAGTTGA

GAACCAGGAGTTAAGACAGCGCTTGGGGATGGATGCCCTGGTTGCTGAAGAGGAGG

CGGAAGCCAAGGTAAATCATCTCCTTTATTTGGTGCCTCATGTGAGTACTGGTTCCA

AGTGACATGACCCAGCGATTATGTTTACAGTCTGGACTTCTGATCAAGAGCGTTCTT

GAAATTTTCCTTCAGTTTTAAGACATTTTCATGCAGGCAGAGTGTTCTTCCCCTAAAG

GCACTTGACACTCATTTTTAAGTGTGTAGTGAACAGTACTAAGATCTAATAATGAA

AACAAGTTACATGGCTCCCTAAGAACAAGTACTAACAAATGCAGTAGCCAACAAGA

TTACCATGCAATCATTAAGGAGAACCAAAGTAAGAGAGCCACTCAAACCAGATTTT

GAACGCTACTAAAATTAAAGTAGTTCTTTGATGAATATGAATGAGTAGGGAAAGGA

TTCTTTGTAATAGTGATACCTCTGTGGTAAGAGAAGGGTGGTATGTGAGTTTTAGTC

TACAGATTATGGCAAATTCAGTGACAACAATCAAATGGTCTAAGATTGACAGTAGC

ACAGTTTTACTCTGTGAAGGTAATGTTCAGGACAAATTTCAAGAAAACTAGAAAACC

ATTCTTTACAGCTGAAATCTTTCCCTAACCATTGTTATTTCCACTTTTAAGTCCTCAA

GAGATGAGAAAAGGGAGGTAAGGCTTCCTTATACATTTCCTGCACAATGAAACATTT

TTCCTCCTCCAGGCAAAGATTCAAGCAGAACTGGCAAATATCTTATCTTGCTCTTCTC

AATAATAATAATGTTGTTAGATAATAAAGTTCTATAGCAATTTAACCCTAGAATCTT

TTTGAAAAGTAATTCTTTAAAGTTGAGAATCACAGCTGTCTAGCAAGCATTTCCTTG

GGCACTTGAAGCTGTTTATTCACTTTGGTCTTTCCTCCCAGGGGAATGAAGTGAGGC

CAGTGGCCGGGTCTGCTGAGTCCGCAGCACTCAGACTACGTGCACCTCTGCAGCAG

GTGCAGGCCCAGTTGTCACCCCTCCAGAACATCTCCCCATGGATTCTGGCGGTATTG

ACTCTTCAGATTCAGAGGTAGGGATCATTCTGACTTATTAAAGAGCTATATAACCAG

TTAATTCCATCTGTTTGATGCTTGACATCCCTAACTAGACAGATGAGGGTTGAAGTT

AGTTTTTGGTGGGGTTGGAGGTGAACATCAACTACCTTCCTAGTTCCAGGTAATATA

GAACATGGAGTGAAGTGTAGATAAATGGGTCTGGTGGGTCCCGAGGTCATCTTATC

ACATAATGACTAATTTACATTATGGAACCCAGTACAAAGTGTTCCAGTTAGATTTTC

CATTGTATTCTGACAGTTGTACTTCATTTAATTTTTGCCTCTTACAGTCTGATATCCTG

TTGGGCATTCTGGACAACTTGGACCCAGTCATGTTCTTCAAATGCCCTTCCCCAGAG

CCTGCCAGCCTGGAGGAGCTCCCAGAGGTCTACCCAGAAGGACCCAGTTCCTTACC

AGCCTCCCTTTCTCTGTCAGTGGGGACGTCATCAGCCAAGCTGGAAGCCATTAATGA

ACTAATTCGTTTTGACCACATATATACCAAGCCCCTAGTCTTAGAGATACCCTCTGA

GACAGAGAGCCAAGCTAATGTGGTAGTGAAAATCGAGGAAGCACCTCTCAGCCCCT

CAGAGAATGATCACCCTGAATTCATTGTCTCAGTGAAGGAAGAACCTGTAGAAGAT

GACCTCGTTCCGGAGCTGGGTATCTCAAATCTGCTTTCATCCAGCCACTGCCCAAAG

CCATCTTCCTGCCTACTGGATGCTTACAGTGACTGTGGATACGGGGGTTCCCTTTCCC

CATTCAGTGACATGTCCTCTCTGCTTGGTGTAAACCATTCTTGGGAGGACACTTTTGC

CAATGAACTCTTTCCCCAGCTGATTAGTGTCTAAGGAATGATCCAATACTGTTGCCC

TTTTCCTTGACTATTACACTGCCTGGAGGATAGCAGAGAAGCCTGTCTGTACTTCATT

CAAAAAGCCAAAATAGAGAGTATACAGTCCTAGAGAATTCCTCTATTTGTTCAGATC
```

```
                       -continued
TCATAGATGACCCCCAGGTATTGTCTTTTGACATCCAGCAGTCCAAGGTATTGAGAC

ATATTACTGGAAGTAAGAAATATTACTATAATTGAGAACTACAGCTTTTAAGATTGT

ACTTTTATCTTAAAAGGGTGGTAGTTTTCCCTAAAATACTTATTATGTAAGGGTCATT

AGACAAATGTCTTGAAGTAGACATGGAATTTATGAATGGTTCTTTATCATTTCTCTTC

CCCCTTTTTGGCATCCTGGCTTGCCTCCAGTTTTAGGTCCTTTAGTTTGCTTCTGTAAG

CAACGGGAACACCTGCTGAGGGGGCTCTTTCCCTCATGTATACTTCAAGTAAGATCA

AGAATCTTTTGTGAAATTATAGAAATTTACTATGTAAATGCTTGATGGAATTTTTTCC

TGCTAGTGTAGCTTCTGAAAGGTGCTTTCTCCATTTATTTAAAACTACCCATGCAATT

AAAAGGTACAATGCAGCATCCTTGTTTGATTTCTTCTAGGGCCGTAAGTCTTGTTTTC

TCTCCAGATGTTTATCTGTGTGCTGTGGTAGGAATTAATCCAACTGAAGTGAGCCTA

ACGCTTTTTAAAGTGACTGAAGGCTTTTCCACCTTAATTACTGCCTGCTTTAATTCTG

GACTGCCATAAGTGATATAAGCTATAATTTGAGCAGTTACTGTCTTTCTGAGACAGA

TTCTTGAGCCTAACTGACCAATATCACAGCTAGTAAGTGGAAGAGCTAGAACCCTAA

CCACTATTTGCTACACCATCTTATAAATGTTAAACAAGGACACACCATCACATAT

CGAGATTCTCTTGCCCTTATTATGGGAATTAAGAGCATTTTCTAGACTGAAACTCCCT

ATTTTCAACTCTGCCACTGGTAAGCTGGGTAACCCAGGGGTTATATATAATCACTTA

TTTCCTCATCTGTAAAGTTGGATAATGGTATCTCTAAAGGTTAAGATTCAAAGAGAC

GATGCATTATAAGCATTTAGTATATGCTAGGCACCATCCTAAACACTGGAAAGTTAG

TTAGTTATTATCTCCTAATCCACTTTGGAAGGGTTTTAATCTCTTCCAGAATTATATT

TACTCAAGAATTTGTTTCATCAAAGAATAAACCTCGGCCAGGCGCGGTGGCTCATGC

CTGTAATCCCAGCACTTTGGGAGGCTGAGGCGGGTGGATCACGAGGTCAGGAGATC

GAGACCATCCTGCCTAACATGGGGAAACCCTGTCTCTACTAAAATTACAAAAAATTA

GCCAGGCGTGGTGGTGGGCGCCTGTAATCCCAGCTACTTGGGAGGCTGAGGCAGGA

GAATGGCGTGAACCCGGGAGGCGGAGCTTGCGGTGAGGGGAGATCGCGCCACTGCA

CTCCAGCCTGGGCAACAGAGCGAGACTCTGTCTCAAAAAATAAATAAATAAATAAA

TAAATAAATAAATAAACCTCTTCAAGAAAAAATCCTAGTGATATTAATACAACTCCC

AAAGACTTGATAACCTCCTCATCCTTCATAGCATCTTTTCCTTGGAAATCTTACAAGG

TTTTACAGGACTTTACTTATTTATAAAAATTTCACCTATGCCAGTAGATGAAATCATT

CTATGCCAATTTAGCATTTAAATGCTATGTTCCCAACTTACAAAGACTAACTCTGGG

GAGGTCAAAGTGAATGAGTAGAAAAAAGGCAGGATTCAGAGAATCCCAAGCAGCA

AGGCAAAGTGGATTATAGAATACCTTTGGTGTAGGCCAGGTGTAGTGGCTCACGCTT

GTAATCCCAACACTTTGGGAGGCTGAGGTGGGCGGATCACCTGAGGTCAGGAGTTC

ATGGCCAGCCTGACCAACATAGTGAAACCCCATCTCTAGTAAAAATACAAAATTAG

CTGGGTGTGGTGGCGCATATGCCTGTAATCCCAGCTACTCAGGAGGCTGAGGCGGC

AGAATCACTTGAACCCGGGAGGCAGAGGATGCAGCGAGCCGAGATCGTGCCATTG

CACTCCAGCCTGGGCAACAAGAGCGAAACTCCATTTAAAAAAGAAAAAAAAAATA

GAATGCCTTTCATGTAGTGACTGGAGGCAAGTCAGCTAGCTGCCTTCAAGATCCGGT

CGTTGAAGCCAGGGCCCAATCCTGGTGCTCAGCAATACAAACTTGCTTAGGCTCTTA

AGTTTCTTCAGAAACAGGCCAGGCATGGTGGCTCACACCTATAATCCCAGCACTTTG

GGAGGCCGAGGCCAGCAGATTGCTTGGTTCAAGACTAGCCTGGACAACATGGCAAA

CCCGTCTCTCCATGAAAAGTAAAAAAAAAATAGCCAGGCATGGTGGTGTGCACTGGT
```

```
                        -continued
GGTCACAGCCACTCAGGAAGCTGAGGTGGGAGGATCGCTTGAGGCCAGGGGGCAGA

GGTTGCAGTCAGCCAAGATCGCAGCACTGCACTCCAGACTGGGTGAAAAAGCAAGA

CTGCCTAAAAAAAAAAAGGTTCTGTATATAAG.
```

As used herein, FOXO1 refers to a forkhead box 1 polypeptide. When preparing a T cell or treating a mammal with a T cell, FOXO1 refers to human FOXO1. An example of a human FOXO1 polypeptide includes, without limitation, NCBI reference sequence: NP_002006.2.

As used herein, ID2 refers to an inhibitor or DNA binding 2 polypeptide. When preparing a T cell or treating a mammal with a T cell, ID2 refers to human ID2. An example of a human ID2 polypeptide includes, without limitation, NCBI reference sequence: NP_002157.2.

As used herein, ID3 refers to an inhibitor or DNA binding 3 polypeptide. When preparing a T cell or treating a mammal with a T cell, ID3 refers to human ID3. An example of a human ID3 polypeptide includes, without limitation, NCBI reference sequence: NP_002158.3.

As used herein, IRF4 refers to a interferon regulatory factor 4 polypeptide. When preparing a T cell or treating a mammal with a T cell, IRF4 refers to human IRF4. An example of a human IRF4 polypeptide includes, without limitation, NCBI reference sequence: NP_001182215.1.

As used herein, LEF1 refers to a lymphoid enhancer binding factor 1 polypeptide. When preparing a T cell or treating a mammal with a T cell, LEF1 refers to human LEF1. An example of a human LEF1 polypeptide includes, without limitation, NCBI reference sequence: NP_001124185.1.

As used herein, SATB1 refers to a SATB1 homeobox 1 polypeptide. When preparing a T cell or treating a mammal with a T cell, SATB1 refers to human SATB1. An example of a human SATB1 polypeptide includes, without limitation, NCBI reference sequence: NP_001124482.1.

As used herein, RUNX1 refers to a RUNX family transcription factor 1 polypeptide. When preparing a T cell or treating a mammal with a T cell, RUNX1 refers to human RUNX1. An example of a human RUNX1 polypeptide includes, without limitation, NCBI reference sequence: NP_001001890.1.

As used herein, BCL11b refers to a BAF chromatin remodeling complex subunit BCL11b polypeptide. When preparing a T cell or treating a mammal with a T cell, BCL11b refers to human BCL11b. An example of a human BCL11b polypeptide includes, without limitation, NCBI reference sequence: NP_001269166.1.

As used herein, FOXP1 refers to a forkhead box P1 polypeptide. When preparing a T cell or treating a mammal with a T cell, FOXP1 refers to human v. An example of a human FOXP1 polypeptide includes, without limitation, NCBI reference sequence: NP_001012523.1.

As used herein, FOXP4 refers to a forkhead box P4 polypeptide. When preparing a T cell or treating a mammal with a T cell, FOXP4 refers to human v. An example of a human FOXP4 polypeptide includes, without limitation, NCBI reference sequence: NP_001012426.1.

As used herein, BACH2 refers to a BTB domain and CNC homolog 2 polypeptide. When preparing a T cell or treating a mammal with a T cell, BACH2 refers to human BACH2. An example of a human BACH2 polypeptide includes, without limitation, NCBI reference sequence: NP_001164265.1.

As used herein, STAT3 refers to a signal transducer and activator of transcription 3 polypeptide. When preparing a T cell or treating a mammal with a T cell, STAT3 refers to human STAT3. An example of a human STAT3 polypeptide includes, without limitation, NCBI reference sequence: NP_001356441.1.

As used herein XBP1 refers to an X-box binding protein 1 polypeptide. When preparing a T cell or treating a mammal with a T cell, XBP1 refers to human XBP1. An example of a human XBP1 polypeptide includes, without limitation, NCBI reference sequence: NP_005071.2.

Antigen-Binding Domains

As used herein, the term "antibody," "antigen-binding domain," or "antigen-binding fragment" refers to an intact immunoglobulin or to an antigen-binding portion thereof. In some embodiments, a binding agent refers to an intact immunoglobulin or to an antigen-binding portion thereof. Antigen-binding portions may be produced by recombinant DNA techniques or by enzymatic or chemical cleavage of intact antibodies. Examples of antigen-binding portions include Fab, Fab', F(ab')$_2$, Fv, domain antibodies (dAbs), and complementarity determining region (CDR) fragments, single-chain antibodies (scFv), chimeric antibodies, diabodies, triabodies, tetrabodies, and polypeptides that contain at least a portion of an immunoglobulin that is sufficient to confer specific antigen-binding to the polypeptide. As used herein, the term "scFv" antibody fragments comprise the VH and VL domains of an antibody, wherein these domains are present in a single polypeptide chain. Included in the definition are single domain antibody, including camelids. In some cases, the antibody is human or humanized.

In some embodiments, any of the "antigen-binding domains," "antibodies," "ligand binding domains," or "binding agents" described herein can bind specifically to a target selected from the group of: CD16a, CD28, CD3 (e.g., one or more of CD3α, CD3β, CD3δ, CD3ε, and CD3γ), CD33, CD20, CD19, CD22, CD123, IL-1R, IL-1, VEGF, IL-6R, IL-4, IL-10, LAG3, PDL-1, TIGIT, PD-1, TIM3, CTLA4, MICA, MICB, IL-6, IL-8, TNFα, CD26a, CD36, ULBP2, CD30, CD200, IGF-1R, MUC4AC, MUC5AC, Trop-2, CMET, EGFR, HER1, HER2, HER3, PSMA, CEA, B7H3, EPCAM, BCMA, P-cadherin, CEACAM5, a UL16-binding protein (e.g., ULBP1, ULBP2, ULBP3, ULBP4, ULBP5, and ULBP6), HLA-DR, DLL4, TYRO3, AXL, MER, CD122, CD155, PDGFDD, a ligand of TGF-β receptor II (TGF-βRII), a ligand of TGF-ββRIII, a ligand of DNAM1, a ligand of NKp46, a ligand of NKp44, a ligand of NKG2D, a ligand of NK30, a ligand for a scMHCI, a ligand for a scMHCII, a ligand for a scTCR, a receptor for IL-1, a receptor for IL-2, a receptor for IL-3, a receptor for IL-7, a receptor for IL-8, a receptor for IL-10, a receptor for IL-12, a receptor for IL-15, a receptor for IL-17, a receptor for IL-18, a receptor for IL-21, a receptor for PDGF-D, a receptor for stem cell factor (SCF), a receptor for stem cell-like tyrosine kinase 3 ligand (FLT3L), a receptor for MICA, a receptor for MICB, a receptor for a ULP16-binding protein, a receptor for CD155, a receptor for CD122, and a receptor for CD28.

In some embodiments, any of the "antigen-binding domains," "antibodies," "ligand binding domains," or "binding agents" further include a secretion signal peptide. For example, a nucleic acid sequence encoding a binding agent further includes a nucleic acid sequence encoding a secretion signal peptide.

As used herein, ICAM-1 refers to intercellular adhesion molecule 1 polypeptide. When preparing the T cell or treating a mammal with the T cell, ICAM-1 refers to human ICAM-1. An example of a human ICAM-1 polypeptide includes, without limitation, NCBI reference sequence: NP_000192.2 or a fragment thereof.

As used herein, VCAM-1 refers to vascular cell adhesion molecule 1 polypeptide. When preparing the T cell or treating a mammal with the T cell, VCAM-1 refers to human VCAM-1. An example of a human VCAM-1 polypeptide includes, without limitation, NCBI reference sequence: NP_001069.1 or a fragment thereof.

As used herein, LFA-1 also known as ITGB2 refers to lymphocyte function associated antigen-1 (LFA-1) polypeptide or integrin subunit beta 2 (ITGB2) polypeptide. When preparing the T cell or treating a mammal with the T cell, LFA-1 or ITGB2 refers to human LFA-1 or ITGB2. An example of a human LFA-1 or ITGB2 polypeptide includes, without limitation, NCBI reference sequence: NP_000620.2 or a fragment thereof.

As used herein, TGFBR2 refers to transforming growth factor beta receptor 2. When preparing the T cell or treating a mammal with the T cell, TGFBR2 refers to human TGFBR2. An example of a human TGFBR2 polypeptide includes, without limitation, NCBI reference sequence: NP_001020018.1 or a fragment thereof.

As used herein, IFNAR1 refers to interferon (alpha and beta) receptor 1. When preparing the T cell or treating a mammal with the T cell, IFNAR1 refers to human IFNAR1. An example of a human IFNAR1 polypeptide includes, without limitation, NCBI reference sequence: NP_000620.2 or a fragment thereof.

Methods of Producing T Cells

As described herein, any appropriate method of producing cells (e.g., T cells) comprising a FOXP3 polypeptide and one or more transcription factors can be used to generate the T cells as described herein. In some embodiments, a cell (e.g., a T cell) that is transduced with the nucleic acid sequences described herein is isolated from a mammal (e.g., a human) using any appropriate method (e.g., magnetic activated sorting or flow cytometry-mediated sorting). In some cases, nucleic acid sequences encoding a FOXP3 polypeptide and one or more transcription factors can be transformed into a cell (e.g., a T cell) along with nucleic acid sequences encoding a therapeutic gene product and/or a binding agent. For example, a T cell can be made by transducing nucleic acid sequences encoding a FOXP3 polypeptide and one or more transcription factors into a cell (e.g., a T cell) using a lentivirus. In another example, a T cell can be made by transducing nucleic acid sequences encoding a FOXP3 polypeptide, one or more transcription factors, and a therapeutic gene product into a cell (e.g., a T cell) using a lentivirus. In yet another example, a T cell can be made by co-transducing nucleic acid sequences encoding a FOXP3 polypeptide, one or more transcription factors, a therapeutic gene product, and a binding agent into an immune cell (e.g., a T cell) using a lentivirus. In all cases described herein, the nucleic acid sequences are operably linked to a promoter or are operably linked to other nucleic acid sequences using a self-cleaving 2A polypeptide or IRES sequence.

Methods of introducing nucleic acids and expression vectors into a cell (e.g., a eukaryotic cell) are known in the art. Non-limiting examples of methods that can be used to introduce a nucleic acid into a cell include lipofection, transfection, electroporation, microinjection, calcium phosphate transfection, dendrimer-based transfection, cationic polymer transfection, cell squeezing, sonoporation, optical transfection, impalefection, hydrodynamic delivery, magnetofection, viral transduction (e.g., adenoviral and lentiviral transduction), and nanoparticle transfection. As used herein, "transformed" and "transduced" are used interchangeably.

In some embodiments, the transformed cell can be an immune cell, an epithelial cell, an endothelial cell, or a stem cell. In some embodiments, the transformed cell is an immune cell selected from the group consisting of a T cell, a B cell, a natural killer (NK) cell, a dendritic cell, a macrophage, a regulatory T cell, a helper T cell and a cytotoxic T cell. In some examples, the immune cell is a NK cell, and the detection of a memory NK cell can include, for example, the detection of the level of one or more of IL-12, IL-18, IL-33, STAT4, Zbtb32, DNAM-1, BIM, Noxa, SOCS1, BNIP3, BNIP3L, interferon-γ, CXCL16, CXCR6, NKG2D, TRAIL, CD49, Ly49D, CD49b, and Ly79H. A description of NK memory cells and methods of detecting the same is described in O'Sullivan et al., *Immunity* 43:634-645, 2015. In some examples, the immune cell is a T cell, and the detection of memory T cells can include, e.g., the detection of the level of expression of one or more of CD45RO, CCR7, L-selectin (CD62L), CD44, CD45RA, integrin αeβ7, CD43, CD4, CD8, CD27, CD28, IL-7Rα, CD95, IL-2Rβ, CXCR3, and LFA-1. Additional examples of T-cells that can be transduced are described herein.

Nucleic Acids/Vectors

Also provided herein are nucleic acids sequences that encode any of the polypeptides described herein. For example, nucleic acid sequences are included that encode for a FOXP3 polypeptide, one or more transcription factors, a therapeutic agent comprising a polypeptide, and a binding agent comprising a polypeptide. Also provided herein are vectors that include any of the nucleic acid sequences encoding any of the polypeptides described herein. For example, the polypeptides include, without limitation, a FOXP3 polypeptide, one or more transcription factors, a therapeutic agent comprising a polypeptide, and a binding agent comprising a polypeptide.

Any of the vectors described herein can be an expression vector. For example, an expression vector can include a promoter sequence operably linked to the sequence encoding any of the polypeptides as described herein. Non-limiting examples of vectors include plasmids, transposons, cosmids, and viral vectors (e.g., any adenoviral vectors (e.g., pSV or pCMV vectors), adeno-associated virus (AAV) vectors, lentivirus vectors, and retroviral vectors), and any Gateway® vectors. In some cases, a vector can include sufficient cis-acting elements that supplement expression where the remaining elements needed for expression can be supplied by the host mammalian cell or in an in vitro expression system. Skilled practitioners will be capable of selecting suitable vectors and mammalian cells for making any of the T cells as described herein. Any appropriate promoter (e.g., EF1 alpha) can be operably linked to any of the nucleic acid sequences described herein. Non-limiting examples of promoters to be used in any of the vectors or constructs described herein include EF1a, SFFV, PGK, CMV, CAG, UbC, MSCV, MND, EF1a hybrid, and/or CAG hybrid. As used herein, the term "operably linked" is well known in the art and refers to genetic components that are combined such that they carry out their normal functions. For example, a nucleic acid sequence is operably linked to a promoter when its transcription is under the control of the promoter. In another example, a nucleic acid sequence can be operably linked to other nucleic acid sequence by a self-cleaving 2A polypeptide or an internal ribosome entry site (IRES). In such cases, the self-cleaving 2A polypeptide allows the second nucleic acid sequence to be under the control of the promoter operably linked to the first nucleic acid sequence. The nucleic acid sequences described herein can be operably linked to a promoter. In some cases, the nucleic acid sequences described herein can be operably linked to any other nucleic acid sequence described herein using a self-cleaving 2A polypeptide or IRES. In some cases, the nucleic acid sequences are all included on one vector and operably linked either to a promoter upstream of the nucleic acid sequences or operably linked to the other nucleic acid sequences through a self-cleaving 2A polypeptide or an IRES.

Compositions

Also provided herein are compositions (e.g., pharmaceutical compositions) that include at least one of any of the polypeptides (e.g., FOXP3 polypeptides, one or more transcription factors, therapeutic polypeptides, and binding agent polypeptides), any of the cells, or any of the nucleic acids or vectors described herein. In some embodiments, the compositions include at least one of the any of polypeptides (e.g., FOXP3 polypeptides, one or more transcription factors, therapeutic polypeptides, and binding agent polypeptides) described herein. In some embodiments, the compositions include any of the cells (e.g., any of the cells described herein including any of the cells produced using any of the methods described herein). In some embodiments, the pharmaceutical compositions are formulated for different routes of administration (e.g., intravenous, subcutaneous). In some embodiments, the pharmaceutical compositions can include a pharmaceutically acceptable carrier (e.g., phosphate buffered saline).

Cells

Also provided herein are cells (e.g., any of the exemplary cells described herein or known in the art) comprising any of the nucleic acid sequences described herein that encode any of the polypeptides (e.g., FOXP3 polypeptides, one or more transcription factors, therapeutic polypeptides, and/or binding agent polypeptides) described herein. Also provided herein are cells (e.g., any of the exemplary cells described herein or known in the art) that include any of the vectors described herein. In some embodiments, the cells are any of the exemplary types of T cells described herein or known in the art.

In some embodiments of any of the methods described herein, the cell can be a eukaryotic cell. As used herein, the term "eukaryotic cell" refers to a cell having a distinct, membrane-bound nucleus. Such cells may include, for example, mammalian (e.g., rodent, non-human primate, or human) cells. Non-limiting examples of mammalian cells include Chinese hamster ovary cells and human embryonic kidney cells (e.g., HEK293 cells).

Methods of Treatment

Also provided herein are methods of treating a mammal (e.g., a human) having an autoimmune disease that includes administering to the mammal (e.g., human) a therapeutically effective amount of a cell (e.g., any of the exemplary T cells described herein) or any of the compositions (e.g., pharmaceutical compositions) described herein.

In some embodiments, these methods can result in a reduction in the number, severity, or frequency of one or more symptoms of the autoimmune diseases in the mammal (e.g., as compared to the number, severity, or frequency of the one or more symptoms of the autoimmune disease in the mammal prior to treatment). For example, a mammal having an autoimmune disease having been administered a T cell as described here can experience a reduction in inflammation or autoantibody production.

Any appropriate method of administration can be used to administer the T cells to a mammal (e.g. a human) having an autoimmune disease. Examples of methods of administration include, without limitation, parenteral administration and intravenous injection.

A pharmaceutical composition containing the T cells and a pharmaceutically acceptable carrier or buffer can be administered to a mammal (e.g., a human) having an autoimmune disease. For example, a pharmaceutical composition (e.g., a T cell along with a pharmaceutically acceptable carrier) to be administered to a mammal having an autoimmune disease can be formulated in an injectable form (e.g., emulsion, solution and/or suspension). In some embodiments, a pharmaceutical composition containing the T cells can include phosphate buffered saline.

Pharmaceutically acceptable carriers, fillers, and vehicles that can be used in a pharmaceutical composition described herein can include, without limitation, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat.

Effective dosage can vary depending on the severity of the autoimmune disease, the route of administration, the age and general health condition of the subject, excipient usage, the possibility of co-usage with other therapeutic treatments, and the judgment of the treating physician. An effective amount of a T cell can be any amount that reduces inflammation and autoantibody production within a mammal having an autoimmune disease without producing significant toxicity to the mammal. For example, an effective amount of T cells administered to a mammal having an autoimmune disease can be from about $1 \times 10^6$ cells to about $1 \times 10^{10}$ (e.g., from about $1 \times 10^6$ to about $1 \times 10^9$, from about $1 \times 10^6$ to about $1 \times 10^8$, from about $1 \times 10^6$ to about $1 \times 10^7$, from about $1 \times 10^7$ to about $1 \times 10^{10}$, from about $1 \times 10^7$ to about $1 \times 10^9$, from about $1 \times 10^7$ to about $1 \times 10^8$, from about $1 \times 10^8$ to about $1 \times 10^{10}$, from about $1 \times 10^8$ to about $1 \times 10^9$, or form about $1 \times 10^9$ to about $1 \times 10^{10}$ cells. In some cases, the T cells can be a purified population of immune cells generated as described herein. In some cases, the purity of the population of T cells can be assessed using any appropriate method, including, without limitation, flow cytometry. In some cases, the population of T cells to be administered can include a range of purities from about 70% to about 100%, from about 70% to about 90%, from about 70% to about 80%, from about 80% to about 90%, from about 90% to about 100%, from about 80% to about 100%, from about 80% to about 90%, or from about 90% to about 100%. In some cases, the dosage (e.g., number of T cells to be administered) can adjusted based on the level of purity of the T cells.

The frequency of administration of a T cell can be any frequency that reduces inflammation or autoantibody production within a mammal having an autoimmune disease without producing toxicity to the mammal. In some cases, the actual frequency of administration can vary depending on various factors including, without limitation, the effective amount, duration of treatment, use of multiple treatment agents, route of administration, and severity of the condition may require an increase or decrease in frequency of administration.

An effective duration for administering a composition containing a T cell can be any duration that reduces inflammation or autoantibody production within a mammal having an autoimmune disease without producing toxicity to the mammal. In some cases, the effective duration can vary from several days to several months. In general, the effective treatment duration for administering a composition containing a T cell to treat an autoimmune disease can range in duration from about one month to about five years (e.g., from about two months to about five years, from about three months to about five years, from about six months to about five years, from about eight months to about five years, from about one year to about five years, from about one month to about four years, from about one month to about three years, from about one month to about two years, from about six months to about four years, from about six months to about three years, or from about six months to about two years). In some cases, the effective treatment duration for administering a composition containing a T cell can be for the remainder of the life of the mammal.

In some cases, a course of treatment and/or the severity of one or more symptoms related to autoimmune disease can be monitored. Any appropriate method can be used to determine whether the autoimmune disease is being treated. For example, immunological techniques (e.g., ELISA) can be performed to determine if the level of autoantibodies present within a mammal being treated as described herein is reduced following the administration of the T cells. Remission and relapse of the disease can be monitored by testing for one or more markers of autoimmune disease.

Any appropriate autoimmune disease can be treated with a T cell as described herein. In some cases, an autoimmune disease caused by the accumulation of autoantibodies can be treated with a T cell as described herein. Examples of autoimmune diseases include, without limitation, lupus, rheumatoid arthritis, multiple sclerosis, insulin dependent diabetes mellitus, myasthenia gravis, Grave's disease, autoimmune hemolytic anemia, autoimmune thrombocytopenia purpura, Goodpasture's syndrome, pemphigus vulgaris, acute rheumatic fever, post-streptococcal glomerulonephritis, Crohn's disease, Celiac disease, and polyarteritis nodosa.

The invention will be further described in the following examples, which do not limit the scope of the invention described in the claims.

EXAMPLES

Example 1. T Cell Transduced with Nucleic Acid Sequences Encoding FOXP3 and BLIMP1

A set of experiments is performed to assess the effect of co-expression of a BLIMP1 polypeptide and a FOXP3 polypeptide. In these experiments, CD4$^+$ T cells are transduced with a lentivirus where the lentiviral vector includes a first nucleic acid sequence encoding a FOXP3 polypeptide harboring mutations in NES1 and NES2 that result in nuclear localization of FOXP3 and a second nucleic acid sequence encoding BLIMP1 polypeptide. The vector includes an EF1α promoter. Lentivirus is produced in HEK293 cells according to standard protocols.

CD4$^+$ T cells are counted and checked for viability. Next cells are re-suspended in fresh serum free ImmunoCult T cell expansion media at a concentration of 10$^6$ cells/mL. Then 500 μL (~500,000 cells) of the cell suspension is aliquoted to each well. The cells are then cultured in the presence of CD3/CD28 for 1-2 days prior to addition of virus. Different concentrations of lentiviral particles are added to each well for the desired target MOI. The plates are then sealed with parafilm, and the cells are spun in a table top centrifuge at 300×g for 5 minutes. After spinoculation, the cells are incubated at 37° C. The cells are then assessed for FOXP3 expression and cellular localization, BLIMP1 expression, and expression of a T reg phenotype.

Example 2

Table 1 (below) shows the percentage of Mean Fluorescence Intensity (MFI) as compared to donor-matched expanded Tregs.

Each column represents values for synReg transduced with FOXP3 alone or co-transduced with FOXP3 and the indicated modifier. Each row displays data for the specified marker. Values are displayed as mean of 3 donors±SD, *p<0.05, **p<0.01 by paired t-test of co-transduced modifier versus FOXP3 alone.

TABLE 1

Percentage of Mean Fluorescence Intensity (MFI) as compared to donor-matched expanded Tregs.

|  | FOXP3 only | FOXP3 and ID2 | FOXP3 and ID3 | FOXP and GATA1 | FOXP3 and GATA3 | FOXP3 and XBP1 | FOXP3 and SATB1 |
|---|---|---|---|---|---|---|---|
| CTLA4 | 119.6 ± 24.5 | 248.3 ± 100.8 | 226.1 ± 58.5, * | 207.5 ± 48.0 | 167.5 ± 19.5, * | 121.5 ± 22.4 | 129.2 ± 31.7 |
| CD25 | 206.9 ± 130.8 | 322.0 ± 202.6 | 274.7 ± 166.8 | 293.8 ± 142.8 | 230.2 ± 115.1 | 281.3 ± 147.9, * | 257.1 ± 168.0 |
| ICOS | 239.9 ± 123.0 | 564.1 ± 355.1 | 467.8 ± 284.5 | 205.3 ± 115.2 | 242.7 ± 119.8 | 249.7 ± 138.2 | 239.3 ± 134.4 |
| LAG3 | 168.28 ± 78.8 | 318.6 ± 146.7 | 256.0 ± 102.5, * | 254.7 ± 38.5 | 207.9 ± 62.5 | 200.0 ± 84.8, * | 191.4 ± 77.7, ** |

Other Embodiments

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A method for increasing human T cell function, wherein the method comprises introducing into a human T cell:
   (i) a first nucleic acid sequence encoding a forkhead box P3 (FOXP3) polypeptide; and
   (ii) a second nucleic acid sequence encoding one or more transcription factor(s) selected from the group consisting of: ID2, ID3, GATA1, GATA3,)(XBP1, and SATB1,
   wherein the first nucleic acid sequence and the second nucleic acid sequence are disposed in a nucleic acid construct.

2. The method of claim 1, wherein the one or more transcriptions factor(s), when present in a human cell, elicit(s) a Treg phenotype in the human cell as compared to when the one or more transcription factor(s) is/are not present in the human cell.

3. The method of claim 1, wherein the nucleic acid construct further comprises a promoter operably linked to the first nucleic acid sequence, and wherein the first nucleic acid sequence is positioned 5' relative to the second nucleic acid sequence in the nucleic acid construct.

4. The method of claim 1, wherein the nucleic acid construct further comprises an additional nucleic acid sequence between the first nucleic acid sequence and the second nucleic acid sequence, wherein the additional nucleic acid sequence operably links the second nucleic acid sequence to the first nucleic acid sequence, and wherein the second nucleic acid sequence is positioned 5' relative to the first nucleic acid sequence in the nucleic acid construct.

5. The method of claim 1, wherein the nucleic acid construct further comprises an additional nucleic acid sequence between the second nucleic acid sequence and the first nucleic acid sequence, wherein the additional nucleic acid sequence operably links the first nucleic acid sequence to the second nucleic acid sequence.

6. The method of claim 5, wherein the additional nucleic acid sequence encodes (i) an internal ribosome entry site (IRES) sequence or a self-cleaving amino acid, and (ii) a promoter or an enhancer.

7. The method of claim 1, wherein the nucleic acid construct comprises a viral vector selected from the group consisting of: a lentiviral vector, a retroviral vector, an adenoviral vector, and an adeno-associated viral (AAV) vector, and wherein the introducing step comprises viral transduction.

8. The method of claim 1, wherein the human T cell is a human CD4$^+$T cell or a human CD4$^+$/CD45RA$^+$T cell.

9. The method of claim 1, wherein the method further comprises, prior to the introducing step:
   obtaining a human T cell from a human patient or obtaining human T cells allogenic to a human patient and treating the obtained human T cells to isolate a population of cells enriched for human CD4$^+$T cells or human CD4$^+$/CD45RA$^+$T cells.

10. The method of claim 1, wherein the one or more transcriptions factor(s) is ID2.

11. The method of claim 1, wherein the one or more transcriptions factor(s) is ID3.

12. The method of claim 1, wherein the one or more transcriptions factor(s) is GATA1.

13. The method of claim 1, wherein the one or more transcriptions factor(s) is GATA3.

14. The method of claim 1, wherein the one or more transcriptions factor(s) is)(XBP1.

15. The method of claim 1, wherein the one or more transcriptions factor(s) is SATB1.

* * * * *

UNITED STATES PATENT AND TRADEMARK OFFICE
CERTIFICATE OF CORRECTION

| | |
|---|---|
| PATENT NO. | : 11,446,357 B2 |
| APPLICATION NO. | : 17/552841 |
| DATED | : September 20, 2022 |
| INVENTOR(S) | : Ashley Mahne et al. |

It is certified that error appears in the above-identified patent and that said Letters Patent is hereby corrected as shown below:

In the Claims

Column 109, Line 23, in Claim 1, delete "GATA3,)(XBP1," and insert -- GATA3, XBP1, --.

Column 110, Approximately Line 46, in Claim 14, delete "is)(XBP1." and insert -- is XBP1. --.

Signed and Sealed this
Fifteenth Day of November, 2022

Katherine Kelly Vidal
*Director of the United States Patent and Trademark Office*